US008097599B2

(12) United States Patent
Fischer

(10) Patent No.: US 8,097,599 B2
(45) Date of Patent: Jan. 17, 2012

(54) PLASMID ENCODING FELINE BMP-7

(75) Inventor: Laurent Bernard Fischer, Sainte Foy les Lyon (FR)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 12/794,184

(22) Filed: Jun. 4, 2010

(65) Prior Publication Data

US 2010/0261782 A1     Oct. 14, 2010

Related U.S. Application Data

(63) Continuation of application No. 11/803,991, filed on May 16, 2007, now Pat. No. 7,771,995, which is a continuation-in-part of application No. 11/801,798, filed on May 11, 2007, now abandoned, which is a continuation-in-part of application No. 11/599,026, filed on Nov. 14, 2006, now Pat. No. 7,598,364.

(60) Provisional application No. 60/736,452, filed on Nov. 14, 2005.

(51) Int. Cl.
    *C12N 15/00* (2006.01)
(52) U.S. Cl. .................... 514/44; 435/320.1
(58) Field of Classification Search .............. 435/320.1; 514/44; 424/93.2
    See application file for complete search history.

(56) References Cited

U.S. PATENT DOCUMENTS

| 5,141,905 A | 8/1992 | Rosen et al. |
| 5,652,337 A | 7/1997 | Oppermann et al. |
| 5,866,364 A * | 2/1999 | Israel et al. ................... 435/69.1 |
| 6,861,404 B1 | 3/2005 | Cohen |

FOREIGN PATENT DOCUMENTS

| CN | 1443847 | * | 9/2003 |
| EP | 1571159 | | 9/2005 |
| WO | WO 90/11366 | | 10/1990 |
| WO | WO 02/47713 | | 6/2002 |
| WO | WO 02/099037 | | 12/2002 |
| WO | WO 2004/019876 | | 3/2004 |
| WO | WO 2008/030413 | | 3/2008 |

OTHER PUBLICATIONS

Miller 1995, FASEB J., vol. 9, p. 190-199.*
Deonarain, 1998, Expert Opin. Ther. Pat., vol. 8, p. 53-69.*
Verma, Sep. 1997, Nature, vol. 389, p. 239-242.*
Crystal, 1995, Science, vol. 270, p. 404-410.*
Ross, Sep. 1996, Human Gene Therapy, vol. 7, p. 1781-1790.*
Davies (J. Am. Soc. Nephrol. 2003, vol. 14, p. 1559-1567).*
Imai (Curr. Opin. Nephrology and Hypertension, 2002, vol. 11, p. 49-57).*
Li (Zhonghua Yi Xue Za Zhi, Feb. 2006, vol. 86, No. 8, p. 544-548).*
Zeisberg (Nephrol Dial Transplant, 2006, vol. 21, p. 568-573).*
Wang (J. Am. Soc. Nephrol. 2006, vol. 17, p. 2504-2512).*

Bright, Corinne, et al., "in vivo evaluation of plasmid DNA encoding OP1 protein for spine fusion", SPINE, vol. 31, No. 19 (2006) pp. 2163-2172.
Crystal (1995), "Transfer of genes to Humans: early lessons and obstacles to success", Science, vol. 270. p. 404-410.
Database Accession No. XM862314, also known as GI: 73992343.
Database Accession No. XM862314, also known as GI: 73992345.
Database Accession No. XM862334, also known as GI:73992341.
Database EMBL, *Homo sapiens* BMP7 gene, Virtual Transcript, partial sequence, genomics survey sequence, database accession No. AY419331 (abstract).
Davies, Mathew R., et al., "BMP-7 is an efficacious treatment of vascular calcification in a murine model of atheroslerosis and chronic renal failure", Journal of the American Society of Nephrology, vol. 14, No. 6 (2003), pp. 1559-1567.
Deonarain (1998), "Ligand-targeted receptor-mediated vectors for gene delivery", Expert Opin. Ther. Pat., vol. 8, p. 53-69.
Franseschi, Rt, et al., "Gene therapy for bone formation: in vitro and in vivo osteogenic activity of an adenovirus expressing BMG7", Journal of Cellular Biochemistry, vol. 78 No. 3 (2000), 476, 486.
Gregory, Kate, et al., "The prodomain of BMP-7 targets the BMP-7 complex to the extracellular matrix", The Journal of Biological Chemistry, vol. 280 (2005) 27970-27980.
Hartikka J., "An improved plasmid DNA expression vector for direct injection intoskeletal muscle", Human Gene Therapy, vol. 7, No. 10, 20 (1996) pp. 1205-1217.
Imai, Enyu, et al., "Targeting growth factors to the Kidney: myth or reality?", Current Opinion in Nephrology and Hypertension Vo. 11, No. 1 (2002), pp. 49-57.
Li, Jz, et al., "Osteogenic potential of five different recombinant human bone morphogenetic protein adenoviral vectors in the rat", Gene Therapy, vol. 10 (2003), pp. 1735-1743.
Li, T, et al., "Bone morphogenetic protein 7: a novel treatment for chronic renal and bone disease", Curr Opin Nephrol Hypertens 13:417-422 (2004).
Li, Ya, et al., "Transfection of recombinant bone morphogenetic protein 7 expressing plasmid into cultured human renal tubular epithelial cells attenuates the extracellular matrix accumulation induced by tranforming growth factor beta", Zhonghua Yi Xue Za Zhi, vol. 86, No. 8 (2006), pp. 544-548 (Abstract).
Miller N., et al., "Targeted vectors for gene therapy", (1955), FASEB J., vol. 9, p. 190-199. Morrissey, et al., "Bone morphogenetic protein-7 improves renal fibrosis and accelerates the return of renal function", J Am Soc Nephrol vol. 13 (2002), pp. 814-821.
Verma Im et al., "Gene therapy-promises, problems and prospects", (1997), Nature, vol. 389, p. 239-242.
Vuklcevic, S., et al, "Osteogenic protein-1 (bone morphogenetic proein-7) reduces severity of injury after ischenic acute renal failure in rat", J. Clin, Invest., vol. 102, No. 1 (1998) pp. 202-214.
Wang, S., et al., "Bone morphogenic protein-7 (BMP-7), a novel therapy for diabetic nephropathy", Kidney International, vol. 63 (2003), pp. 2037-2049.
Wang, Shinong, et al., "Renal bone morphogenetic protein-7 protects against diabetic nephrophathy", Journal of the American Society of Nephrology, vol. 17, No. 9 (2006), pp. 2504-2512.

(Continued)

*Primary Examiner* — Michael C. Wilson
(74) *Attorney, Agent, or Firm* — Judy Jarecki-Black; Ruouins Chen

(57) ABSTRACT

The present invention relates to recombinant vectors expressing the BMP-7 polypeptide in host cells and to pharmaceutical compositions comprising such recombinant vectors. The invention also encompasses methods for prevention and/or treatment of both acute and chronic renal failure in mammals, advantageously in humans, dogs and cats, by intra-vascular kidney administration of the recombinant vectors and pharmaceutical compositions of the invention.

9 Claims, 7 Drawing Sheets

OTHER PUBLICATIONS

Zeisberg, Michael, "Bone morphogenic protein-7 and the kidney: current concepts and open questions", Nephrology Dialysis Transplantation, vol. 21, No. 3 (2006), pp. 568-573.

Zeisberg, M, et al., "Bone Morphogenic protein-7 induces mesenchymal to epithelial transition in adult renal fibroblasts and facilitates regeneration of injured kidney", J. Biol. Chem., vol. 280, No. 9 (2005), pp. 8094-8100.

Zeisberg, M, et al., et al., "Are there endogenous molecules that protect kidneys from injury? The case for bone morphogenic protein-7 (BMP-7)", Nephrol Dial Transplant, vol. 19 (2004), pp. 759-761.

Zhu, W., et al., "Combined bone morphogenetic protein-2 and -7 gene transfer enhances osteoblastic differentiation and spine fusion in a rodent model", www.JBMR-online.com, vol. 19, No. 12 (2004), p. 1-13.

\* cited by examiner

FIGURE 1: 050876pPCR-Script PLASMID MAP

FIGURE 2: pNB292 PLASMID MAP

Description of the plasmid pNB292:

Optimised canine BMP-7 gene: nucleotides 1651-2949

Kanamycine resistance gene (Tn903): nucleotides 4837-5652

CMV IE promoter: nucleotides 1-683

CMV IE 5' UTR: nucleotides 684-804

Intron A: nucleotides 805-1626 bGH transcriptional terminator / polyA: nucleotides 2979-3525

Origin of replication: nucleotides 3707-4214

Description of the plasmid pMEB038:

Optimised human BMP-7 gene: nucleotides 1668-2966

Kanamycine resistance gene (Tn903): nucleotides 4856-5668

CMV IE promoter: nucleotides 1-683

CMV IE 5' UTR: nucleotides 684-804

Intron A: nucleotides 805-1626 bGH transcriptional terminator / polyA: nucleotides 2995-3541

Origin of replication: nucleotides 3723-4230

Description of the plasmid pMEB039:

Optimised feline BMP-7 gene: nucleotides 1676-2974

Kanamycine resistance gene (Tn903): nucleotides 4870-5682

CMV IE promoter: nucleotides 1-683

CMV IE 5' UTR: nucleotides 684-804

Intron A: nucleotides 805-1626 bGH transcriptional terminator / polyA: nucleotides 3009-3555

Origin of replication: nucleotides 3737-4244

PLASMID ENCODING FELINE BMP-7

RELATED APPLICATIONS

This application is a continuation of U.S. Application Ser. No. 11/803,991 filed on May 16, 2007 now U.S. Pat. No. 7,771,995, which is a continuation-in-part of U.S. application Ser. No. 11/801,798 filed May 11, 2007 now abandoned which is a continuation in part of U.S. application Ser. No. 11/599,026, filed Nov. 14, 2006 now U.S. Pat. No. 7,598,364, and which claims priority to U.S. provisional application 60/736,452, filed Nov. 14, 2005.

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to recombinant vectors, to pharmaceutical compositions comprising such recombinant vectors, and to methods for prevention and/or treatment of acute and/or chronic renal failure in mammals. The invention also relates to vectors capable of expressing, in a host, a bioactive polypeptide belonging to the Osteogenic Protein-1/Bone Morphogenetic Protein-7 (OP-1/BMP-7) family of proteins. The invention also relates to intra-vascular kidney gene therapy with such vectors.

BACKGROUND OF THE INVENTION

The mammalian renal system serves primary roles both in the removal of catabolic waste products from the bloodstream and in the maintenance of fluid and electrolyte balances in the body. Renal failure is, therefore, a life-threatening condition in which the build-up of catabolites and other toxins, and/or the development of significant imbalances in electrolytes or fluids, may lead to the failure of other major organs systems and death. As a general matter, renal failure is classified as "acute" or "chronic". As detailed below, acute and chronic renal failure are debilitating and life-threatening diseases for which no adequate treatments exist to delay, and/or reverse kidney structural alterations associated with the disease.

Acute renal failure (ARF) is usually caused by an ischemic or toxic insult that results in an abrupt decline in renal functions. The kidneys are highly susceptible to ischemia and toxicants because of their unique anatomic and physiologic features. The large renal blood flow (approximately 25% of the cardiac output) results in increased delivery of blood-borne toxicants to the kidney as compared to other organs. The renal cortex is especially susceptible to toxicant exposure because it receives 90% of renal blood flow and has a large endothelial surface area due to the numerous glomerular capillaries. Within the renal cortex, the proximal tubule (the S3 segment or "pars recta") and the epithelial cells of the thick ascending arm of the loop of Henle, are most frequently affected by ischemic and toxicant-induced injury because of their solute transport functions and high metabolic rates. As water and electrolytes are reabsorbed from the glomerular filtrate, tubular epithelial cells can be exposed to increasingly high concentrations of toxicants. Similarly, in the medulla the counter-current multiplier system may concentrate toxicants. Toxicants that are either secreted or reabsorbed by tubular epithelial cells (such as gentamicin) may accumulate in high concentrations within these cells. Finally, the kidneys also play a role in the biotransformation of many drugs and toxicants. Biotransformation usually results in the formation of metabolites that are less toxic than the parent compound; however, in some cases (such as oxidation of ethylene glycol to glycolate and oxalate) the metabolites are more toxic.

ARF has three distinct phases, which are categorized as initiation, maintenance, and recovery. During the initiation phase, therapeutic measures that reduce the renal insult (e.g., fluid therapy) can prevent the development of established ARF. The maintenance phase is characterized by tubular lesions and established nephron dysfunction. The recovery phase of ARF occurs when renal function improves subsequent to nephron repair and compensatory hypertrophy. Tubular lesions may be repaired if the tubular basement membrane is intact and viable cells are present. In addition, functional and morphologic hypertrophy of surviving nephrons can, in some cases, adequately compensate for decreased nephron numbers. Even if renal functional recovery is incomplete, adequate function may be re-established in some cases. More commonly, however, tubular damage is severe and irreversible and a large percentage of animals die or are euthanized in the maintenance phase of ARF.

Despite tremendous efforts to decipher the cellular and molecular pathogenesis of ARF during the past decades, no effective treatment is currently available and the incidence of mortality remains very high in veterinary medicine. At least two retrospective studies have documented the poor prognosis associated with ARF in dogs. In a study of hospital acquired ARF, the survival rate was 38%, whereas in another study of all types of ARF, the survival rate was 24%. Thus, there is an un-met medical need for improved prevention and/or treatment of ARF.

Chronic renal failure (CRF) may be defined as progressive, permanent and significant reduction of glomerular filtration rate (GFR) due to significant and continuing loss of nephrons. CRF typically begins from a point at which a chronic renal insufficiency (i.e., a permanent decrease in renal function of at least 50-60%) has resulted from some insult to the renal tissues, which has caused a significant loss of nephron functional units. The initial insult may not have been associated with an episode of acute renal failure. Irrespective of the nature of the initial insult, CRF manifests a "final common path" of signs and symptoms as nephrons are progressively lost and GFR progressively declines. This progressive deterioration in renal function is slow and seemingly inevitable, typically spanning several months to years in canine and feline subjects and many decades in human patients.

The early stage of CRF typically begins when GFR has been reduced to approximately one-third of the normal level (e.g., 30-40 ml/min for an average human adult). As a result of the significant nephron loss, and in an apparent "attempt" to maintain the overall GFR with fewer nephrons, the average single nephron GFR (SNGFR) is increased by adaptation of the remaining nephrons at both the structural and functional levels. One structural manifestation of this adaptation that is readily detectable by microscopic examination of biopsy samples is a "compensatory hypertrophy" of both the glomeruli and the tubules of the kidney, a process that actually increases the volume of filtrate which can be produced by each remaining nephron by literal enlargement of the glomeruli and tubules.

As a result of the hypertrophy or dilatation of the collecting ducts, the urine of subjects with CRF often contains casts which are 2-6 times the normal diameter (referred to herein as "broad casts" or "renal failure casts". The presence of such broad casts aids in diagnosis of CRF. At the same time, there are functional changes in the remaining nephrons, such as decreased absorption or increased secretion of normally excreted solute, which may be responses to hormonal or paracrine changes elsewhere in the body (e.g., increasing levels of parathyroid hormone (PTH) in response to changes in serum levels of calcium and phosphate).

These adaptations in the early stage CRF are not successful in completely restoring GFR or other parameters of renal function and, in fact, subject the remaining nephrons to increased risk of loss. For example, the increased SNGFR is associated with mechanical stress on the glomerulus due to hypertension and hyperperfusion. The loss of integrity of podocyte junctures leads to increased permeability of the glomerulus to macromolecules or "leakiness" of the glomerular capsule. Proliferative effects are also observed in mesangial, epithelial and endothelial cells, as well as increases in the deposition of collagen and other matrix proteins. Sclerosis of both the glomeruli and tubules is another common symptom of the hypertrophied nephrons and the risk of coagulation in the glomerulus is increased. In particular, these adaptations of the remaining nephrons, by pushing the SNGFR well beyond its normal level, actually decrease the capacity of the remaining nephrons to respond to acute changes in water, solute, or acid loads, and therefore actually increase the probability of additional nephron loss.

As CRF progresses, and GFR continues to decline to less than 10% of normal (i.e., around 5-10 ml/min in humans), the subject enters into end-stage renal disease (ESRD). During this phase, the inability of the remaining nephrons to adequately remove waste products and maintain fluid and electrolyte balance, leads to a rapid decline in which many organ systems, and particularly the cardiovascular system, may begin to fail. At this point, renal failure will rapidly progress to death unless the patient receives renal replacement therapy (i.e., chronic hemodialysis, continuous peritoneal dialysis, or kidney transplantation).

The management of CRF must be conducted to ameliorate all identifiable clinical, metabolic, endocrine and biochemical consequences induced by renal failure including, but not limited to, azotemia, nutritional inadequacies, hypoproliferative anaemia, disordered mineral metabolism, electrolyte disturbances, metabolic acidosis, proteinuria, disordered water metabolism, systemic hypertension and the progression of renal injury through interstitial fibrosis that is considered to be the commonly converging outcome of CRF regardless of the specific etiology.

While tremendous progress has been made during the last decade to address several clinical, metabolic, endocrine and biochemical consequences of CRF, the therapy of clinically chronic fibrosis remains extremely challenging and therefore the long-term medical control of renal disease remains an important un-met therapeutic need. Currently, most advanced therapy targeting the reduction of renal disease-associated fibrosis is focused on the reduction of the activity of the renin-angiotensin system (RAS). Although this strategy has been shown to slow the disease evolution, its efficacy remains partial and it does not completely halt the progression of chronic fibrosis in experimental and clinical conditions. This is probably because many factors other than RAS contribute to the pathogenesis of CRF associated fibrosis.

The prevalence of CRF in cats and dogs is increasing. For every 1000 cats evaluated in 1980 in the US, four had renal failure regardless of age. By 1990, the number of reported cases of renal failure has quadrupled with 16 cases identified for every 1000 cats examined. For cats older than 15 years of age, 153 cases of renal failure were diagnosed in 1990 for every 1000 examinations. The increase in prevalence of renal failure in aging cats may reflect an increase in veterinary care sought by owners as well as greater efforts by veterinarians to detect the disease. Whatever the reason, these findings emphasize the emerging awareness and importance of CRF in older animals. The most frequent etiologies of CRF in companion animals include, but are not limited to, idiopathic chronic interstitial nephritis, irreversible ARF, familial renal dysplasia or aplasia, congenital polycystic kidney disease, amyloidosis, glomerulonephritis, hypercalcemia, bilateral hydronephrosis, leptospirosis, pyelonephritis, nephrolithiasis bilateral, Falconi-like syndrome, hypertension, renal lymphosarcoma.

In human medicine, approximately 600 patients per million receive chronic dialysis each year in the USA, at an average cost approaching $60,000-$80,000 per patient per year. Of the new cases of end-stage renal disease each year, approximately 28-33% are due to diabetic nephropathy (or diabetic glomerulopathy or diabetic renal hypertrophy), 24-29% are due to hypertensive nephrosclerosis (or hypertensive glomerulosclerosis), and 15-22% are due to glomerulonephritis. The 5-year survival rate for all chronic human dialysis patients is approximately 40%, but for patients over 65, the rate drops to approximately 20%. Therefore, a need remains for treatments to prevent the progressive loss of renal function which has caused almost 200,000 human patients in the USA alone to become dependent upon chronic dialysis, and which results in the premature deaths of tens of thousands each year.

In light of the fact that specific morphogens and/or growth factors that exhibit renotropic properties and promote tubular repair and recovery of renal function have been recently identified, it is conceivable that some of these molecules could have the potential to be used as therapeutic agents for the prevention and/or treatment of ARF and/or CRF. One such agent is Bone Morphogenetic Protein-7 (BMP-7, or Osteogenic Protein-1, OP-1), which is a member of the Transforming Growth Factor-β (TGF-β) superfamily. BMP-7 binds to activin receptors types I and II, but not to TGF-β receptors type I, II and III. Monomeric BMP-7 has a molecular weight of 17 to 19 kDa and was originally identified by its ability to induce ectopic bone formation. BMP-7 polypeptide is secreted as a homodimer with an apparent molecular weight of approximately 35-36 kDa. Recently, BMP-7 has been shown to be a key morphogen during nephrogenesis. Renal expression of BMP-7 continues in mature kidneys, especially in medullary collecting ducts. Renal tubules also express BMP-7 receptors. In animal models of ARF and CRF, renal expression of BMP-7 is significantly down-regulated and the administration of recombinant BMP-7 protein has been reported to accelerate renal recovery, an effect that was associated with less interstitial inflammation and programmed cell death.

However, because BMP-7 has a short half live in vivo (approximately 30 min), maintenance of a sustained level of exogenous protein in the circulation following injection of the purified protein requires multiple short-interval administrations, creating a very significant practical challenge. The cost of such a multi-injection therapy is too high to be applicable in veterinary medicine. Although gene delivery has been successfully promoted as an alternative to protein therapy for various diseases treatment, it's applicability for ARF and/or CRF prevention and/or treatment through BMP-7 polypeptide expression in vivo has not been proposed previously, and its potential effectiveness remains uncertain. Indeed, the low molecular weight of the BMP-7 homodimer (i.e., approximately 35 kDa) would theoretically allow for rapid glomerular filtration. Whether or not levels of BMP-7 expressed in vivo could reach therapeutically effective plasma concentrations cannot be predicted or determined from the existing literature. To further complicate the evaluation of in vivo-expressed BMP proteins, results can be variable depending on the immune status of the treated animal, with significant differences between immune competent and incompetent animals. Thus, when considered collectively as a whole, the literature does not teach whether levels of BMP-7 expressed in vivo could reach plasma concentrations that would be therapeutically useful.

Citation or identification of any document in this application does not constitute an admission that such document is available as prior art to the present invention.

SUMMARY OF THE INVENTION

The present invention is directed to methods of prevention and treatment of mammalian subjects who are suffering from, or who are at risk of, acute or chronic renal failure, and to recombinant vectors and pharmaceutical compositions for use in such methods. The methods, vectors and compositions of the invention are useful for reducing mortality and/or morbidity rates, and preventing, inhibiting, delaying, or alleviating the progressive loss of renal function which characterizes renal failure. Subjects for which the methods, recombinant vectors, and compositions of the present invention are useful include, but are not limited to, subjects already afflicted with acute or chronic renal failure, subjects who have already received renal replacement therapy, as well as any subject reasonably expected to suffer from an acute or progressive loss of renal function associated with progressive loss of functioning nephron units. Whether a particular subject is at risk of renal disease, and/or whether a subject may benefit from the methods and/or compositions of the present invention, is a determination that can be routinely made by one of ordinary skill in the relevant medical or veterinary art.

In one embodiment the present invention relates to a vector containing and expressing in a host a pre-pro BMP-7 gene, a proBMP-7 gene or a mature BMP-7 gene. The BMP-7 gene encoding the pre-proBMP-7 polypeptide, the proBMP-7 polypeptide or the mature BMP-7 polypeptide may originate from a mammal. In a preferred embodiment, the expression vector may comprise a polynucleotide that encodes a canine pre-proBMP-7, a canine pro-BMP-7 or a canine mature BMP-7 polypeptide. In another preferred embodiment, the expression vector may comprise a polynucleotide that encodes a feline pre-proBMP-7, a feline pro-BMP-7 or a feline mature BMP-7 polypeptide. In another preferred embodiment, the expression vector may comprise a polynucleotide that encodes a human pre-proBMP-7, a human pro-BMP-7 or a human mature BMP-7 polypeptide. The polynucleotide encoding the BMP-7 polypeptide may be operatively linked to a promoter and optionally to an enhancer.

In an advantageous embodiment, the invention relates to a vector containing and expressing the canine proBMP-7 polypeptide, wherein the canine proBMP-7 polypeptide is deleted of the "pre" peptide at the N-terminus, and wherein a peptide signal sequence from a different origin is fused to the canine proBMP-7 polypeptide. In another advantageous embodiment, the invention relates to a vector containing and expressing the feline proBMP-7 polypeptide, wherein the feline proBMP-7 polypeptide is deleted of the "pre" peptide at the N-terminus, and wherein a peptide signal sequence from a different origin is fused to the feline proBMP-7 polypeptide. In another advantageous embodiment, the invention relates to a vector containing and expressing the human proBMP-7 polypeptide, wherein the human proBMP-7 polypeptide is deleted of the "pre" peptide at the N-terminus, and wherein a peptide signal sequence from a different origin is fused to the human proBMP-7 polypeptide. Advantageously, the peptide signal sequence may be the insulin-like growth factor 1 (IGF-1) or the tissue plasminogen activator (tPA) peptide signal sequence. In another embodiment, the expression vector may comprise a polynucleotide that encodes a canine mature BMP-7 polypeptide wherein said polypeptide is fused with a peptide signal sequence from BMP-7, IGF-1 or tPA. In another embodiment, the expression vector may comprise a polynucleotide that encodes a feline mature BMP-7 polypeptide wherein said polypeptide is fused with a peptide signal sequence from BMP-7, IGF-1 or tPA. In another embodiment, the expression vector may comprise a polynucleotide that encodes a human mature BMP-7 polypeptide wherein said polypeptide is fused with a peptide signal sequence from BMP-7, IGF-1 or tPA.

In another embodiment the invention relates to a pharmaceutical composition comprising a vector expressing a pre-proBMP-7 polypeptide, a proBMP-7 polypeptide or a mature BMP-7 polypeptide and a pharmaceutically or veterinarily acceptable carrier, excipient or vehicle. In a particular embodiment, the pharmaceutical composition may comprise a substance to improve the efficacy of transfection or transduction of the vector into the host cells.

In yet another embodiment the invention relates to a method for delivering the BMP-7 polypeptide to a mammal which may comprise injecting a vector capable of expressing, in vivo, a pre-proBMP-7 polypeptide, a proBMP-7 polypeptide or a mature BMP-7 polypeptide. In an advantageous embodiment, the animal host may be a dog or a cat. The invention relates to the use of such a vector to prevent and/or treat a mammal for chronic or acute renal failure. The pharmaceutical compositions of the invention may be administered by any suitable route of administration including, but not limited to, by the intramuscular, subcutaneous route or intravascular route. In a particular embodiment the vector may be administered to the host using a needle-free injector or using electrotransfer.

In yet another embodiment the invention relates to a method for delivering the BMP-7 polypeptide to a mammal which may comprise injecting intra-vascularly into the renal vein a plasmid capable of expressing, in vivo, a pre-proBMP-7 polypeptide, a proBMP-7 polypeptide or a mature BMP-7 polypeptide. In an advantageous embodiment, the mammal host may be a human, a canine animal or a feline animal, notably man, woman, child, dog, bitch, puppy or cat, kitten. The invention relates to the use of such a plasmid to prevent and/or treat a mammal for chronic or acute renal failure. In a particular embodiment the vector may be administered to the mammal host using hemodynamic retrograde injection into the renal vein, notably using a non invasive interventionist catheter. By definition, hemodynamic means a rapid injection of a large volume.

In a further embodiment the invention relates to the use of pharmaceutical compositions according to the present invention to treat mammals exhibiting an increase in serum creatinine concentration and/or an increase in serum urea nitrogen concentration. Advantageously a cat may be treated when the plasma creatinine concentration is higher than 1.9 mg/dl and/or when the plasma urea nitrogen concentration is higher than 35 mg/dl. Advantageously a dog may be treated when the plasma creatinine concentration is higher than 1.6 mg/dl, and/or when the plasma urea nitrogen concentration is higher than 30 mg/dl. Advantageously a human may be treated when the presence of a functional or structural renal abnormality that evolved over more than 3 months (this can be a morphological abnormality provided it is clinically significant or a histological abnormality or a modification of blood and/or urina composition secondary to a renal insult) and/or when the Glomerular Filtration Rate (GRF) is below 60 ml/min/ 1.73 m² over more than 3 month.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are described in, or are obvious from and encompassed by, the following Detailed Description.

BRIEF DESCRIPTION OF THE DRAWINGS

The following detailed description, given by way of example but not intended to limit the invention solely to the specific embodiments described, may best be understood in conjunction with the accompanying drawings, in which.

Figure 1:
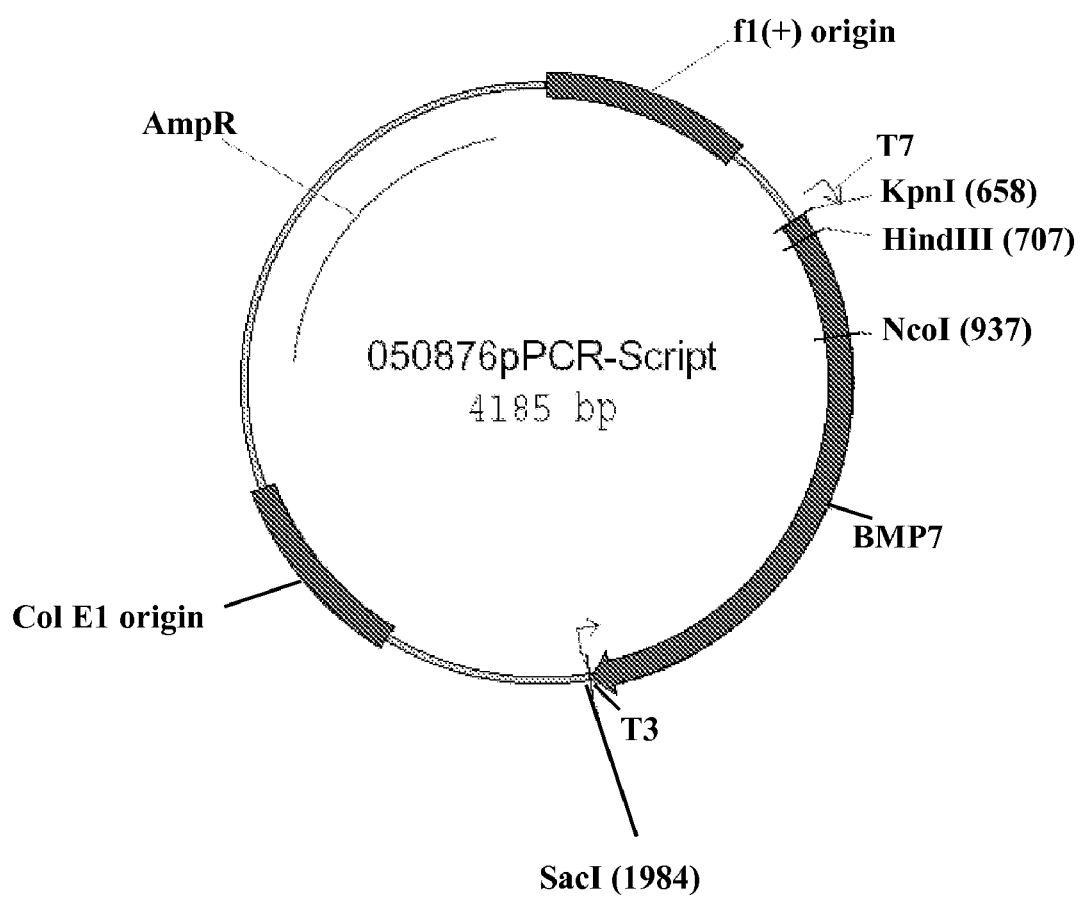
FIG. 1 depicts the 050876pPCR-Script plasmid map and the encoded open reading frame ("ORF") of the canine BMP-7. The nucleotide sequence of the encoded ORF is that of SEQ ID NO: 2 and the amino acid sequence of the encoded ORF is that of SEQ ID NO: 3.

Also included as part of the present application is a sequence listing in which: SEQ ID NO: 1 is the nucleotide sequence of the canine pre-proBMP-7 polypeptide, SEQ ID NO: 2 is the codon-optimized nucleotide sequence of the canine pre-proBMP-7 polypeptide, SEQ ID NO: 3 is the amino acid sequence of the canine pre-proBMP-7 polypeptide, SEQ ID NO: 4 is the nucleotide sequence of the short signal peptide from tPA (23 amino acids), SEQ ID NO: 5 is the amino acid sequence of the short signal peptide from tPA (23 amino acids), SEQ ID NO: 6 is the nucleotide sequence of the long signal peptide from tPA (28 amino acids), SEQ ID NO: 7 is the amino acid sequence of the long signal peptide from tPA (28 amino acids), SEQ ID NO: 8 is the nucleotide sequence of the equine IGF-1 signal peptide, SEQ ID NO: 9 is the amino acid sequence of the equine IGF-1 signal peptide, SEQ ID NO: 10 is the nucleotide sequence of the pNB292 plasmid, SEQ ID NO: 11 is the nucleotide sequence of the canine IGF-1 signal peptide, SEQ ID NO: 12 is the amino acid sequence of the canine IGF-1 signal peptide, SEQ ID NO: 13 is the nucleotide sequence of the human pre-proBMP-7 polypeptide, SEQ ID NO: 14 is the codon-optimized nucleotide sequence of the human pre-proBMP-7 polypeptide, SEQ ID NO: 15 is the amino acid sequence of the human pre-proBMP-7 polypeptide, SEQ ID NO: 16 is the nucleotide sequence of the pMEB038 plasmid, SEQ ID NO: 17 is the nucleotide sequence of the feline pre-proBMP-7 polypeptide, SEQ ID NO: 18 is the codon-optimized nucleotide sequence of the feline pre-proBMP-7 polypeptide, SEQ ID NO: 19 is the amino acid sequence of the feline pre-proBMP-7 polypeptide, and SEQ ID NO: 20 is the nucleotide sequence of the pMEB039 plasmid.

DETAILED DESCRIPTION

The methods and compositions of the present invention can be used for preventative treatment of renal failure. The terms "prevention", "prophylaxis", "preventative treatment" and "prophylactic treatment", as they relate to renal failure, and as they are used herein and in the field of human and veterinary medicine, relate to the treatment of either healthy animals or animals suffering from an unrelated disease, but who are considered to be at risk of acute renal failure. The main risk factors for acute renal failure in cats and dogs include, but are not limited to, shock and/or hypovolemia (for example haemorrhage, hypotensive shock, septic shock, prolonged or deep anaesthesia, hypovolemia, heat stroke, trauma, burns, or diuretic abuse), systemic diseases (for example pancreatis, peritonitis, hepatic failure, disseminated intravascular coagulation, adrenal insufficiency or vasculitis), ischemia (as caused by, for example, thromboembolic occlusion or malignant hypertension), infections (for example leptospirosis, pyelonephritis, feline infectious peritonitis, borreliosis, leishmaniasis, babesiosis, septicaemia or septic emboli), systemic renal disease (for example multiple organ failure, glomerulonephritis, systemic lupus erythematosus, renal vein thrombosis, urinary outflow obstruction, haemolytic uremic syndrome, hemepigmenturia-crush syndrome or polycythemia), advanced age, congenital and/or genetic renal diseases, and other miscellaneous factors such as exposure to nephrotoxins (for example aminoglycosides, amphotericin B, cisplatin, adriamycin, non steroidal anti-inflammatory drugs, diuretics, IL-2 or allopurinol), neoplasia (for example lymphoma), hypercalcemia, trauma (for example avulsions), malignant hypertension, oxalate nephrosis, and the like.

Treatment for preventative purposes is generally conducted within a few days (ideally with 6 to 8 days) before the exposure of a healthy animal to one or more of the aforementioned risk factors for acute renal failure. Alternatively, in diseased animals for which an associated risk factor for acute renal failure has been identified, treatment may be conducted as quickly as possible to limit any negative impact of the primary disease of risk factor on the kidney metabolism and/or the structure and organization of the kidney tissue.

In addition to preventative treatments, the methods and compositions of the present invention can also be used for therapeutic treatment of renal failure. The terms "therapy" or "therapeutic treatment", as they relate to renal failure, and as they are used herein and in the field of veterinary medicine, relate to treating, or supporting and/or accelerating treatment of, animals that are already suffering from, or are recovering from (i.e., are in the recovery phase) acute renal failure, or treatments aimed at slowing down and/or reversing lesion evolution in animals diagnosed as having, or at being at risk of, chronic renal failure. A critical objective of therapy is to reduce the risk of an evolution towards CRF subsequent to an ARF event. As used herein, a subject is said to suffer from CRF, or be at risk of developing CRF, if the subject is reasonably expected to suffer a progressive loss of renal function associated with progressive loss of functioning nephron units. Whether a particular subject suffers of CRF, or is at risk of developing CRF, can readily be determined by one with ordinary skill in the relevant veterinary or medical art.

The main risks factors for chronic renal failure in dogs include, but are not limited to, idiopathic chronic interstitial nephritis, irreversible ARF, familial renal dysplasia or aplasia (high risk breeds include Norwegian elkhounds, Lhasa apso, Samoyed, Cocker spaniel, Doberman pinsher, Standard poodle, and Golden retriever), congenital polycystic kidney disease (for example in Cairn terriers), amyloidosis, glomerulonephritis, hypercalcemia, bilateral hydronephrosis, leptospirosis, pyelonephritis, nephrolithiasis bilateral, Falconi-like syndrome, and hypertension.

The main risk factors for chronic renal failure in cats include, but are not limited to, idiopathic chronic interstitial nephritis, irreversible ARF, renal lymphosarcoma, polycystic kidney disease (for example in familial in Persian cats), glomerulonephritis, bilateral hydronephrosis, amyloidosis, pyelonephritis, hypercalcemia, and bilateral nephrolithiasis.

Human subjects suffering from CRF, or whom are at risk of developing CRF, or who may be in need of renal replacement therapy, include, but are not limited to, subjects with end-stage renal disease, chronic diabetes nephropathy, hypertensive nephrosclerosis, chronic glomerulonephritis, hereditary nephritis, and/or renal dysplasia, subjects who have had a biopsy indicating glomerular hypertrophy, tubular hypertrophy, chronic glomerulosclerosis, and/or chronic tubulo-interstitial sclerosis, subjects who have had an ultrasound, MRI, CAT scan, or other non-invasive examination indicating the presence of renal fibrosis, subjects having an unusual number of broad casts present in their urinary sediment, subjects having a glomerular filtration rate ("GFR") which is chronically less than 50%, and more particularly less than about 40%, 30% or 20%, of the expected GFR for the subject, subjects possessing a number of functional nephron units which is less than about 50%, and more particularly less than about 40%, 30% or 20% of the number of functional nephron units possessed by a healthy but otherwise similar subject, subjects with only a single kidney, and subjects that are kidney transplant recipients.

The "glomerular filtration rate" or "GFR" is proportional to the rate of clearance into the urine of "marker" substance which is a plasma-borne substance which is not bound by serum proteins, is freely filtered across glomeruli, and is neither secreted nor reabsorbed by the renal tubules. Thus, as used herein, GFR preferably is defined by the following equation:

$$GFR = \frac{U_{conc} \times V}{P_{conc}}$$

where $U_{conc}$ is the urine concentration of the marker substance, $P_{conc}$ is plasma concentration of the marker substance, and V is the urine flow rate in ml/min. Optionally, the GFR can be corrected for body surface area. Thus, the GFR values may be regarded as being in units of ml/min/1.73 m$^2$". The preferred marker substance for GFR measurements is inulin, however, because of difficulties in measuring the concentration of this substance, creatinine is typically used as the marker for GFR measurements in clinical settings.

An estimate of the "expected GFR" or "$GFR_{exp}$" may be provided based upon considerations of a subject's age, weight, sex, body surface area, and degree of musculature, and the plasma concentration of some marker compound (e.g., creatinine) as determined by a blood test. Thus, as an example, an expected GFR may be estimated as:

$$GFR_{exp} \approx \frac{(140-age) \times weight\ (kg)}{72 \times P_{conc}(mg/dL))}$$

This estimate does not take into consideration such factors as surface area, degree of musculature, or percentage of body fat. Nonetheless, using plasma creatinine levels as the marker, this formula has been employed for human males as an inexpensive means of estimating GFR. Because creatinine is produced by striated muscles, the expected GFR of human females subjects is estimated by the same equation multiplied by 0.85 to account for expected difference in muscle mass (see Lemann et al., 1990 Am. J. Kidney Dis. 16(3); 236-243).

Microscopic examination of urinary sediment for the presence of formed elements is a standard procedure in urine analysis. Amongst the formed elements which may be present in urine, are cylindrical masses of agglutinated materials that typically represent a mold or "cast" of the lumen of a distal convoluted tubule or collecting tube. In healthy human beings, such casts typically have a diameter of 15-25 μm. In subjects with CRF, however, hypertrophy of the tubules may result in the presence of casts which are 2-6 times the diameter of normal casts and often have a homogeneous waxy appearance. These are referred to as "broad casts" or "renal failure casts". As used herein, the term "broad cast" is used to refer to urinary sediment casts having a diameter of 2-6 times normal for the subject, or about 30-150 μm for human casts.

As used herein with respect to clinical indications the term "acute" is used to refer to renal pathologies for which onset occurs rapidly, typically within hours or days of exposure to an insult or risk factor.

As used herein with respect to clinical indications the term "chronic" means persisting for a period of at least three, and more preferably, at least six months. Thus, for example, a subject with a measured GFR chronically below 50% of $GFR_{exp}$ is a subject in which the GFR has been measured and found to be below 50% of $GFR_{exp}$ in at least two measurements separated by at least three, and more preferably, by at least six months, and for which there is no medically sound reason to believe that GFR was substantially (e.g., 10%) higher during the intervening period. Other indicators of abnormal renal function, such as the presence of broad casts, could similarly be described as chronic if the presence of such indicators persisted in at least two measurements separated by at least three, and more preferably, by at least six months.

Table 1 lists some, but not all, of the parameters that may be useful in differentiating between ARF and CRF.

TABLE 1

Parameters Useful for Differentiating between ARF and CRF

| | Acute Renal Failure (ARF) | Chronic Renal Failure (CRF) |
|---|---|---|
| History | Ischemic or toxicant exposure | Previous renal disease or renal insufficiency<br>Longstanding polydipsia/polyuria<br>Chronic weight loss, vomiting, diarrhoea |
| Physical Examination | Good body condition<br>Smooth, swollen, painful kidneys<br>Relatively severe clinical signs for level of dysfunction (azotemia) | Poor body condition<br>Small, irregular kidneys<br>Relatively mild clinical signs for level of dysfunction (azotemia)<br>Osteodystrophy |
| Clinicopathologic findings | Normal or increased hematocrit<br>Active urine sediment<br>Normal to increased serum potassium<br>More severe metabolic acidosis | Non regenerative anemia<br>Inactive urine sediment<br>Normal to low serum potassium<br>Less severe metabolic acidosis |

The present invention provides therapies and preventative treatments for renal failure that utilize pharmaceutical compositions comprising vectors capable of expressing the BMP-7 polypeptide in vivo and methods and composition for inducing a sustained increase in plasma BMP-7 concentration and thereby reducing the activation of the TGF-β pathway on epithelial cells. TGF-β activation triggers, amongst other things, the phosphorylation of Smad2 and Smad3 factors and their nuclear import, leading to the promotion of epithelial-mesenchymal transition and to the repression of mesenchymal-epithelial transition, and acting as key trigger for fibrosis. Although BMP-7 is expressed in adult kidneys, its expression is frequently down regulated in the face of renal failure. Therefore, exogenous in vivo-produced BMP-7 can help restore levels of BMP-7 to normal physiological levels, leading to the control and regression of the fibrosis associated with tubulo-interstitial nephritis and CRF.

As used herein, a pharmaceutical composition according to the invention is said to have "therapeutic efficacy", or to be "therapeutically effective", if administration of that amount of the composition is sufficient to cause a significant improvement of the clinical signs or measurable markers of the disease in a mammalian subject suffering from ARF or CRF. As used herein, a pharmaceutical composition according to the invention is said to have "prophylactic efficacy" or to be "an effective", if administration of that amount of the composition is sufficient to prevent the development of ARF in a subject. The term "therapeutically effective" may also be used herein, in a more general sense, to refer to an amount of a composition that is either sufficient to cause a significant improvement of the clinical signs or measurable markers of disease in a mammalian subject suffering from ARF or CRF, or that is sufficient to prevent the development of ARF in a subject.

Measurable markers of renal function, which are also useful in evaluating the ARF or CRF status of a subject, are well known in the medical and veterinary literature and to those of skill in the art, and include, but are not limited to, blood urea nitrogen or "BUN" levels (both static measurements and measurements of rates of increase or decrease in BUN levels), serum creatinine levels (both static measurements and measurements of rates of increase or decrease in serum creatinine levels), measurements of the BUN/creatinine ratio (static measurements of measurements of the rate of change of the BUN/creatinine ratio), urine/plasma ratios for creatinine, urine/plasma ratios for urea, glomerular filtration rates (GFR), serum concentrations of sodium (Na+), urine osmolarity, daily urine output, and the like (see, for example, Brenner and Lazarus (1994), in Harrison's principles of internal medicine, 13$^{th}$ edition, Isselbacher et al. eds, McGraw Hill Text, NY; Luke and Strom (1994), in Internal Medicine, 4$^{th}$ Edition, J. H. Stein, ed., Mosby-Year Book, Inc. St Louis). Of the above, measurements of the plasma concentrations of creatinine and/or urea or BUN are particularly important and useful readouts of renal function.

Normal values for serum creatinine concentrations range from about 0.5 to about 1.6 mg/deciliter ("dl") in dogs and from about 0.5 to about 1.9 mg/dl in cats. The upper limit of the normal physiological range of serum creatinine levels is slightly higher in cats than in dogs. With the exception of diet, factors influencing physiological values of serum creatinine concentration are poorly understood. It is known that a diet rich in protein has the potential to cause transient hypercreatinemia. For example, an increase of around 25% in serum creatinine concentration can occur over a 6-9 hour period when healthy dogs are fed with commercial food. The relevance of minor variations of creatinemia may be difficult to interpret, however the smallest relevant variation between two successive measurements of creatinine levels is considered to be a change in concentration of 35 µmol/l from normal values.

The upper limit of the normal physiological range for BUN levels in fasting dogs and cats ranges from about 8.8 to about 25.9 mg/dl in dogs, and from about 15.4 to about 31.2 mg/dl in cats—the upper limits of the normal range are slightly higher in cats than in dogs. BUN levels, like creatinine levels, are influenced by diet. Other factors that can lead to variation in BUN levels include long-term glucocorticoide treatment and/or hepatocellular failure.

Any significant increase of serum creatinine levels and/or BUN levels above their normal physiological ranges is a sign of a reduced ability of the kidneys to eliminate waste and catabolites (i.e., excretory failure).

Experimental demonstration of the efficacy of the methods and compositions of the present invention (e.g. the. methods and compositions useful for gene therapy with BMP-7 or functional equivalents of BMP-7), can be performed by performed in a variety of ways, for example, by demonstrating that animals treated using the methods and compositions of the present invention exhibit a significantly reduced elevation of plasma creatinine and/or BUN, as compared to placebo-treated animals, when exposed to a trigger or risk factor such as, for example, a toxicant (e.g., glycerol, HgCl$_2$) or a procedure that induces renal ischemia (e.g., bilateral renal arteries occlusion).

Similarly, tissue readouts can be used to demonstrate the efficacy of the methods and compositions of the present invention. Examples of suitable tissular readouts include the quantification of tubulo-interstitial nephritic lesions ("TIN" lesions) within the cortical parenchyma of the kidney, and to a lesser extent, within the medullary parenchyma of the kidney. It is well documented that renal interstitial fibrosis associated with tubulo-interstitial nephritis (TIN) is a common final pathway of kidney disorders with a wide spectrum of diverse etiologies. Deterioration of renal function is largely determined by the extent of the tubulo-interstitial lesions in many forms of renal diseases, and also in several experimental animal models. Accordingly, methods or compositions that are able to slow down or reverse the evolution of TIN fibrosis have the potential to benefit all kidney disorders through a disease-modifying mechanism (i.e., by limiting the degradation and disorganization of the structural elements of kidney tissues). Experimental demonstration of the efficacy of the BMP-7 gene therapy methods and compositions of the present invention can be demonstrated from the observation that BMP-7-treated animals have significantly reduced tubulo-interstitial lesions in the kidneys than controls as assessed using the unilateral ureteral obstruction or "UUO" model. The UUO model is a well-established animal model of chronic progression of renal fibrosis associated with progressive tubular atrophy and interstitial collagen accumulation. The UUO model is well known in art (see for example, R. Chevalier et al., Kidney Int. 2000, 57, 882-890, the contents of which are hereby incorporated by reference in their entirety), and the unilateral ureteral obstruction procedure can be readily performed by those of ordinary skill in the art. The UUO model is typically associated with very significant tubulo-interstitial pathology and with minimal glomerular lesions, and is a relevant and useful experimental model for demonstrating the efficacy of the methods and compositions of the present invention, for example the demonstrating the efficacy of the gene therapy strategy disclosed herein which is based on the in vivo expression of BMP-7 or functional equivalents of BMP-7. Using this model, the evaluation of TIN in the renal cortex can be determined using conventional hematoxylin and eosin (or "H&E") staining and/or collagen-specific Masson Trichrome staining of fixed tissues. Characterization of the lesions is based on the extent of tubular dilatation, epithelial atrophy, and interstitial expansion with myofibroblast activation and matrix deposition. Additional investigations can be based on immunohistochemistry and histomorphometry techniques using, for example, α-smooth muscle actin ("α-SMA") specific antibodies to characterize and quantify the level of epithelial to mesenchyme transition (or "EMT") in the tissue. Complementary immunohistochemical analysis can also be performed with antibodies specific for collagen I or for fibronectin. Quantification of cellular infiltration is an additional readout that can be used to characterize the lesions. Immunohistochemical analysis of the latter can be conducted using, for example, anti ED-1 or anti mac-1 antibodies that are specific for macrophages. Collectively, the results of the above readouts can be used to provide a grade for the lesion.

In addition to the above, any other suitable methods or readouts for studying kidney disease and/or kidney function, including any other suitable animal models, can also be used to demonstrate the efficacy of the methods and compositions of the present invention, and to determine what amount of such compositions, or what modes of administration, will be therapeutically or an effective amount.

In one aspect, the present invention relates to a vector capable of expressing, in vivo in a host, a Bone Morphogenetic Protein-7 (BMP-7) polypeptide, or a variant or a fragment thereof. As used herein "BMP-7 polypeptide" may be used to refer to pre-pro, pro or mature BMP-7 polypeptides, wherein the pro and mature BMP-7 polypeptides may be fused to a BMP-7, IGF-1 or tPA signal peptide. The BMP-7 polypeptides of the present invention are preferably of canine, feline or human origin. In one embodiment the vector may contain and express in the host a pre-proBMP-7, a proBMP-7 or a mature BMP-7 nucleotide sequence or gene. The nucleotide sequence or gene encoding the pre-proBMP-7 polypeptide, the proBMP-7 polypeptide or the mature BMP-7 polypeptide may originate from a mammal, for example a human, a cat or a dog. In a preferred embodiment the BMP-7 nucleotide sequence or gene may originate from a dog. In another preferred embodiment the BMP-7 nucleotide sequence or gene may originate from a cat. In another preferred embodiment the BMP-7 nucleotide sequence or gene may originate from a human.

BMP-7 is also known as Osteogenic Protein-1 or "OP-1", and is a member of the transforming growth factor-β or "TGF-β" superfamily. It is a secreted protein that is processed from the pro-protein to yield the carboxy-terminal mature protein. Within the mature protein there is a conserved pattern of seven cysteine residues defining a domain that extends from amino acid 330 to amino acid 430 of SEQ ID NO: 3, SEQ ID NO: 15 and SEQ ID NO: 19. The active form of the protein is a disulfide-bonded homodimer. In its mature, native form, naturally occurring BMP-7 is a glycosylated dimer having an apparent molecular weight of about 30-36 kDa, as determined by SDS-polyacrylamide gel electrophoresis ("SDS-PAGE"). When reduced, the 30 kDa protein gives rise to two glycosylated polypeptide subunits having apparent molecular weights of about 16 kDa and 18 kDa. The unglycosylated protein has an apparent molecular weight of about 27 kDa. When reduced, the 27 kDa unglycosylated protein gives rise to two unglycosylated polypeptide chains, having molecular weights of about 14 kDa and 16 kDa.

Typically, the naturally occurring BMP-7 protein is translated as a precursor, having an N-terminal signal peptide sequence, a "pro" domain, and a "mature" protein domain. The signal peptide is 29 residues long and is cleaved off rapidly upon translation at a cleavage site that can be predicted using the method of Von Heijne (1986), Nucleic Acid Research, 14; 4683-4691. The "pro" domain has 264 residues in human, canine, feline, swine and bovine BMP-7, and 263 residues in mouse BMP-7. The pro domain is cleaved to yield the "mature" C-terminal domain of 139 residues, which includes the conserved seven-cysteine C-terminal domain of 102 residues. As referred to herein, the "pro form" of the BMP-7 polypeptide refers to a protein comprising a pair of polypeptides, each comprising a pro domain in either covalent or non-covalent association with the mature domain of the BMP-7 polypeptide. The pro form appears to be the primary form secreted from cultured mammalian cells. The "mature form" of the protein refers to the mature C-terminal domain which is not associated, either covalently or non-covalently, with the pro domain.

As used herein the terms "pre-pro BMP-7", "pro BMP-7", "mature BMP-7" and "BMP-7 refer not only to the specific polypeptides and sequences illustrated in the specification and in the accompanying sequence listing, but also refer to any and all of the known naturally occurring variants, of these proteins including, but not limited to, derivatives, mutants, homologues, orthologs, allelic variants, allelic polymorphs, polymorphic variants, phylogenetic counterparts, and also any and all non-naturally occurring variants of these proteins, including but not limited to derivatives, mutants, fragments, fusion proteins, and the like. As used herein, the term "variant" encompasses all such naturally occurring and non-naturally occurring variants. In particular, the present invention encompasses all such variants that retain the feature of being useful for the therapeutic or prophylactic treatment of renal diseases including ARF and CRF, and/or that retain BMP-7 activity.

These functionally equivalent variants, derivatives, and fragments, and the like display the ability to retain BMP-7 activity. A functional equivalent, as used herein, refers to any BMP-7 variants, derivatives, fragments, and the like that meet either of the following two criteria (a) they have a significant level of amino acid sequence homology with the protein sequence of BMP-7 as described herein, or is encoded by a nucleotide that has a significant level of nucleotide sequence homology with the protein sequence of BMP-7 as described herein; or (b) they have the ability to provide a statistically different response in the treated group as compared to a placebo treated group in at least one of the following experimental models of renal failure in rodents: (i) a toxicant-induced or ischemia-induced renal failure model, where reduced elevation of plasma creatinine or BUN is expected in the treated as compared to the control/placebo group; (ii) a UUO model of renal failure, where reduced lesion grading is expected in the treated group as compared to the control/placebo group.

By way of illustration of variants, derivatives, and the like that may be encompassed by the present invention include, but are not limited to, BMP-7 variants, derivatives, and the like that are encoded by nucleotide sequences that are not exactly the same as the nucleotide sequences disclosed herein, but wherein the changes in the nucleotide sequences do not change the encoded amino acid sequence, or result in conservative substitutions of amino acid residues, deletion of addition of one or a few amino acids, substitution of amino acid residues by amino acid analogues that do not significantly affect the properties of the encoded polypeptides, and the like. Examples of conservative amino acid substitutions include glycine/alanine substitutions; valine/isoleucine/leucine substitutions; asparagine/glutamine substitutions; aspartic acid/glutamic acid substitutions; serine/threonine/methionine substitutions; lysine/arginine substitutions; and phenylalanine/tyrosine/tryptophan substitutions. Other types of substitutions, variations, additions, deletions and derivatives that result in functional BMP-7 derivatives, as described above, are also encompassed by the present invention, and one of skill in the art would readily know how to make, identify, or select such variants or derivatives, and how to test for BMP-7 activity of those variants or derivatives. One of skill in the art may optimize the expression of the BMP-7 polypeptides of the invention by removing cryptic splice sites, by adapting the codon usage by introducing a Kozak consensus sequence before the start codon, by changing the codon usage or combination thereof to improve expression.

In another embodiment, the present invention may comprise a canine pre-proBMP-7 polypeptide variant having at least 90%, at least 91%, at least 92%, at least 93%, at least 94%, at least 95%, at least 96%, at least 97%, at least 98% or at least 99% homology or identity with residues 1 to 431 of SEQ ID NO: 3.

In another embodiment, the present invention may comprise a human pre-proBMP-7 polypeptide variant having at least 90%, at least 91%, at least 92%, at least 93%, at least 94%, at least 95%, at least 96%, at least 97%, at least 98% or at least 99% homology or identity with residues 1 to 431 of SEQ ID NO: 15.

In another embodiment, the present invention may comprise a feline pre-proBMP-7 polypeptide variant having at least 90%, at least 91%, at least 92%, at least 93%, at least 94%, at least 95%, at least 96%, at least 97%, at least 98% or at least 99% homology or identity with residues 1 to 431 of SEQ ID NO: 19.

In another embodiment the invention may comprise a canine mature BMP-7 polypeptide variant having at least 97%, at least 97.5%, at least 98%, at least 98.5%, or at least 99% homology or identity with residues 293 to residue 431 of SEQ ID NO: 3.

In another embodiment the invention may comprise a human mature BMP-7 polypeptide variant having at least 97%, at least 97.5%, at least 98%, at least 98.5%, or at least 99% homology or identity with residues 293 to residue 431 of SEQ ID NO: 15.

In another embodiment the invention may comprise a feline mature BMP-7 polypeptide variant having at least 97%, at least 97.5%, at least 98%, at least 98.5%, or at least 99% homology or identity with residues 293 to residue 431 of SEQ ID NO: 19.

For the purposes of the present invention, sequence identity or homology may be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA 1990, 87, 2264-2268, modified as in Karlin & Altschul, Proc. Natl. Acad. Sci. USA 1993, 90, 5873-5877.

Another example of a mathematical algorithm used for comparison of sequences is the algorithm of Myers & Miller, CABIOS 1988, 4, 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988, 85, 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266, 460-480; Altschul et al., Journal of Molecular Biology 1990, 215, 403-410; Gish & States, Nature Genetics, 1993, 3: 266-272; Karlin & Altschul, 1993, Proc. Natl. Acad. Sci. USA 90, 5873-5877; all of which are incorporated by reference herein).

In general, comparison of amino acid sequences may be accomplished by aligning an amino acid sequence of a polypeptide of a known structure with the amino acid sequence of a the polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

In all search programs in the suite, the gapped alignment routines are integral to the database search itself Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

In a preferred embodiment, the present invention provides a vector that contains and expresses a polynucleotide encoding a canine pre-proBMP-7 polypeptide, and more preferably that contains and expresses nucleotides 1 to 1296 of SEQ ID NO: 1. Preferably this vector expresses a polypeptide having the amino acid sequence of SEQ ID NO: 3.

In another preferred embodiment, the present invention provides a vector that contains and expresses a polynucleotide encoding a human pre-proBMP-7 polypeptide, and more preferably that contains and expresses nucleotides 1 to 1296 of SEQ ID NO: 13. Preferably this vector expresses a polypeptide having the amino acid sequence of SEQ ID NO: 15.

In another preferred embodiment, the present invention provides a vector that contains and expresses a polynucleotide encoding a feline pre-proBMP-7 polypeptide, and more preferably that contains and expresses nucleotides 1 to 1296 of SEQ ID NO: 17. Preferably this vector expresses a polypeptide having the amino acid sequence of SEQ ID NO: 19.

In one embodiment, the peptide signal (prepeptide) sequence spans from the Met residue at position (1) to the Ala residue at position (29), with the numbering of the amino acid residues being that of the pre-proBMP-7 sequence identified as SEQ ID NO: 3, 15 or 19. Cleavage of the signal peptide may occur after the Ala(29) residue. After cleavage of the preBMP-7 peptide, the proBMP-7 polypeptide is secondarily cleaved after the sequence Arg-X-X-Arg(292) to lead to the mature BMP-7 polypeptide.

The terms "protein", "polypeptide" and "polypeptide fragment" are used interchangeably herein to refer to polymers of amino acid residues of any length.

In certain embodiments, the expression vector may comprise a polynucleotide that encodes a mature BMP-7 polypeptide, wherein the polypeptide is fused to a peptide signal sequence that is, or that comprises or is derived from the BMP-7 signal peptide. In other embodiments, the signal peptide sequence may be, or comprise or be derived from, other signal peptides.

The present invention further relates to vectors containing and expressing a polynucleotide encoding the proBMP-7 polypeptide, wherein the pre-BMP-7 signal peptide is deleted and wherein a peptide signal sequence from a different origin is fused to the proBMP-7 polypeptide. For example, in certain embodiments, the peptide signal sequence may be the insulin-like growth factor 1 (IGF-1) or the tissue plasminogen activator (tPA) peptide signal sequence. In a preferred embodiment the proBMP-7 encoded by the polynucleotide is a canine proBMP-7 polypeptide. Advantageously the proBMP-7 is encoded by a polynucleotide nucleotide that is, or comprises, or is derived from nucleotides 88 to 1296 of SEQ ID NO: 1, and that encodes, or comprises an amino acid sequence corresponding to amino acid residues 30 to 431 of SEQ ID NO: 3. In another preferred embodiment, the codon-optimized canine nucleotide sequence corresponding to SEQ ID NO: 2 is used.

In another preferred embodiment the proBMP-7 encoded by the polynucleotide is a human proBMP-7 polypeptide. Advantageously the proBMP-7 is encoded by a polynucleotide nucleotide that is, or comprises, or is derived from nucleotides 88 to 1296 of SEQ ID NO: 13, and that encodes, or comprises an amino acid sequence corresponding to amino acid residues 30 to 431 of SEQ ID NO: 15. In another preferred embodiment, the codon-optimized human nucleotide sequence corresponding to SEQ ID NO: 14 is used.

In another preferred embodiment the proBMP-7 encoded by the polynucleotide is a feline proBMP-7 polypeptide. Advantageously the proBMP-7 is encoded by a polynucleotide that is, or comprises, or is derived from nucleotides 88 to 1296 of SEQ ID NO: 17, and that encodes, or comprises an amino acid sequence corresponding to amino acid residues 30 to 431 of SEQ ID NO: 19. In another preferred embodiment, the codon-optimized feline nucleotide sequence corresponding to SEQ ID NO: 18 is used.

In embodiments where the signal peptide is derived from the IGF-I signal peptides, it is preferred that the peptide signal may be, or may comprise, or may be derived from, the horse IGF-1 peptide signal, and preferably that defined by amino acid residues 1 to 25 of SEQ ID NO: 9, and encoded by nucleotides 1 to 75 of SEQ ID NO: 8. In alternate embodiments, the IGF-1 peptide signal may be, or may comprise, or may be derived from, the canine IGF-1 peptide signal, and preferably is, or comprises, or is derived from, the canine IGF-1 peptide signal defined by amino acid residues 1 to 25 of SEQ ID NO: 12, and that is encoded by nucleotides 1 to 75 of SEQ ID NO: 11.

In other embodiments, the peptide signal may be, or may comprise, or may be derived from, the tPA peptide signal, such as the human tPA signal peptide. In a preferred embodiment, the tPA signal peptide used, is, or comprises or is derived from, amino acid residues 1 to 23 of the human tPA signal peptide sequence of SEQ ID NO: 5, and is encoded by nucleotides 1 to 69 of SEQ ID NO: 4. In an alternative embodiment, a human tPA signal peptide may be, or may comprise, or may be derived from, amino acid residues 1 to 28 of SEQ ID NO: 7 and is encoded by nucleotides 1 to 84 of SEQ ID NO: 6 may be used.

According to an advantageous embodiment of the invention, the expression vector may comprise the polynucleotides encoding the signal peptide of IGF1 or tPA according to SEQ ID NO: 5, 7, 9 or 12 fused to the pre-proBMP-7 polypeptide deleted of the signal peptide (corresponding to residue 30 to residue 431). According to another embodiment of the invention, the expression vector comprises the polynucleotides encoding the signal peptide of IGF1 or tPA fused to the mature BMP-7 (corresponding to residue 293 to residue 431). Polynucleotides comprising a desired sequence can be inserted into a suitable expression vector, and the vector in turn can be introduced into a suitable host cell, e.g. E. coli for replication and amplification.

In some embodiments, the present invention encompasses a vector capable of expressing canine pre-proBMP-7, canine proBMP-7, canine mature BMP-7, human pre-proBMP-7, human proBMP-7, human mature BMP-7, feline preproBMP-7, feline proBMP-7, feline mature BMP-7, or a variant or fragment thereof. For the mature BMP-7 or the proBMP-7, it is preferred that the nucleotide sequence encoding the peptide is preceded immediately by a nucleotide sequence in-frame encoding a peptide signal in order to facilitate the secretion of BMP-7 into the extra cellular medium. The signal sequence can be the natural sequence from the pre-proBMP-7 or a peptide signal from a secreted protein e.g. the signal peptide from the tissue plasminogen activator protein (tPA), in particular the human tPA (S. Friezner Degen et al J. Biol. Chem. 1996, 261, 6972-6985; R. Rickles et al J. Biol. Chem. 1988, 263, 1563-1569; D. Berg. et al Biochem. Biophys. Res. Commun. 1991, 179, 1289-1296), or the signal peptide from the Insulin-like growth factor 1 (IGF1), in particular the equine IGF1 (K. Otte et al. Gen. Comp. Endocrinol. 1996, 102(1), 11-15), the canine IGF1 (P. Delafontaine et al. Gene 1993, 130, 305-306), the feline IGF1 (WO-A-03/022886), the bovine IGF1 (S. Lien et al. Mamm. Genome 2000, 11(10), 877-882), the porcine IGF1 (M. Muller et al. Nucleic Acids Res. 1990, 18(2), 364), the chicken IGF1 (Y. Kajimoto et al. Mol. Endocrinol. 1989, 3(12), 1907-1913), the turkey IGF1 (GenBank accession number AF074980). The signal peptide from IGF1 may be natural or optimized, in particular optimized by removing cryptic splice sites and/or by adapting the codon usage.

As used herein the term "polynucleotide" is used to refer to a polymeric form of nucleotides of any length, which contain deoxyribonucleotides or ribonucleotides.

The present invention further encompasses a vector containing and expressing a polynucleotide encoding a BMP-7 polypeptide operably linked to a promoter element and optionally also linked to an enhancer. In an advantageous embodiment, the promoter is the promoter of the cytomegalovirus (CMV) immediate early gene, preferably from human- or murine-derived CMV. In other embodiments, the enhancers and/or promoters may be selected from among those promoters that are known in the art, and that are suitable for expression of BMP-7 in the vectors of the present invention. Many such promoters are known in the art, and suitable promoters can readily be selected by those of skill in the art. For example, there are various cell and/or tissue specific promoters (e.g., muscle, endothelial cell, liver, somatic cell, and stem cell specific promoters), and various viral promoters and enhancers, and BMP-7 promoters, such as those isogenically specific for each animal species. For example, in one embodiment, if the canine BMP-7 is to be expressed in a canine muscle cell, the enhancers and/or promoters specific to canine muscle cells may be used in order to optimize expression of canine BMP-7 for the desired application. Examples of muscle-specific promoters and enhancers have been described are known to one of skill in the art (see, e.g., Li et al., Gene Ther. 1999 December, 6(12), 2005-11; Li et al., Nat Biotechnol. 1999 March, 17(3), 241-5 and Loirat et al., Virology. 1999, Jul. 20, 260(1), 74-83; the disclosures of which are incorporated by reference in their entireties).

Promoters and enhancers that may be employed in the present invention include, but are not limited to the promoters and enhancers of the LTR of Rous sarcoma virus, the TK gene of HSV-1, the early or late promoters of SV40, the adenovirus major late promoter (MLP), phosphoglycerate kinase genes, metallothionein genes, α-1 antitrypsin genes, albumin genes, collagenase genes, elastase I genes, β-actin genes, β-globin genes, γ-globin genes, α-fetoprotein genes, and muscle creatin kinase genes.

In general, it is advantageous to employ a strong promoter functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No. WO87/03905. The CMV-IE promoter is advantageously a human CMV-IE (Boshart M. et al., Cell., 1985, 41, 521-530) or murine CMV-IE.

In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa M. et al., Vaccine, 2000, 18, 2337-2344), or the actin promoter (Miyazaki J. et al., Gene, 1989, 79, 269-277).

Functional sub fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Preferably, the plasmids comprise other expression control elements. It is particularly advantageous to incorporate stabilizing sequence(s), e.g., intron sequence(s), preferably the first intron of the hCMV-IE (PCT Application No. WO89/01036), the intron II of the rabbit β-globin gene (van Ooyen et al., Science, 1979, 206, 337-344). As to the polyadenylation signal (polyA) for the plasmids and viral vectors other than poxviruses, use can more be made of the poly(A) signal of the bovine growth hormone (bGH) gene (see U.S. Pat. No. 5,122, 458), or the poly(A) signal of the rabbit β-globin gene or the poly(A) signal of the SV40 virus.

The term "vector", as used herein, refers to a recombinant DNA or RNA plasmid or virus that comprises a heterologous polynucleotide to be delivered to a target cell, such as in vivo. The heterologous polynucleotide may comprise a sequence of interest for purposes of therapy, and may optionally be in the form of an expression cassette. As used herein, a "vector" need not be capable of replication in the ultimate target cell or subject.

The term "recombinant as used herein means a polynucleotide semisynthetic, or synthetic origin, which either does not occur in nature or is linked to another polynucleotide in an arrangement not found in nature.

The term "heterologous" as used herein derived from a genetically distinct entity from the rest of the entity to which it is being compared. For example, a polynucleotide may be placed by genetic engineering techniques into a plasmid or vector derived from a different source, and is thus a heterologous polynucleotide. A promoter removed from its native coding sequence and operatively linked to a coding sequence other than the native sequence is accordingly a heterologous promoter.

The polynucleotides of the invention may comprise additional sequences, such as additional coding sequences within the same transcription unit, controlling elements such as promoters, ribosome binding sites, transcription terminators, polyadenylation sites, additional transcription units under control of the same or different promoters, sequences that permit cloning, expression, homologous recombination, and transformation of a host cell, and any such construct as may be desirable to provide embodiments of this invention.

Elements for the expression of canine BMP-7 or feline BMP-7 or human BMP-7 are advantageously present in an inventive vector. In a minimum manner, this may comprise, may consist essentially of, or may consist of an initiation codon (ATG), a stop codon and a promoter, and optionally also a polyadenylation sequence for certain vectors such as plasmid and certain viral vectors, e.g., viral vectors other than poxviruses. When the polynucleotide encodes a polypeptide fragment, e.g. canine BMP-7, advantageously, in the vector, an ATG may be placed at 5' of the reading frame and a stop codon may be placed at 3'. Other elements for controlling expression may be present, such as enhancer sequences, stabilizing sequences, such as intron and signal sequences permitting the secretion of the protein.

Methods for making and/or administering a vector or recombinants or plasmid for expression of gene products of genes of the invention in vivo can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6; 312,683; U.S. patent application Ser. No. 920,197, filed Oct. 16, 1986; WO 90/01543; WO91/11525; WO 94/16716; WO 96/39491; WO 98/33510; EP 265785; EP 0 370 573; Andreansky et al., Proc. Natl. Acad. Sci. USA 1996, 93:11313-11318; Ballay et al., EMBO J. 1993; 4:3861-65; Felgner et al., J. Biol. Chem. 1994; 269, 2550-2561; Frolov et al., Proc. Natl. Acad. Sci. USA 1996, 93, 11371-11377; Graham, Tibtech 1990, 8, 85-87; Grunhaus et al., Sem. Virol. 1992, 3, 237-52; Ju et al., Diabetologia 1998, 41, 736-739; Kitson et al., J. Virol. 1991, 65, 3068-3075; McClements et al., Proc. Natl. Acad. Sci. USA 1996, 93, 11414-11420; Moss, Proc. Natl. Acad. Sci. USA 1996, 93, 11341-11348; Paoletti, Proc. Natl. Acad. Sci. USA 1996, 93, 11349-11353; Pennock et al., Mol. Cell. Biol. 1984, 4, 399-406; Richardson (Ed), Methods in Molecular Biology 1995, 39, "Baculovirus Expression Protocols," Humana Press Inc.; Smith et al. (1983) Mol. Cell. Biol. 1983, 3, 2156-2165; Robertson et al., Proc. Natl. Acad. Sci. USA 1996, 93, 11334-11340; Robinson et al., Sem. Immunol. 1997, 9, 271; and Roizman, Proc. Natl. Acad. Sci. USA 1996, 93, 11307-11312. Thus, the vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., human adenovirus, canine adenovirus), herpesvirus (e.g. canine herpesvirus), baculovirus, retrovirus, etc. (as in documents incorporated herein by reference); or the vector can be a plasmid. The cited and incorporated herein by reference documents, in addition to providing examples of vectors useful in the practice of the invention.

According to one embodiment of the invention, the expression vector may be a viral vector, in particular an in vivo expression vector. In an advantageous embodiment, the expression vector may be an adenovirus vector. Advantageously, the adenovirus may be a human adenovirus type 5 (hAd5) vector, an E1-deleted and/or an E3-deleted adenovirus.

In one particular embodiment the viral vector may be a poxvirus, e.g. a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, Munch. Med. Wschr., 1971, 113, 1149-1153; Sutter et al., Proc. Natl. Acad. Sci. U.S.A., 1992, 89, 10847-10851; available as ATCC VR-1508; or NYVAC, see U.S. Pat. No. 5,494,807, for instance, Examples 1 to 6 and et seq of U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO96/40241), an avipox virus or an attenuated avipox virus (e.g., canarypox, fowlpox, dovepox, pigeonpox, quailpox, ALVAC or TROVAC; see, e.g., U.S. Pat. Nos. 5,505,941, 5,494,807), swinepox, raccoonpox, camelpox, or myxomatosis virus.

According to another embodiment of the invention, the poxvirus vector may be a canarypox virus or a fowlpox virus vector, advantageously an attenuated canarypox virus or fowlpox virus. In this regard, reference is made to the canarypox available from the ATCC under access number VR-111. Attenuated canarypox viruses are described in U.S. Pat. No. 5,756,103 (ALVAC) and PCT application N° WO01/05934. Numerous fowlpox virus vaccination strains are also available, e.g. the DIFTOSEC CT strain marketed by MERIAL and the NOBILIS VARIOLE vaccine marketed by INTERVET; and, reference is also made to U.S. Pat. No. 5,766,599 which pertains to the atenuated fowlpox strain TROVAC.

For information on the method to generate recombinants thereof and how to administer recombinants thereof, the skilled artisan can refer documents cited herein and to PCT application N° WO90/12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993; 5,505,941 and U.S. Pat. No. 5,766,599 inter alia; as to canarypox mention is made of U.S. Pat. No. 5,756,103 inter alia; as to swinepox mention is made of U.S. Pat. No. 5,382,425 inter alia; and, as to raccoonpox, mention is made of PCT application N° WO00/03030 inter alia.

When the expression vector may be a vaccinia virus, insertion site or sites for the polynucleotide or polynucleotides to be expressed may be advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus may be advantageously as in various publications, including, but not limited to, Carroll M. W. et al., Vaccine, 1997, 15 (4), 387-394; Stittelaar K. J. et al., J. Virol. 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters. Advantageously, the polynucleotide to be expressed may be inserted under the control of a specific poxvirus promoter, e.g., the vaccinia promoter 7.5 kDa (Cochran et al., J. Virology, 1985, 54, 30-35), the vaccinia promoter I3L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia.

In a particular embodiment the viral vector may be an adenovirus, such as a human adenovirus (HAV) or a canine adenovirus (CAV).

In one embodiment the viral vector may be a human adenovirus, in particular a serotype 5 adenovirus, rendered incompetent for replication by a deletion in the E1 region of the viral genome, in particular from about nucleotide 459 to about nucleotide 3510 by reference to the sequence of the hAd5 disclosed in Genbank under the accession number M73260 and in the referenced publication J. Chroboczek et al Virol. 1992, 186, 280-285. The deleted adenovirus is propagated in E1-expressing 293 (F. Graham et al J. Gen. Virol. 1977, 36, 59-72) or PER cells, in particular PER.C6 (F. Falloux et al Human Gene Therapy 1998, 9, 1909-1917). The human adenovirus can be deleted in the E3 region, in particular from about nucleotide 28592 to about nucleotide 30470. The deletion in the E1 region can be done in combination with a deletion in the E3 region (see, e.g. J. Shriver et al. Nature, 2002, 415, 331-335, F. Graham et al Methods in Molecular Biology Vol. 7: Gene Transfer and Expression Protocols Edited by E. Murray, The Human Press Inc, 1991, p 109-128; Y. Ilan et al Proc. Natl. Acad. Sci. 1997, 94, 2587-2592; U.S. Pat. No. 6,133,028; U.S. Pat. No. 6,692,956; S. Tripathy et al Proc. Natl. Acad. Sci. 1994, 91, 11557-11561; B. Tapnell Adv. Drug Deliv. Rev. 1993, 12, 185-199; X. Danthinne et al Gene Thrapy 2000, 7, 1707-1714; K. Berkner Bio Techniques 1988, 6, 616-629; K. Berkner et al Nucl. Acid Res. 1983, 11, 6003-6020; C. Chavier et al J. Virol. 1996, 70, 4805-4810). The insertion sites can be the E1 and/or E3 loci (region) eventually after a partial or complete deletion of the E1 and/or E3 regions. Advantageously, when the expression vector is an adenovirus, the polynucleotide to be expressed is inserted under the control of a promoter functional in eukaryotic cells, such as a strong promoter, preferably a cytomegalovirus immediate-early gene promoter (CMV-IE promoter), in particular the enhancer/promoter region from about nucleotide −734 to about nucleotide +7 in M. Boshart et al Cell 1985, 41, 521-530 or the enhancer/promoter region from the pCI vector from PROMEGA Corp. The CMV-IE promoter is advantageously of murine or human origin. The promoter of the elongation factor 1α can also be used. In one particular embodiment a muscle specific promoter can be used (X. Li et al Nat. Biotechnol. 1999, 17, 241-245). Strong promoters are also discussed herein in relation to plasmid vectors. In one embodiment, a splicing sequence can be located downstream of the enhancer/promoter region. For example, the intron 1 isolated from the CMV-IE gene (R. Stenberg et al J. Virol. 1984, 49, 190), the intron isolated from the rabbit or human β-globin gene, in particular the intron 2 from the β-globin gene, the intron isolated from the immunoglobulin gene, a splicing sequence from the SV40 early gene or the chimeric intron sequence isolated from the pCI vector from Promega Corp. comprising the human β-globin donor sequence fused to the mouse immunoglobulin acceptor sequence (from about nucleotide 890 to about nucleotide 1022 in Genbank under the accession number CVU47120). A poly(A) sequence and terminator sequence can be inserted downstream the polynucleotide to be expressed, e.g. a bovine growth hormone gene, in particular from about nucleotide 2339 to about nucleotide 2550 in Genbank under the accession number BOVBMP-7, a rabbit β-globin gene or a SV40 late gene polyadenylation signal.

In another embodiment the viral vector may be a canine adenovirus, in particular a CAV-2 (see, e.g. L. Fischer et al. Vaccine, 2002, 20, 3485-3497; U.S. Pat. No. 5,529,780; U.S. Pat. No. 5,688,920; PCT Application No. WO95/14102). For CAV, the insertion sites can be in the E3 region and/or in the region located between the E4 region and the right ITR region (see U.S. Pat. No. 6,090,393; U.S. Pat. No. 6,156,567). In one embodiment the insert may be under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

In another particular embodiment the viral vector may be a herpesvirus such as a canine herpesvirus (CHV) or a feline herpesvirus (FHV). For CHV, the insertion sites may be in particular in the thymidine kinase gene, in the ORF3, or in the UL43 ORF (see U.S. Pat. No. 6,159,477). In one embodiment the polynucleotide to be expressed may be inserted under the control of a promoter functional in eukaryotic cells, advantageously a CMV-IE promoter (murine or human). In one particular embodiment a promoter regulated by hypoxia, e.g. the promoter HRE described in K. Boast et al Human Gene Therapy 1999, 13, 2197-2208), can be used. A poly(A) sequence and terminator sequence can be inserted downstream the polynucleotide to be expressed, e.g. bovine growth hormone or a rabbit β-globin gene polyadenylation signal.

According to a yet further embodiment of the invention, the expression vector may be a plasmid vector or a DNA plasmid vector, in particular an in vivo expression vector. In a specific, non-limiting example, the pVR1020 or 1012 plasmid (VICAL Inc.; Luke C. et al., Journal of Infectious Diseases, 1997, 175, 91-97; Hartikka J. et al., Human Gene Therapy, 1996, 7, 1205-1217) can be utilized as a vector for the insertion of a polynucleotide sequence. The pVR1020 plasmid is derived from pVR1012 and contains the human tPA signal sequence. In one embodiment the human tPA signal comprises from amino acid Met(1) to amino acid Ser(23) or Ala(28) in Genbank under the accession number HUMTPA14. In another specific, non-limiting example, the plasmid utilized as a vector for the insertion of a polynucleotide sequence can contain the signal peptide sequence of equine IGF1 from amino acid Met(24) to amino acid Ala(48) in Genbank under the accession number U28070.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid may comprise or may contain or may consist essentially of, in addition to the polynucleotide encoding the pre-proBMP-7, the proBMP-7 or the mature BMP-7 polypeptide, the BMP-7 polypeptide being preferably from canine origin, feline origin, human origin, variant, analog or fragment, operably linked to a promoter or under the control of a promoter or dependent upon a promoter.

The present invention also relates to a pharmaceutical composition comprising a vector expressing in vivo under appropriate or suitable conditions or in a suitable host cell. The pharmaceutical compositions may comprise, may consist essentially of, or may consist of one or more vectors, e.g., expression vectors, such as in vivo expression vectors, comprising, consisting essentially or consisting of and expressing one or more polynucleotides encoding a BMP-7 polypeptide, optionally fused with a BMP-7, IGF-1 or tPA signal peptide, in a pharmaceutically or veterinarily acceptable carrier, excipient or vehicle. Advantageously, the vector may comprise, may consist essentially of, or may consist of and expresses at least one polynucleotide encoding a canine BMP-7 polypeptide or a feline BMP-7 polypeptide or a human BMP-7 polypeptide, optionally fused with a BMP-7, IGF-1 or tPA signal peptide, in a pharmaceutically or veterinarily acceptable carrier, excipient or vehicle. Thus, according to an embodiment of the invention, the other vector or vectors in the composition may comprise a polynucleotide that encodes, and under appropriate circumstances expresses one or more other proteins, polypeptides or peptides than the canine BMP-7 polypeptide or a feline BMP-7 polypeptide or a human BMP-7 polypeptide.

Compositions containing one or more vectors containing, may comprise, may consist essentially of, or may consist of polynucleotides encoding, and advantageously expressing, in vivo, a canine BMP-7 polypeptide or a feline BMP-7 polypeptide or a human BMP-7 polypeptide or fusion protein thereof.

In an advantageous embodiment, the invention may provide for the administration of a therapeutically effective amount of a formulation for the delivery and expression of a BMP-7 polypeptide in a target cell. Determination of the therapeutically effective amount is routine experimentation for one of ordinary skill in the art. In one embodiment, the formulation comprises an expression vector comprising a polynucleotide that expresses BMP-7 polypeptide and a pharmaceutically or veterinarily acceptable carrier, vehicle or excipient. In an advantageous embodiment, the pharmaceutically or veterinarily acceptable carrier, vehicle or excipient may facilitate transfection and/or may improve preservation of the vector.

The pharmaceutically or veterinarily acceptable carriers or vehicles or excipients are well known to the one skilled in the art. For example, a pharmaceutically or veterinarily acceptable carrier or vehicle or excipient can be water or a 0.9% NaCl (e.g., saline) solution or a phosphate buffer. Other pharmaceutically or veterinarily acceptable carrier or vehicle or excipients that can be used for methods of this invention include, but are not limited to, poly(L-glutamate) or polyvinylpyrrolidone. The pharmaceutically or veterinarily acceptable carrier or vehicle or excipients may be any compound or combination of compounds facilitating the administration of the vector, increasing the level of expression or increasing the duration of expression. Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

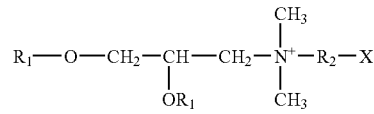

in which $R_1$ is a saturated or unsaturated straight-chain aliphatic radical having 12 to 18 carbon atoms, $R_2$ is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; PCT Application No. WO96/34109), wherein the cationic lipid can be advantageously associated with a neutral lipid, advantageously DOPE (dioleoyl-phosphatidyl-ethanol amine; Behr J. P., 1994, Bioconjugate Chemistry, 5, 382-389), to form DMRIE-DOPE.

Advantageously, the plasmid mixture with the excipient may be formed extemporaneously and advantageously contemporaneously with administration of the preparation or shortly before administration of the preparation; for instance, shortly before or prior to administration, the plasmid-excipient mixture is formed, advantageously so as to give enough time prior to administration for the mixture to form a complex, e.g. between about 10 and about 60 minutes prior to administration, such as approximately 30 minutes prior to administration. When DOPE is present, the DMRIE:DOPE molar ratio is advantageously about 95:about 5 to about 5:about 95, more advantageously about 1:about 1, e.g., 1:1.

The DMRIE or DMRIE-DOPE adjuvant:plasmid weight ratio can be between about 50:about 1 and about 1:about 10, such as about 10:about 1 and about 1:about 5, and advantageously about 1:about 1 and about 1:about 2, e.g., 1:1 and 1:2.

In a specific embodiment, the pharmaceutical composition may be directly administered in vivo, and the encoded product is expressed by the vector in the host. The methods to deliver in vivo a vector encoding a BMP-7 polypeptide, advantageously the canine BMP-7 polypeptide (see, e.g., U.S. Pat. No. 6,423,693; EP-A-1 052 286, EP-A-1 205 551, U.S. Patent Application 2004/0057941, PCT Application No. WO9905300 and Draghia-Akli et al., Mol Ther. 2002 December, 6(6), 830-6; the disclosures of which are incorporated by reference in their entireties) or the feline BMP-7 polypeptide or the human BMP-7 polypeptide, can be modified to deliver the BMP-7 polypeptide, of the present invention to a human, a canine animal or a feline animal, notably man, woman, child, dog, bitch, puppy, cat or kitten. The in vivo delivery of a vector encoding and expressing the BMP-7 described herein can be accomplished by one of ordinary skill in the art given the teachings of the above-mentioned references.

Advantageously, the pharmaceutical compositions and/or formulations according to the invention comprise or consist essentially of or consist of an effective quantity of one or more expression vectors to elicit a therapeutic response as discussed herein; and, an effective quantity can be determined from this disclosure, including the documents incorporated herein, and the knowledge in the art, without undue experimentation.

In the case of therapeutic and/or pharmaceutical compositions based on a plasmid vector, a dose may comprise, may consist essentially of, or may consist of, in general terms, about in 1 µg to about 2000 µg, advantageously about 50 µg to about 1000 µg and more advantageously from about 100 µg to about 800 µg of plasmid expressing BMP-7 polypeptide. When the pharmaceutical compositions based on a plasmid vector is administered with electrotransfer the dose of plasmid is generally between about 0.1 µg and 1 mg, advantageously between about 1 µg and 100 µg, advantageously between about 2 µg and 50 µg.

In an advantageous embodiment the pharmaceutical composition comprising a plasmid vector(s) according to the invention may be administered preferably by intramuscular route with electrotransfer to improve the uptake of the vector by the host cells. The features of the electrotransfer alternatively or in combination may be: (1) a mono or bipolar electric fields, preferably unipolar; (2) an electric field varying from 10 to 250 V/cm, preferably 50 to 200 V/cm; (3) an electric pulse duration of 10 to 50 msec, preferably of 15 to 25 msec; (4) an interval inter pulse varying from 10 to 990 msec, preferably from 50 to 250 msec; (5) a frequency varying from 1 to 50 Hz, preferably from 4 to 20 Hz, most preferably from 6 to 10 Hz; (6) a number of pulses varying from 1 to 15, preferably 4 to 10; (7) a duration of treatment will vary between 0.1 and 5 sec, preferably between 0.5 and 2.5 sec, most preferably between 0.75 and 1.5 sec; (8) the electrodes can be either invasive or non invasive; (9) the number of electrotransfer per treatment will be comprised between 1 and 10, preferably between 1 and 5 and most preferably between 1 and 2, the frequency of treatments will be established based on induced plasma concentrations of BMP-7 polypeptide; (10) the electrotransfer can be applied with or without anaesthesia or sedation. The electrotransfer can be performed also directly on the kidneys.

The pharmaceutical composition comprising plasmid vector(s) or adenovirus vector(s) can be alternatively administer by sonoporation: (1) the conditions are defined in order to avoid shearing induced by ultrasounds exposure; the plasmid(s) can be protected by polymers, preferably by cationic polymers; (2) a commercial contrast agents used in echocardiography (e.g., PESDA perfluorocarbon or Optison) can de used to improve efficacy, based on acoustic cavitation mechanisms (or others); (3) the route of administration is preferably intramuscular or intravascular that is of interest to target an internal organ like the kidneys; (4) the diagnostic pulsed US is better than continuous wave system; (5) the efficacy is enhanced when plasmid(s) is complexed with cationized gelatine.

Alternatively to enhance in vivo gene delivery with minimal tissue damage the pharmaceutical composition can be administered using a femtosecond infrared laser (LBGT technology).

The pharmaceutical composition may be advantageously administered by intra vascular delivery into the kidney. The hemodynamic-based plasmid DNA gene delivery method may be based on the change of the hemodynamic of blood circulation in the recipient animals following the injection of a large volume of DNA solution within a short period of time. It has been demonstrated that the delivery of naked DNA through intraportal or intrahepatic vein injection results in high levels of gene expression. The specific expression in the mammalian kidney may be achieved following direct retrograde injection into the renal veins. Preferably the specific expression in the mammalian kidney may be achieved following direct retrograde injection into the left renal vein. Animals are pre-treated with an anticoagulant (e.g. with acetylsalicylic acid (e.g. Aspegic)) to avoid thrombosis side effects. Animals are anaesthetized generally using an isoflurane-based classical anaesthesia technique. An occlusion balloon catheter (e.g., Ulltra-thin Diamond Balloon Dilatation catheter (Boston Scientific, Boston, Mass., USA)) may be inserted, notably from the femoral or jugular vein (e.g. with angiocatheter sheath), into the renal vein, notably under fluoroscopy navigation. Optionally 10 ml (i.e., 1 ml/kg of the animal weight for a 10 kg dog) of normal saline buffer may be injected for washing out of renal blood at a flow rate of from about 0.1 to about 0.5 ml/sec. The renal vein may be subsequently occluded by inflation of the balloon. A typical dose of plasmid DNA is from about 0.0005 to about 0.5 mg/kg of animal weight, preferably from about 0.005 to about 0.05 mg/kg of animal weight and more preferably about 0.2 mg/kg of animal weight. The plasmid DNA may be rapidly injected into the renal vein with from about 5 to about 25 ml of normal saline buffer, preferably from about 10 to about 20 ml, more preferably from about 12.5 to about 17.5 ml and most preferably about 15 ml. The plasmid DNA may be rapidly injected into the renal vein, potentially using a power injector, to ensure a flow of from about 0.5 to about 3 ml/sec, preferably from about 0.5 to about 2 ml/sec, more preferably from about 0.75 to about 1.5 ml/sec and most preferably about 1 ml/sec.

The balloon occlusion may be continued during the rapid injection and stopped from about 10 sec to about 3 min after the injection. Preferably, this occlusion may be stopped about 1 min after the injection. After that, the occlusion balloon may be removed.

For a typical 15 kg dog, 15 ml of normal saline buffer may be injected for washing out of renal blood at a flow rate of 0.5 ml/sec. For the typical 15 kg dog, a typical dose of 0.2 mg/kg of plasmid DNA is rapidly injected into the renal vein with 15 ml of normal saline buffer using a power injector to ensure a flow of 1 ml/s.

For electrotransfer, sonoporation or femtosecond infrared laser administration, the dose volumes can be between about 0.1 and about 2 ml, advantageously between about 0.2 and about 1 ml. These doses and dose volumes are suitable for the treatment of canines and other mammalian target species such as humans, equines and felines.

When using a viral vector system, the therapeutic and/or pharmaceutical composition contains per dose from about $10^4$ to about $10^{11}$, advantageously from about $10^5$ to about $10^{10}$ and more advantageously from about $10^6$ to about $10^9$ viral particles of recombinant adenovirus expressing BMP-7 polypeptide. In the case of therapeutic and/or pharmaceutical compositions based on a poxvirus, a dose can be between about $10^2$ pfu and about $10^9$ pfu. The pharmaceutical composition contains per dose from about $10^5$ to $10^9$, advantageously from about $10^6$ to $10^8$ pfu of poxvirus or herpesvirus recombinant expressing BMP-7 polypeptide. The dose volume of compositions for target species that are mammals, e.g., the dose volume of canine compositions, based on viral vectors, e.g., non-poxvirus-viral-vector-based compositions, may be generally between about 0.1 to about 2.0 ml, preferably between about 0.1 to about 1.0 ml, and more preferably between about 0.5 ml to about 1.0 ml. This administration may be, but is not limited to, intramuscular (IM), subcutaneous (SC), intravascular (IV) or intrarenal injection. Alternative routes to reach the kidneys are: renal artery, injection into the renal subcapsular space, retrograde injection from the ureter injection.

The present invention may contemplate at least one administration to an animal of an efficient amount of the therapeutic composition made according to the invention. The animal may be male, female, pregnant female and newborn. In an advantageous embodiment, the animal may be a mammal. In a more advantageous embodiment, the mammal may be a human, a canine animal or a feline animal, notably man, woman, child, dog, bitch, puppy, cat, queen or kitten.

The therapeutic composition according to the invention can also be administered by a needle free apparatus (as, for example with a Pigjet, Biojector or Vitajet apparatus (BIOJECT, Oregon, USA)). Another approach to administer plasmid compositions may be to use electrotransfer (see, e.g. S. Tollefsen et al. Vaccine, 2002, 20, 3370-3378; S. Tollefsen et al. Scand. J. Immunol., 2003, 57, 229-238; S. Babiuk et al., Vaccine, 2002, 20, 3399-3408; PCT Application No. WO99/01158).

It should be understood by one of skill in the art that the disclosure herein regarding administration of the compositions of the invention is provided by way of example, and that the present invention is not limited to the specific examples described. From the disclosure herein, and from the knowledge in the art, the skilled artisan can determine the number of administrations, the administration route, and the doses to be used for each administration of the compositions of the present invention without any undue experimentation.

In a preferred embodiment, the present invention relates to the use of, and to compositions comprising, a viral vector or a plasmid vector encoding and capable of expressing, a canine pre-proBMP-7, a canine proBMP-7, a canine BMP-7 mature polypeptide, human pre-proBMP-7, human proBMP-7, human mature BMP-7, feline pre-proBMP-7, feline proBMP-7, feline mature BMP-7, or a variant, derivative or fragment thereof, for the treatment and/or prevention of ARF or CRF by intrarenal injection. However, in other embodiments of the invention, the methods and compositions disclosed herein may be used to treat and/or prevent other diseases and conditions, including, but not limited to, other kidney conditions, disorders and diseases, anorexia, weight loss, dehydration, depression, vomiting, polyuria and/or polydipsia.

In a preferred embodiment the invention relates to the use of the pharmaceutical compositions according to the present invention to treat mammals presenting an increase in their serum creatinine concentration and/or an increase in their BUN concentration, or an increase in their urine specific gravity.

Advantageously a cat may be treated when the plasma creatinine concentration is higher than 1.9 mg/dl and/or when the plasma urea nitrogen concentration is higher than 35 mg/dl. Advantageously a dog may be treated when the plasma creatinine concentration is higher than 1.6 mg/dl and/or when the plasma urea nitrogen concentration is higher than 30 mg/dl.

Advantageously a human may be treated when the presence of a functional or structural renal abnormality that evolved over more than 3 months (this can be a morphological abnormality provided it is clinically significant or a histological abnormality or a modification of blood and/or urine composition secondary to a renal insult) and/or when a Glomerular Filtration Rate (GRF) is below 60 ml/min/1.73 m² over more than 3 month.

The GFR may be estimated in humans based on the Cockcroft and Gault formula:

$$GFR \text{ (in ml/mm)} = k \times [140 - age \text{ (in years)}] \times Body$$
$$Weight \text{ (in kg)}]/Creatinemia \text{ (in } \mu mol/l) \text{ with}$$
$$k = 1.23 \text{ for males and } 1.04 \text{ for females.}$$

The result may be reported to the body surface for normalization per 1.73 m² (Body surface=√Body weight (kg)× Height (m)/3600).

Based on GFR estimation (in ml/min/1.73 m²) the CRF grade can be specified:

Grade 1: CRF with normal functionality: GFR≧90

Grade 2: Limited CRF: GFR 60-90

Grade 3: Moderate CRF: GFR 30-59

Grade 4: Severe CRF: GFR 15-29

Grade 5: terminal CRF: GFR<15

The invention will now be further described by way of the following non-limiting examples.

Example 1

Construction of the Plasmid pNB292

The codon-optimized canine BMP7 open reading frame ("ORF") consists of 1296 by and encodes a 431 amino acids polypeptide (SEQ ID NO: 2). The codon-optimized cDNA, encoding the polypeptide sequence of SEQ ID NO: 3, and flanked by unique SalI and XbaI restriction sites, was synthesized from overlapping oligonucleotides, assembled by hybridization and cloned into the pCR-Script vector (Invitrogen) to generate plasmid pPCR-Script050876 (FIG. 1).

Figure 2:
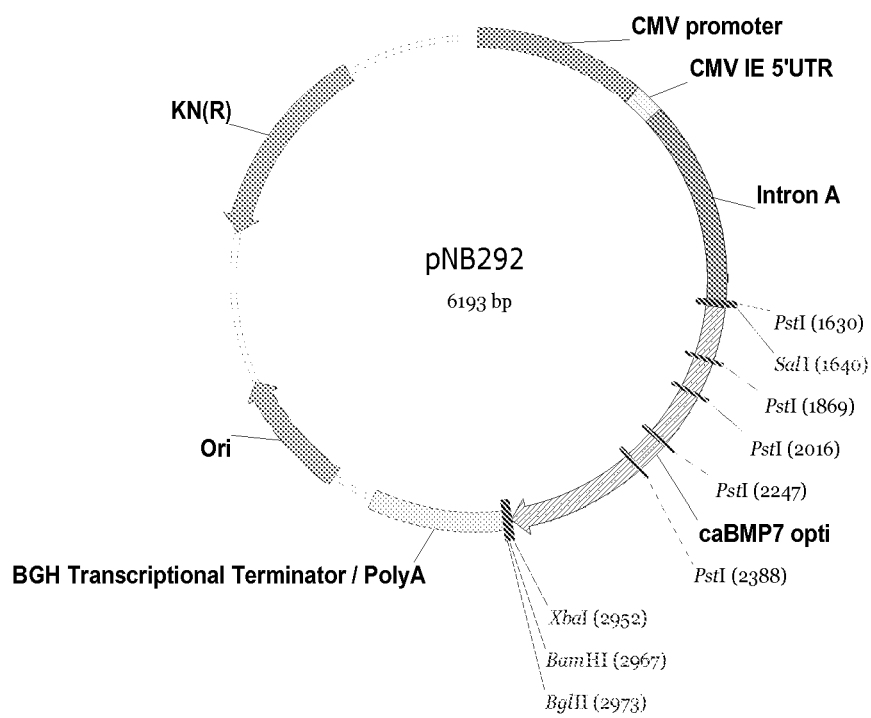
FIG. 2 depicts the pNB292 plasmid map and the encoded ORF of the canine BMP-7. The nucleotide sequence of the encoded ORF is that of SEQ ID NO: 2 and the amino acid sequence of the encoded ORF is that of SEQ ID NO: 3.

The DNA fragment corresponding to the ORF of interest was excised using SalI and XbaI digestions and further cloned into the pVR1012 plasmid (J. Hartikka et al. Human Gene Therapy 1996, 7, 1205-1217) to generate the pNB292 plasmid (FIG. 2) in which the expression of the codon-optimized canine BMP-7 is driven by the cytomegalovirus immediate early (CMV IE) promoter/enhancer. The nucleotide sequence of the pNB292 plasmid is that of SEQ ID NO: 10. The pNB292 plasmid was transformed into DH5α E. coli bacteria and subsequently purified using a commercial kit as recommended by the manufacturer (QIAGEN). Final plasmid concentrations were 2 mg/ml in TE buffer.

The transient in vitro expression of the polypeptide encoded by the pNB292 plasmid was confirmed and observed after transfection of CHO-K1 cells, using Lipofectamin 2000 (INVITROGEN). CHO-K1 cells at 90% confluence in 6 cm diameter plates were transfected with 5 µg plasmid and 10 µl lipofectamine each, according to the manufacturer's instructions. After transfection, cells were cultivated in MEM-glutamax medium containing 1% foetal calf serum for 24 hours. Cells grown on glass coverslips were washed with PBS, incubated for 10 min in cold acetone for additional fixing and permeabilisation, and again washed in PBS. Recombinant protein production was analysed by indirect immunofluorescence, using an anti-human BMP7 polyclonal serum (ABCAM, Cambridge UK). The immunochemical method confirmed that the pre-proBMP-7 polypeptide encoded by pNB292 was expressed in CHO-K1 cells.

Example 2

Therapeutic Effect of BMP-7 Plasmid-Based Gene Therapy

A study was conducted in rats to demonstrate the ability of BMP-7 gene therapy to reduce the intensity of tubulo-interstitial lesions associated with the evolution of an experimental unilateral ureteral obstruction (UUO) model of chronic renal failure.

20 male Sprague-Dawley rats weighting approximately 200 g at the initiation of the study were purchased from IFFACREDO (L'Arbresle, France). The maximum and minimum of both temperature and hygrometry of the room were recorded daily. The target temperature and hygrometry range were 20-24° C. and 20-70%, respectively. Light was provided using an automatic timer in cycles of 12 hours light and 12 hours dark. Only healthy rats were included in the study. Rats were allocated randomly to 4 groups of 5 animals each (Groups 1 to 4).

Unilateral ureteral obstruction (UUO) was performed on rats from groups 2, 3 and 4, using an established procedure (R. Chevalier et al., Kidney Int. 2000, 57, 882-890). Briefly, rats were anaesthetized by intramuscular injection of tiletamine-zolazepam (ZOLETIL® 100—20 to 50 mg/kg—VIRBAC, France). The abdomen was clipped free of fur and the ventral skin was scrubbed with providone iodine. A medial incision of the skin and the abdominal lining was performed. The left ureter was exposed and occluded by tightening the tubing with two 5.0 silk sutures approximately 5 mm away from each other. The suture of the abdominal lining and skin was performed using a silk thread (Silk dec. 0, ETHICON, France). The rats in group 2 were sham-operated, i.e. these animals had their ureters surgically exposed and manipulated, but not ligated. The rats in group 1 were kept as a control, with no surgery performed.

The plasmid gWIZ-SEAP® expressing the control transgene SEAP was purchased from GTS Inc. (San Diego, USA) and used as a placebo. The pNB292 plasmid was constructed according to example 1. Final plasmid concentrations were 2 mg/ml in TE buffer.

Individual animals were treated at two days prior to surgery (D−2) and five days after surgery (D+5), D0 being the day of surgery. An intramuscular pre-treatment with 100 μl of hyaluronidase at 30 U/100 μl was performed on each targeted muscle two hours prior to the injection of plasmids. Rats were subsequently anaesthetized (by intramuscular injection of tiletamine-zolazepam: ZOLETIL® 100—20 to 50 mg/kg—VIRBAC, France) and half a dose of plasmid solution (i.e., 200 μL) was administrated by intramuscular (IM) injection into each tibialis cranialis muscle region at D−2 and into each semi-membranous muscle region at D+5. Each injection of 200 μl corresponded to half a dose of plasmid, i.e., 400 μg. Each plasmid-injected rat received a total amount of 800 μg of DNA per day of treatment. The following table recapitulates volumes and masses of plasmid injected

TABLE 2

| | Plasmid injections | | | | | | | |
|---|---|---|---|---|---|---|---|---|
| | Group 1 | | Group 2 | | Group 3 | | Group 4 | |
| | D − 2 | D + 5 | D − 2 | D + 5 | D − 2 | D + 5 | D − 2 | D + 5 |
| Tibialis cranialis left | — | — | — | — | 200 μl (0.4 mg) | — | 200 μl (0.4 mg) | — |
| Tibialis cranialis right | — | — | — | — | 200 μl (0.4 mg) | — | 200 μl (0.4 mg) | — |
| Semi membranous left | — | — | — | 200 μl (0.4 mg) | — | 200 μl (0.4 mg) | — | 200 μl (0.4 mg) |
| Semi membranous right | — | — | — | 200 μl (0.4 mg) | — | 200 μl (0.4 mg) | — | 200 μl (0.4 mg) |

The specific plasmid compositions administered for each group are specified in table 3.

TABLE 3

| Plasmid compositions administered | | | | |
|---|---|---|---|---|
| | Plasmid composition per dose (400 μL) | | | |
| | Group 1 | Group 2 | Group 3 | Group 4 |
| pNB292 | — | — | 400 μg | |
| gWIZ-SEAP | — | — | 400 μg | 800 μg |

Within the five minutes following plasmid intramuscular delivery, electrotransfer (ET) was applied to each injected muscle using non-invasive plaque electrodes (approximately 0.8 cm² each) in the presence of conductive gel between the skin and the electrodes. The inter-electrode distance was measured to be approximately 0.8 cm. A train of 8 electric pulses of 20 msec each was applied at a frequency of 8 Hz over 1.3 sec. The applied voltage was 140 V targeting a field of 175 V/cm.

All rats were euthanized 13 days after surgery (D+13). One half of each left kidney was fixed in 10% buffered formalin for histopathogical analysis. After fixation, each sample was dehydrated in alcohol solutions of increasing concentration, cleared in isoparaffin H and embedded in paraffin. Embedded samples were cut into 5 μm sections using a microtome (MICROM®, France). Four sections per site were prepared and stained with Hematoxylin-Eosin-Safranin ("HES") and Masson Trichrome. Histological sections were observed using a microscope (ECLIPSE E600) fitted with ×2, ×4, ×10, ×25 and ×40 objectives. Renal morphological injury, as characterized by tubular dilatation with epithelial atrophy and interstitial expansion with matrix deposition, was scored in a blind fashion based on a scale of 0 (absent), 1 (mild), 2 (moderate), 3 (limited) and 4 (severe). The overall mean scores and the frequency of each grading were calculated based on individual values, which were determined on 10 fields per rat, 6 rats per group.

It was found that plasmid-expressed BMP-7 attenuated renal interstitial fibrosis 13 days post unilateral ureteral obstruction (UUO).

Figure 3:
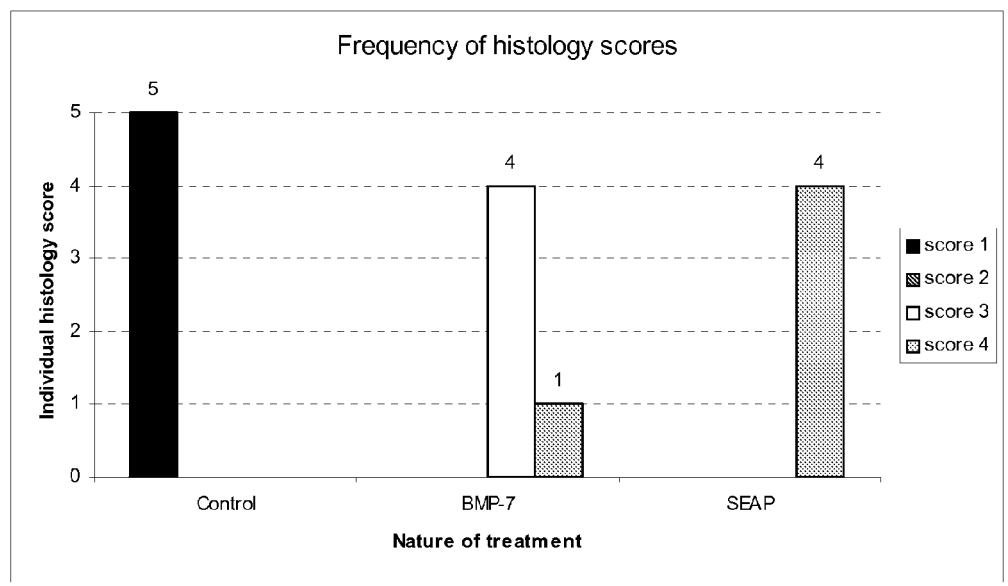
FIG. 3 provides a histogram illustrating the frequency of kidney lesions having certain grades in control rats and in rats treated with a plasmid expressing BMP-7.
Figure 4:
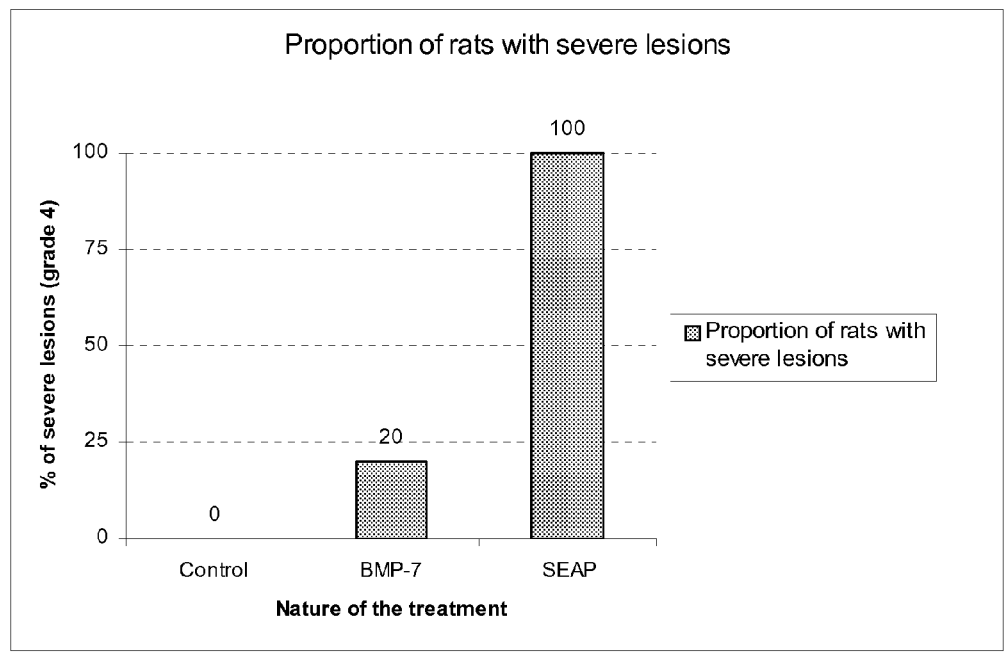
FIG. 4 provides a histogram illustrating the frequency of severe lesions in control rats and in rats treated with a plasmid expressing BMP-7.

FIG. 3 provides histograms of the frequency of lesion grades in the control versus treated groups. No alteration of the renal tissue could be observed in any of the 5 rats of the non-obstructed control group 1, all rats maintaining totally normal kidney architecture graded as "0". In contrast, 4 out of 5 rats of the obstructed but non-treated control group 2 had severe lesions at a grade of 4. A single rat in this group scored at a grade of 3, demonstrating the severity of the experimental model. All 4 out of the 4 rats in the SEAP-treated group (group 4) also presented severe lesions scored at grade 4, thus confirming the severity of the challenge in this group treated with a non-relevant transgene. In contrast, 4 out 5 rats in the BMP-7 treated group 3 (group 3) had a lesion score of 3 with only one rat in this group with severe lesions graded 4. Therefore the proportion of severe (grade 4) lesions in the BMP-7-treated group was 20% as compared to 80% in the untreated control group (group 2) and 100% in the placebo treated group (group 4) (FIG. 4).

This data clearly demonstrates the therapeutic effect of BMP-7 plasmid-based gene therapy in a very severe experimental model of tubulo-interstitial nephritis.

Example 3

Construction of the Plasmid pMEB038

Figure 5:
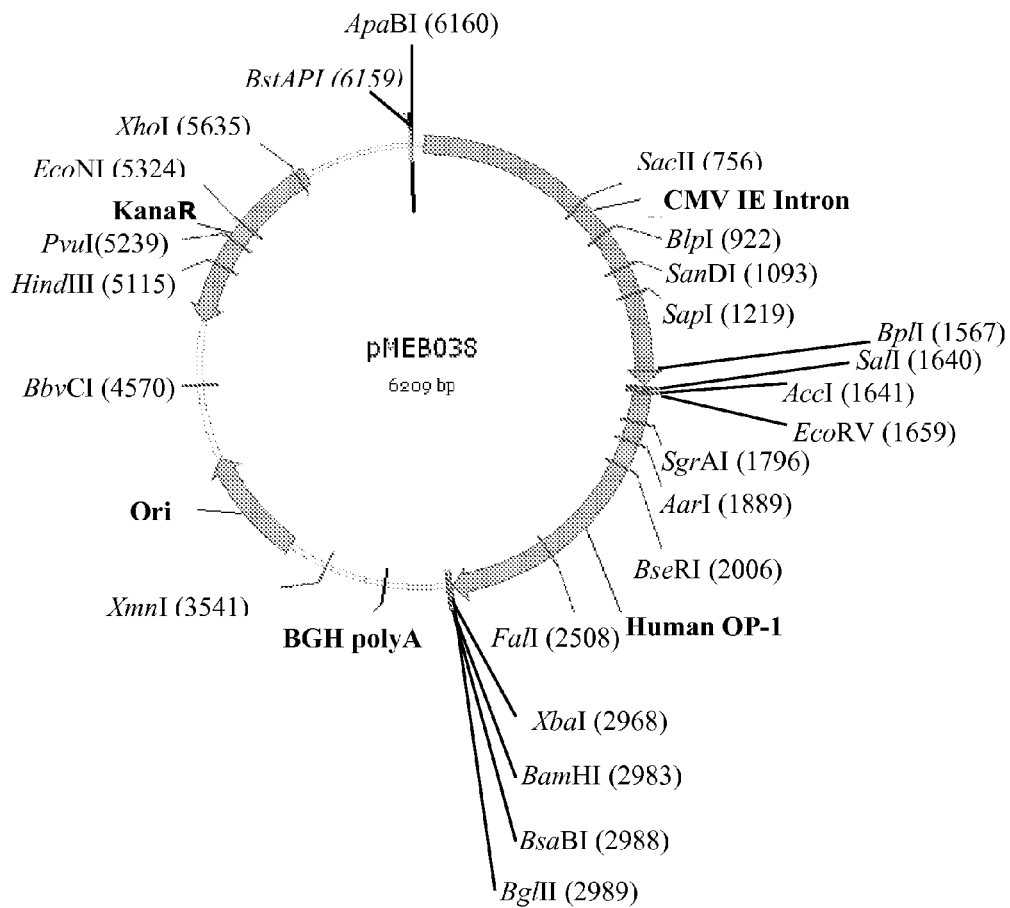
FIG. 5 depicts the pMEB038 plasmid map and the encoded ORF of the human BMP-7. The nucleotide sequence of the encoded ORF is that of SEQ ID NO: 14 and the amino acid sequence of the encoded ORF is that of SEQ ID NO: 15.

The codon-optimized human BMP7 open reading frame ("ORF") consists of 1296 by and encodes a 431 amino acids polypeptide (SEQ ID NO: 15). The codon-optimized cDNA, encoding the polypeptide sequence of SEQ ID NO: 14, and flanked by unique EcoRV and XbaI restriction sites, was synthesized from overlapping oligonucleotides, assembled by hybridization and cloned into the pVR1012 plasmid (J. Hartikka et al. Human Gene Therapy 1996, 7, 1205-1217) to generate the pMEB038 plasmid (FIG. 5) in which the expression of the codon-optimized human BMP-7 is driven by the cytomegalovirus immediate early (CMV IE) promoter/enhancer. The nucleotide sequence of the pMEB038 plasmid is that of SEQ ID NO: 16. The pMEB038 plasmid was transformed into DH5α *E. coli* bacteria and subsequently purified using a commercial kit as recommended by the manufacturer (Pure Yield™ Plasmid Midiprep, Promega). Final plasmid concentrations were 2 mg/ml in TE buffer.

The transient in vitro expression of the polypeptide encoded by the pMEB038 plasmid was confirmed and observed after transfection of CHO-K1 cells, using Lipofectamin 2000 (INVITROGEN). CHO-K1 cells at 90% confluence in 6 cm diameter plates were transfected with 5 µg plasmid and 10 µl lipofectamine each, according to the manufacturer's instructions. After transfection, cells were cultivated in MEM-glutamax medium containing 1% foetal calf serum for 24 hours. Cells grown on glass coverslips were washed with PBS, incubated for 10 min in cold acetone for additional fixing and permeabilisation, and again washed in PBS. Recombinant protein production was analysed by indirect immunofluorescence, using an anti-human BMP7 polyclonal serum and monoclonal antibodies (MAB3542, BAM354 and AF354 from R&D Systems, and SC-9305 and SC-6899 from Santa Cruz). The immunochemical method confirmed that the pre-proBMP-7 polypeptide encoded by pMEB038 was expressed in CHO-K1 cells.

Example 4

Construction of the Plasmid pMEB039

Figure 6:
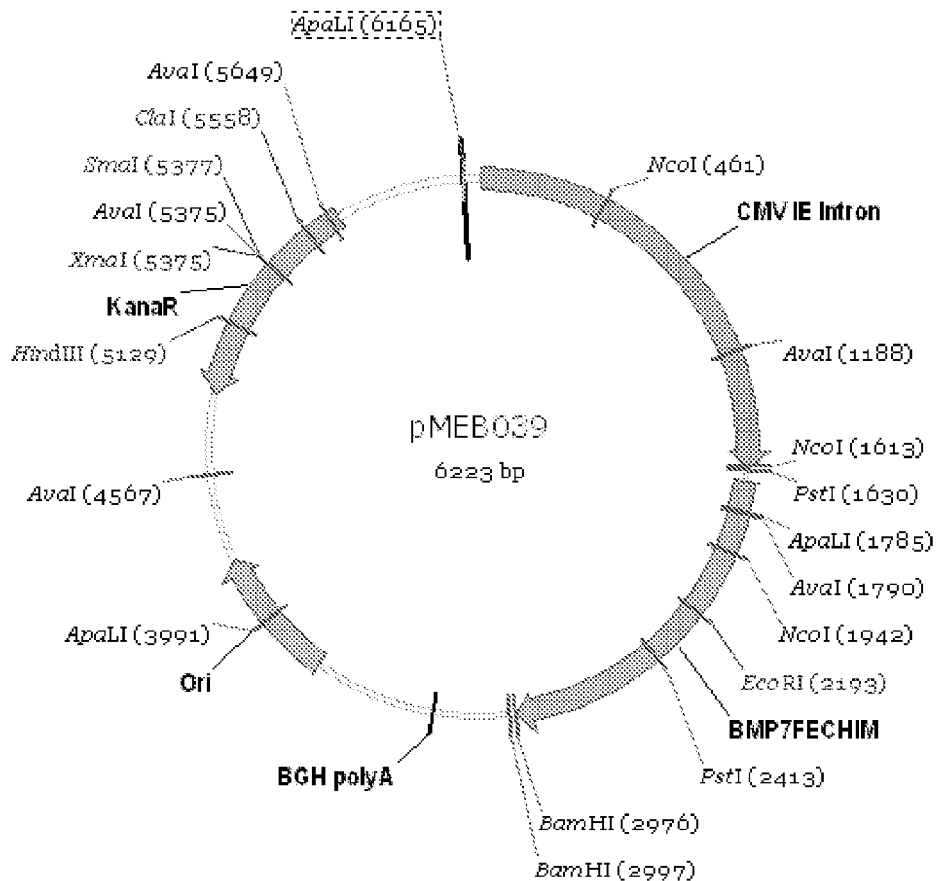
FIG. 6 depicts the pMEB039 plasmid map and the encoded ORF of the feline BMP-7. The nucleotide sequence of the encoded ORF is that of SEQ ID NO: 18 and the amino acid sequence of the encoded ORF is that of SEQ ID NO: 19.

The codon-optimized feline BMP7 open reading frame ("ORF") consists of 1296 by and encodes a 431 amino acids polypeptide (SEQ ID NO: 19). The codon-optimized cDNA, encoding the polypeptide sequence of SEQ ID NO: 18, and flanked by unique EcoRV and XbaI restriction sites, was synthesized from overlapping oligonucleotides, assembled by hybridization and cloned into the pVR1012 plasmid (J. Hartikka et al. Human Gene Therapy 1996, 7, 1205-1217) to generate the pMEB039 plasmid (FIG. 6) in which the expression of the codon-optimized human BMP-7 is driven by the cytomegalovirus immediate early (CMV IE) promoter/enhancer. The nucleotide sequence of the pMEB039 plasmid is that of SEQ ID NO: 20. The pMEB039 plasmid was transformed into DH5α *E. coli* bacteria and subsequently purified using a commercial kit as recommended by the manufacturer (Pure Yield™ Plasmid Midiprep, Promega). Final plasmid concentrations were 2 mg/ml in TE buffer.

The transient in vitro expression of the polypeptide encoded by the pMEB039 plasmid was confirmed and observed after transfection of CHO-K1 cells, using Lipofectamin 2000 (INVITROGEN). CHO-K1 cells at 90% confluence in 6 cm diameter plates were transfected with 5 µg plasmid and 10 µl lipofectamine each, according to the manufacturer's instructions. After transfection, cells were cultivated in MEM-glutamax medium containing 1% foetal calf serum for 24 hours. Cells grown on glass coverslips were washed with PBS, incubated for 10 min in cold acetone for additional fixing and permeabilisation, and again washed in PBS. Recombinant protein production was analysed by indirect immunofluorescence, using an anti-human BMP7 polyclonal serum and monoclonal antibodies (MAB3542, BAM354 and AF354 from R&D Systems, and SC-9305 and SC-6899 from Santa Cruz). The immunochemical method confirmed that the pre-proBMP-7 polypeptide encoded by pMEB039 was expressed in CHO-K1 cells.

Example 5

Therapeutic Effect of BMP-7 Plasmid-Based Gene Therapy After Intra-Vascular Kidney Plasmid Delivery 10 male Sprague-Dawley rats weighting approximately 300-350 g at the initiation of the study were purchased from IFFACREDO (L'Arbresle, France). The maximum and minimum of both temperature and hygrometry of the room were recorded daily. The target temperature and hygrometry range were 20-24° C. and 20-70%, respectively. Light was provided using an automatic timer in cycles of 12 hours light and 12 hours dark. Only healthy rats were included in the study. Rats were allocated randomly to 4 groups of 5 animals each (Groups 1 to 4) and treated as described in Table 4.

TABLE 4

Study design

| Groups | Plasmid | Dose (ml-μg) | Surgery Date* | Glycerol injection date | Buprenorphine injection date | Termination |
|---|---|---|---|---|---|---|
| 1 | gWIZ-SEAP ® | 1-200 | D – 3 | D0 | D0, D1, D2 | D4 |
| 2 | pMEB038 | 1-200 | D – 3 | D0 | D0, D1, D2 | D4 |

*Date of intra-vascular kidney injection

The plasmid gWIZ-SEAP® expressing the control transgene SEAP was purchased from GTS Inc. (San Diego, USA) and used as a placebo. The pMEB038 plasmid was constructed according to example 3.

The rats were anesthetized by a mixture of isoflurane (AERANE®, France, 0 to 5%) and oxygen inhalation. Prior to the surgery, a subcutaneous injection of buprenorphine (TEMGESIC®, Pfizer, France, 0.1 mg/kg) was administered for analgesia.

The skin over the surgical area was scrubbed with povidone iodine. A medial laparotomy was performed. The abdominal organs were gently moved to the right side. The left renal vein was clamped with ongled-type Diethrich bulldog clamps. The adrenal vein was not occluded. Using a 24-gauge SURFLO® intravenous catheter, 1 mL of the appropriate composition (see Table 4) was quickly injected into the left renal vein (the total duration of the injection should be less than 2 seconds). The blood flow was re-established immediately after the injection. To avoid the possibility of narrowing the internal diameter of the renal vein, there was no pull on the kidney as the needle is inserted. Haemostasis was performed by applying a slight pressure on the injected site for 10 seconds. The abdominal wall and skin were sutured in layers with degradable sutures. A dressing was applied to the wound and the animals were closely monitored until completely recovered from anaesthesia.

The animals received an injection of glycerol (50%) at a dose of 7 mL/kg via the intramuscular route. The total volume of glycerol was distributed in both tight muscles. A subcutaneous injection of buprenorphine was administered at D1 and D2.

At D4, the animals of all groups were weighed and anesthetized by intramuscular injection of tiletamine-zolazepam (ZOLETIL® 100—20 to 50 mg/kg, Virbac, France). Blood samples were performed and used for serum creatinine dosage (Laboratoire VETFRANCE, Evry, France) and plasma collection. Plasma was prepared as quickly as possible and immediately stored at −20° C. The animals were then euthanized by intravenous injection of pentobarbital (DOLETHAL®, Vetoquinol, France). The kidneys were harvested and examined macroscopically.

Figure 7:
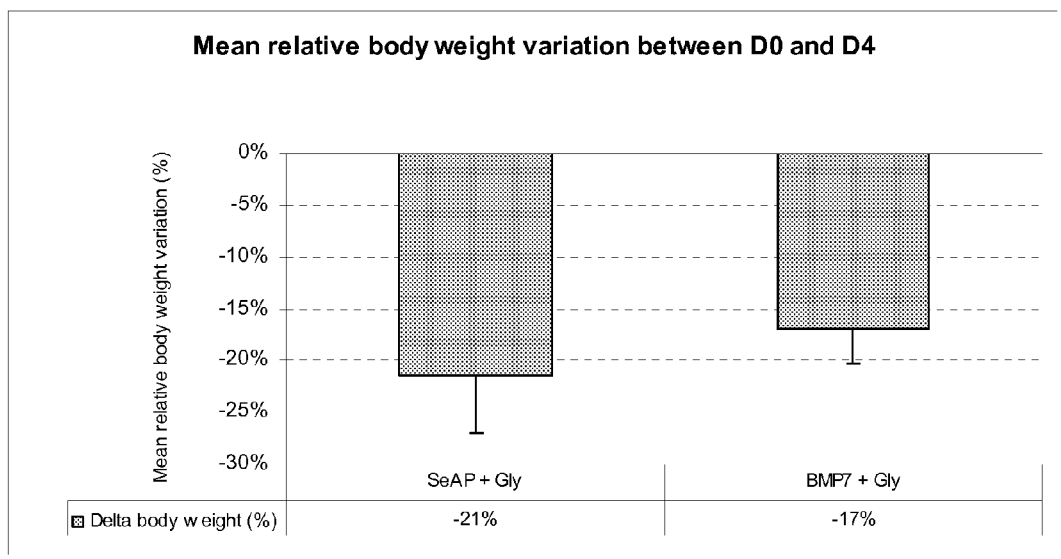
FIG. 7 provides histograms of the mean relative body weight variations of animals of each group between D0 and D4, expressed in percentage.

FIG. 7 provides histograms of the mean relative body weight variations of animals of each group between D0 and D4, expressed in percentage. Partial protection against body weight loss is achieved in rats treated with the BMP7 plasmid by the retrograde hemodynamic intra renal vein injection technique.

Figure 8:
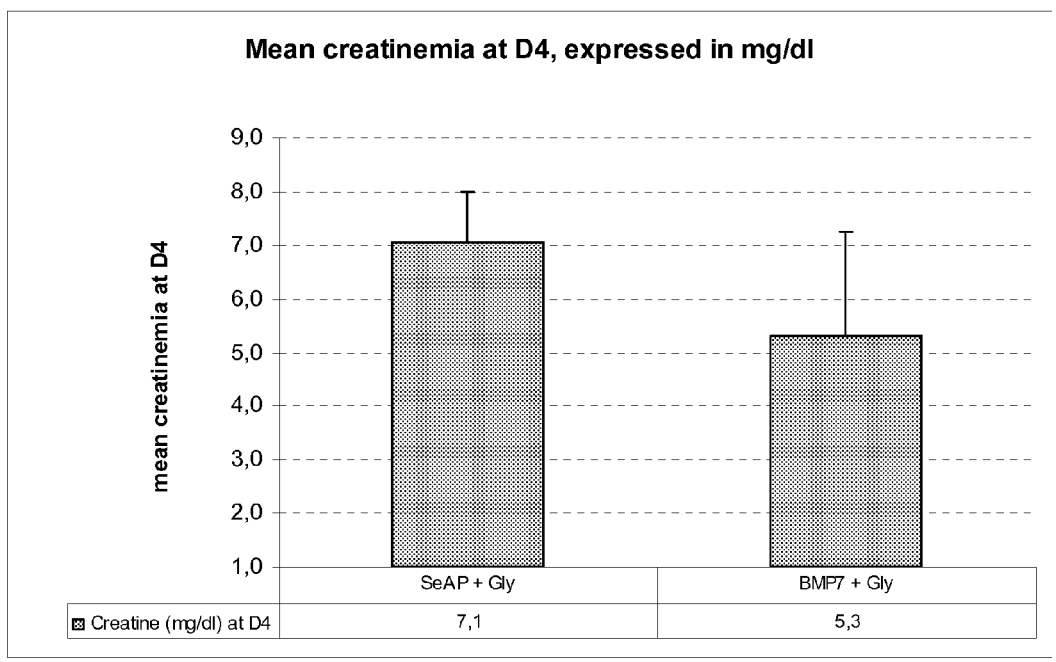
FIG. 8 provides histograms of the mean creatinemia of animals of each group at D4, expressed in milligrams per deciliter.

FIG. 8 provides histograms of the mean creatinemia of animals of each group at D4, expressed in milligrams per deciliter. Partial protection against creatinemia increase is achieved in rats treated with the BMP7 plasmid by the retrograde hemodynamic intra renal vein injection technique.

This data clearly demonstrates the clinical effect of BMP-7 plasmid-based gene therapy administered using a retrograde hemodynamic intra renal vein injection technique in a relevant model of renal pathology.

The invention is further described by the following numbered paragraphs:

1. A method of treating a mammalian subject suffering from, or at risk of developing, renal failure, comprising, administering to said mammalian subject a therapeutically effective amount of a plasmid containing a nucleic acid sequence encoding a BMP-7 polypeptide operatively linked to a promoter, wherein the BMP-7 polypeptide is expressed in vivo in the mammalian subject.

2. The method according to paragraph 1, wherein the mammalian subject is selected from the group consisting of human, canine animal and feline animal.

3. The method according to paragraph 1 wherein the mammalian subject is a dog, a bitch or a puppy.

4. The method according to paragraph 1 wherein the mammalian subject is a cat or a kitten.

5. The method according to paragraph 1 wherein the mammalian subject is suffering from, or are at risk of developing acute renal failure.

6. The method according to paragraph 1 wherein the mammalian subjects are suffering from, or are at risk of developing chronic renal failure.

7. The method according to paragraph 1, wherein the BMP-7 polypeptide is selected from the group consisting of a pre-pro BMP-7 polypeptide, a pro-BMP-7 polypeptide, and a mature BMP-7 polypeptide.

8. The method according to paragraph 1, wherein the BMP-7 polypeptide is selected from the group consisting of a canine pre-pro BMP-7 polypeptide, a canine pro-BMP-7 polypeptide, a canine mature BMP-7 polypeptide, a feline pre-pro BMP-7 polypeptide, a feline pro-BMP-7 polypeptide, a feline mature BMP-7 polypeptide, a human pre-pro BMP-7 polypeptide, a human pro-BMP-7 polypeptide, and a human mature BMP-7 polypeptide.

9. The method according to paragraph 1, wherein the nucleic acid sequence encoding the BMP-7 polypeptide is selected from the group consisting of SEQ ID NO: 1, SEQ ID NO: 2, SEQ ID NO: 13, SEQ ID NO: 14, SEQ ID NO: 17, SEQ ID NO: 18, and fragments, variants, derivatives and homologs thereof that encode polypeptides having BMP-7 activity.

10. The method according to paragraph 1, wherein the BMP-7 polypeptide has an amino acid sequence selected from the group consisting of SEQ ID NO: 3, SEQ ID NO: 15, SEQ ID NO: 19, and fragments, variants, derivatives and homologs thereof having BMP-7 activity.

11. The method according to paragraph 1, wherein the BMP-7 polypeptide comprises a signal peptide.

12. The method according to paragraph 11, wherein the signal peptide is selected from the group consisting of the BMP-7 signal sequence, the IGF-1 signal sequence, and the tPA signal sequence.

13. The method according to paragraph 11, wherein the signal peptide is encoded by a nucleotide sequence selected from the group consisting of SEQ ID NO: 4, SEQ ID NO: 6, SEQ ID NO: 8, SEQ ID NO: 11, and fragments, variants, derivatives and homologs thereof that encode peptides having signal peptide activity.

14. The method according to paragraph 11, wherein the signal peptide has an amino acid sequence selected from the group consisting of SEQ ID NO: 5, SEQ ID NO: 7, SEQ ID NO: 9, SEQ ID NO: 12, and fragments, variants, derivatives and homologs thereof having signal peptide activity.

15. The method according to paragraph 1 wherein the promoter is selected from the group consisting of a CMV IE promoter, a RSV promoter, an HSV-1 TK promoter, a SV40 early promoter, a SV40 late promoter, an adenovirus major late promoter, a phosphoglycerate kinase gene promoter, a metallothionein gene promoter, an α-1 antitrypsin gene promoter, an albumin gene promoter, a collagenase gene promoter, an elastase I gene promoter, a β-actin gene promoter, a β-globin gene promoter, a γ-globin gene promoter, an α-fetoprotein gene promoter, and a muscle creatin kinase gene promoter.

16. The method according to paragraph 1, wherein the plasmid is pNB292 and has the nucleotide sequence of SEQ ID NO: 10.

17. The method according to paragraph 1, wherein the plasmid is pMEB038 and has the nucleotide sequence of SEQ ID NO: 16.

18. The method according to paragraph 1, wherein the plasmid is pMEB039 and has the nucleotide sequence of SEQ ID NO: 20.

19. The method according to paragraph 1, wherein the plasmid comprises the nucleic acid sequence encoding the BMP-7 polypeptide inserted into the VR1012 plasmid.

20. A method of treating a canine suffering from, or at risk of developing, renal failure, comprising, administering to said canine a therapeutically effective amount of a plasmid containing a nucleic acid sequence encoding a BMP-7 polypeptide operatively linked to a promoter.

21. A method of treating a feline suffering from, or at risk of developing, renal failure, comprising, administering to said feline a therapeutically effective amount of a plasmid containing a nucleic acid sequence encoding a BMP-7 polypeptide operatively linked to a promoter.

22. A method of treating a human suffering from, or at risk of developing, renal failure, comprising, administering to said human a therapeutically effective amount of a plasmid containing a nucleic acid sequence encoding a BMP-7 polypeptide operatively linked to a promoter.

23. The method according to any one of paragraphs 20 to 22, wherein the BMP-7 polypeptide is selected from the group consisting of a pre-pro BMP-7 polypeptide, a pro-BMP-7 polypeptide, and a mature BMP-7 polypeptide.

24. The method according to paragraph 20, wherein the nucleic acid sequence encoding the BMP-7 polypeptide is selected from the group consisting of SEQ ID NO: 1, SEQ ID NO: 2, and fragments, variants, derivatives and homologs thereof that encode polypeptides having BMP-7 activity.

25. The method according to paragraph 20, wherein the BMP-7 polypeptide has an amino acid sequence selected from the group consisting of SEQ ID NO: 3 and fragments, variants, derivatives and homologs thereof having BMP-7 activity.

26. The method according to paragraph 21, wherein the nucleic acid sequence encoding the BMP-7 polypeptide is selected from the group consisting of SEQ ID NO: 17, SEQ ID NO: 18, and fragments, variants, derivatives and homologs thereof that encode polypeptides having BMP-7 activity.

27. The method according to paragraph 21, wherein the BMP-7 polypeptide has an amino acid sequence selected from the group consisting of SEQ ID NO: 19 and fragments, variants, derivatives and homologs thereof having BMP-7 activity.

28. The method according to paragraph 22, wherein the nucleic acid sequence encoding the BMP-7 polypeptide is selected from the group consisting of SEQ ID NO: 13, SEQ ID NO: 14, and fragments, variants, derivatives and homologs thereof that encode polypeptides having BMP-7 activity.

29. The method according to paragraph 22, wherein the BMP-7 polypeptide has an amino acid sequence selected from the group consisting of SEQ ID NO: 15 and fragments, variants, derivatives and homologs thereof having BMP-7 activity.

30. The method according to paragraph 23, wherein the BMP-7 polypeptide comprises a signal peptide.

31. The method according to paragraph 30, wherein the signal peptide is selected from the group consisting of the BMP-7 signal sequence, the IGF-1 signal sequence, and the tPA signal sequence.

32. The method according to paragraph 30, wherein the signal peptide is encoded by a nucleotide sequence selected from the group consisting of SEQ ID NO: 4, SEQ ID NO: 6, SEQ ID NO: 8, SEQ ID NO: 11, and fragments, variants, derivatives and homologs thereof that encode peptides having signal peptide activity.

33. The method according to paragraph 30, wherein the signal peptide has an amino acid sequence selected from the group consisting of SEQ ID NO: 5, SEQ ID NO: 7, SEQ ID NO: 9, SEQ ID NO: 12, and fragments, variants, derivatives and homologs thereof having signal peptide activity.

34. The method according to paragraph 20 wherein the promoter is selected from the group consisting of a CMV IE promoter, a RSV promoter, an HSV-1 TK promoter, a SV40 early promoter, a SV40 late promoter, an adenovirus major late promoter, a phosphoglycerate kinase gene promoter, a metallothionein gene promoter, an α-1 antitrypsin gene promoter, an albumin gene promoter, a collagenase gene promoter, an elastase I gene promoter, a β-actin gene promoter, a β-globin gene promoter, a γ-globin gene promoter, an α-fetoprotein gene promoter, and a muscle creatin kinase gene promoter.

35. The method according to paragraph 20, wherein the plasmid is pNB292 and has the nucleotide sequence of SEQ ID NO: 10.

36. The method according to paragraph 20, wherein the plasmid is pMEB038 and has the nucleotide sequence of SEQ ID NO: 16.

37. The method according to paragraph 20, wherein the plasmid is pMEB039 and has the nucleotide sequence of SEQ ID NO: 20.

38. The method according to paragraph 20, wherein the plasmid comprises the nucleic acid sequence encoding the BMP-7 polypeptide inserted into the VR1012 plasmid.

39. A method of preventing the development of renal failure in a mammalian subject at risk thereof, comprising administering to said mammalian subject a an effective amount of a plasmid vector containing a nucleic acid sequence encoding a BMP-7 polypeptide operatively linked to a promoter.

40. The method according to paragraph 39 wherein the mammalian subject is at risk of developing acute renal failure.

41. The method according to paragraph 39 wherein the mammalian subject is at risk of developing chronic renal failure.

42. The method according to paragraph 39, wherein the BMP-7 polypeptide is selected from the group consisting of a pre-pro BMP-7 polypeptide, a pro-BMP-7 polypeptide, and a mature BMP-7 polypeptide.

43. The method according to paragraph 39, wherein the nucleic acid sequence encoding the BMP-7 polypeptide is selected from the group consisting of SEQ ID NO: 1, SEQ ID NO: 2, SEQ ID NO: 13, SEQ ID NO: 14, SEQ ID NO: 17, SEQ ID NO: 18, and fragments, variants, derivatives and homologs thereof that encode polypeptides having BMP-7 activity.

44. The method according to paragraph 39, wherein the BMP-7 polypeptide has an amino acid sequence selected from the group consisting of SEQ ID NO: 3, SEQ ID NO: 15, SEQ ID NO: 19, and fragments, variants, derivatives and homologs thereof having BMP-7 activity.

45. The method according to paragraph 39, wherein the BMP-7 polypeptide comprises a signal peptide.

46. The method according to paragraph 39, wherein the signal peptide is selected from the group consisting of the BMP-7 signal sequence, the IGF-1 signal sequence, and the tPA signal sequence.

47. The method according to paragraph 46, wherein the signal peptide is encoded by a nucleotide sequence selected from the group consisting of SEQ ID NO: 4, SEQ ID NO: 6, SEQ ID NO: 8, SEQ ID NO: 11, and fragments, variants, derivatives and homologs thereof that encode peptides having signal peptide activity.

48. The method according to paragraph 46, wherein the signal peptide has an amino acid sequence selected from the group consisting of SEQ ID NO: 5, SEQ ID NO: 7, SEQ ID NO: 9, SEQ ID NO: 12, and fragments, variants, derivatives and homologs thereof having signal peptide activity.

49. The method according to paragraph 39, wherein the promoter is selected from the group consisting of a CMV IE promoter, a RSV promoter, an HSV-1 TK promoter, a SV40 early promoter, a SV40 late promoter, an adenovirus major late promoter, a phosphoglycerate kinase gene promoter, a metallothionein gene promoter, an α-1 antitrypsin gene promoter, an albumin gene promoter, a collagenase gene promoter, an elastase I gene promoter, a β-actin gene promoter, a β-globin gene promoter, a γ-globin gene promoter, an α-fetoprotein gene promoter, and a muscle creatin kinase gene promoter.

50. The method according to paragraph 39, wherein the plasmid is pNB292 and has the nucleotide sequence of SEQ ID NO: 10.

51. The method according to paragraph 39, wherein the plasmid is pMEB038 and has the nucleotide sequence of SEQ ID NO: 16.

52. The method according to paragraph 39, wherein the plasmid is pMEB039 and has the nucleotide sequence of SEQ ID NO: 20.

53. The method according to paragraph 39, wherein the plasmid comprises the nucleic acid sequence encoding the BMP-7 polypeptide inserted into the VR1012 plasmid.

54. A recombinant plasmid vector comprising a nucleic acid sequence encoding a BMP-7 polypeptide operatively linked to a promoter.

55. The recombinant plasmid vector according to paragraph 54, wherein the BMP-7 polypeptide is selected from the group consisting of a pre-pro BMP-7 polypeptide, a pro-BMP-7 polypeptide, and a mature BMP-7 polypeptide.

56. The recombinant plasmid vector according to paragraph 54, wherein the nucleic acid sequence encoding the BMP-7 polypeptide is selected from the group consisting of SEQ ID NO: 1, SEQ ID NO: 2, SEQ ID NO: 13, SEQ ID NO: 14, SEQ ID NO: 17, SEQ ID NO: 18, and fragments, variants, derivatives and homologs thereof that encode polypeptides having BMP-7 activity.

57. The recombinant plasmid vector according to paragraph 54, wherein the BMP-7 polypeptide has an amino acid sequence selected from the group consisting of SEQ ID NO: 3, SEQ ID NO: 15, SEQ ID NO: 19, and fragments, variants, derivatives and homologs thereof having BMP-7 activity.

58. The recombinant plasmid vector according to paragraph 54, wherein the BMP-7 polypeptide comprises a signal peptide.

59. The recombinant plasmid vector according to paragraph 58, wherein the signal peptide is selected from the group consisting of the BMP-7 signal sequence, the IGF-1 signal sequence, and the tPA signal sequence.

60. The recombinant plasmid vector according to paragraph 58, wherein the signal peptide is encoded by a nucleotide sequence selected from the group consisting of SEQ ID NO: 4, SEQ ID NO: 6, SEQ ID NO: 8, SEQ ID NO: 11, and fragments, variants, derivatives and homologs thereof that encode peptides having signal peptide activity.

61. The recombinant plasmid vector according to paragraph 58, wherein the signal peptide has an amino acid sequence selected from the group consisting of SEQ ID NO: 5, SEQ ID NO: 7, SEQ ID NO: 9, SEQ ID NO: 12, and fragments, variants, derivatives and homologs thereof having signal peptide activity.

62. The recombinant plasmid vector according to paragraph 54, wherein the promoter is selected from the group consisting of a CMV IE promoter, a RSV promoter, an HSV-1 TK promoter, a SV40 early promoter, a SV40 late promoter, an adenovirus major late promoter, a phosphoglycerate kinase gene promoter, a metallothionein gene promoter, an α-1 antitrypsin gene promoter, an albumin gene promoter, a collagenase gene promoter, an elastase I gene promoter, a β-actin gene promoter, a β-globin gene promoter, a γ-globin gene promoter, an α-fetoprotein gene promoter, and a muscle creatin kinase gene promoter.

63. The recombinant plasmid vector according to paragraph 54, wherein the plasmid is pNB292 and has the nucleotide sequence of SEQ ID NO: 10.

64. The recombinant plasmid vector according to paragraph 54, wherein the plasmid is pMEB038 and has the nucleotide sequence of SEQ ID NO: 16.

65. The recombinant plasmid vector according to paragraph 54, wherein the plasmid is pMEB039 and has the nucleotide sequence of SEQ ID NO: 20.

66. The recombinant plasmid vector according to paragraph 54, wherein the plasmid comprises the nucleic acid sequence encoding the BMP-7 polypeptide inserted into the VR1012 plasmid.

67. A pharmaceutical composition comprising a recombinant plasmid vector according to anyone of paragraphs to 54 to 66, and at least one pharmaceutically or veterinarily acceptable carrier, excipient, or vehicle.

68. A method of treating a mammalian subject suffering from, or at risk of developing, renal failure, comprising, administering to said mammalian subject a therapeutically effective amount of a plasmid containing a nucleic acid sequence encoding a BMP-7 polypeptide operatively linked to a promoter, wherein the plasmid is administered intrarenally or intra-vascularly into the kidney of said mammalian subject and wherein the BMP-7 polypeptide is expressed in vivo in the mammalian subject.

69. The method according to paragraph 1, wherein the mammalian subject is selected from the group consisting of human, canine animal and feline animal.

70. The method according to paragraph 1 wherein the mammalian subject is a dog, a bitch or a puppy.

71. The method according to paragraph 1 wherein the mammalian subject is a cat or a kitten.

72. The method according to paragraph 1 wherein the mammalian subject is suffering from, or are at risk of developing acute renal failure.

73. The method according to paragraph 1 wherein the mammalian subjects are suffering from, or are at risk of developing chronic renal failure.

74. The method according to paragraph 1, wherein the BMP-7 polypeptide is selected from the group consisting of a pre-pro BMP-7 polypeptide, a pro-BMP-7 polypeptide, and a mature BMP-7 polypeptide.

75. The method according to paragraph 1, wherein the BMP-7 polypeptide is selected from the group consisting of a canine pre-pro BMP-7 polypeptide, a canine pro-BMP-7 polypeptide, a canine mature BMP-7 polypeptide, a feline pre-pro BMP-7 polypeptide, a feline pro-BMP-7 polypeptide, a feline mature BMP-7 polypeptide, a human pre-pro BMP-7 polypeptide, a human pro-BMP-7 polypeptide, and a human mature BMP-7 polypeptide.

76. The method according to paragraph 1, wherein the nucleic acid sequence encoding the BMP-7 polypeptide is selected from the group consisting of SEQ ID NO: 1, SEQ ID NO: 2, SEQ ID NO: 13, SEQ ID NO: 14, SEQ ID NO: 17, SEQ ID NO: 18, and fragments, variants, derivatives and homologs thereof that encode polypeptides having BMP-7 activity.

77. The method according to paragraph 1, wherein the BMP-7 polypeptide has an amino acid sequence selected from the group consisting of SEQ ID NO: 3, SEQ ID NO: 15, SEQ ID NO: 19, and fragments, variants, derivatives and homologs thereof having BMP-7 activity.

78. The method according to paragraph 68, wherein the BMP-7 polypeptide comprises a signal peptide.

79. The method according to paragraph 78, wherein the signal peptide is selected from the group consisting of the BMP-7 signal sequence, the IGF-1 signal sequence, and the tPA signal sequence.

80. The method according to paragraph 78, wherein the signal peptide is encoded by a nucleotide sequence selected from the group consisting of SEQ ID NO: 4, SEQ ID NO: 6, SEQ ID NO: 8, SEQ ID NO: 11, and fragments, variants, derivatives and homologs thereof that encode peptides having signal peptide activity.

81. The method according to paragraph 78, wherein the signal peptide has an amino acid sequence selected from the group consisting of SEQ ID NO: 5, SEQ ID NO: 7, SEQ ID NO: 9, SEQ ID NO: 12, and fragments, variants, derivatives and homologs thereof having signal peptide activity.

82. The method according to paragraph 68 wherein the promoter is selected from the group consisting of a CMV IE promoter, a RSV promoter, an HSV-1 TK promoter, a SV40 early promoter, a SV40 late promoter, an adenovirus major late promoter, a phosphoglycerate kinase gene promoter, a metallothionein gene promoter, an α-1 antitrypsin gene promoter, an albumin gene promoter, a collagenase gene promoter, an elastase I gene promoter, a β-actin gene promoter, a β-globin gene promoter, a γ-globin gene promoter, an α-fetoprotein gene promoter, and a muscle creatin kinase gene promoter.

83. The method according to paragraph 68, wherein the plasmid is pNB292 and has the nucleotide sequence of SEQ ID NO: 10.

84. The method according to paragraph 68, wherein the plasmid is pMEB038 and has the nucleotide sequence of SEQ ID NO: 16.

85. The method according to paragraph 68, wherein the plasmid is pMEB039 and has the nucleotide sequence of SEQ ID NO: 20.

86. The method according to paragraph 68, wherein the plasmid comprises the nucleic acid sequence encoding the BMP-7 polypeptide inserted into the VR1012 plasmid.

87. The method according to paragraph 68, wherein the administration is a hemodynamic-based plasmid DNA gene delivery.

88. The method according to paragraph 87, wherein the delivery is delivery of naked plasmid through intra renal vein injection.

89. The method according to paragraph 87 or 88, wherein the administration is done (i) an occlusion balloon catheter is inserted into the renal vein of the mammalian subject; (ii) the renal vein is occluded by inflation of the balloon; (iii) a dose of from about 0.0005 to 0.5 mg/kg) of the plasmid is rapidly injected into the renal vein with from about 5 to about 25 ml, i.e., from about 0.5 to about 2.5 ml/kg of normal saline buffer to ensure a flow of from about 0.5 to about 3 ml/s; (iv) the balloon occlusion is continued during the rapid injection and stopped from about 10 sec to about 3 min after the injection; (v) the occlusion balloon is removed.

90. The method according to paragraph 89, wherein (iii) the dose is of about 0.2 mg/kg of the plasmid is rapidly injected into the vein with about 15 ml of normal saline buffer.

91. The method according to paragraph 89, wherein (iii) the power injector is used at a flow of about 1 ml/s.

92. The method according to paragraph 89, wherein (iv) the balloon occlusion is continued during the rapid injection and stopped 1 min after the injection.

93. The method according to any paragraph from 87 to 92, wherein the mammalian subject is a canine animal.

94. The method according to paragraph 93, wherein the BMP-7 polypeptide is selected from the group consisting of a canine pre-pro BMP-7 polypeptide, a canine pro-BMP-7 polypeptide, a canine mature BMP-7 polypeptide.

95. The method according to paragraph 94, wherein the plasmid is pNB292 and has the nucleotide sequence of SEQ ID NO: 10.

96. The method according to any paragraph from 87 to 92, wherein the mammalian subject is a feline animal.

97. The method according to paragraph 96, wherein the BMP-7 polypeptide is selected from the group consisting of a feline pre-pro BMP-7 polypeptide, a feline pro-BMP-7 polypeptide, a feline mature BMP-7 polypeptide.

98. The method according to paragraph 97, wherein the plasmid is pMEB039 and has the nucleotide sequence of SEQ ID NO: 20.

99. The method according to any paragraph from 87 to 92, wherein the mammalian subject is a human.

100. The method according to paragraph 99, wherein the BMP-7 polypeptide is selected from the group consisting of a human pre-pro BMP-7 polypeptide, a human pro-BMP-7 polypeptide, a human mature BMP-7 polypeptide.

101. The method according to paragraph 100, wherein the plasmid is pMEB038 and has the nucleotide sequence of SEQ ID NO: 16.

102. The method according to paragraph 1 wherein the mammalian subject is a human.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A recombinant plasmid vector comprising a polynucleotide encoding a BMP-7 polypeptide having at least 99% sequence identity to SEQ ID NO:19.

2. A recombinant plasmid vector comprising a polynucleotide encoding a mature BMP-7 polypeptide having at least 98.5% sequence identity to the amino acid sequence of residues 293-431 of SEQ ID NO:19.

3. The recombinant plasmid vector of claim 1, wherein the polynucleotide has the sequence as set forth in SEQ ID NO: 17 or 18.

4. The recombinant plasmid vector of any one of claims 1, 2, and 3, wherein the BMP-7 polypeptide comprises a heterologous signal peptide.

5. The recombinant plasmid vector of any one of claims 1, 2, and 3, wherein the polynucleotide is operably linked to a promoter.

6. The recombinant plasmid vector of claim 1, wherein the plasmid is pMEB039 having the sequence as set forth in SEQ ID NO:20.

7. The recombinant plasmid vector of claim 5, wherein the promoter is a CMV IE promoter.

8. A method of treating a mammalian subject suffering from, or at risk of developing, renal failure, comprising administering to a portal vein, hepatic vein or renal vein of said mammalian subject a therapeutically effective amount of the recombinant plasmid vector of any one of claims 1, 2, 5, 6 and 7, wherein the recombinant plasmid vector further comprises a cytomegalovirus immediate early (CMV IE) promoter.

9. A pharmaceutical composition comprising a recombinant plasmid vector of any one of claims 1, 2, 5, 6 and 7, and optionally at least one pharmaceutically or veterinarily acceptable carrier, excipient, or vehicle.

* * * * *

SEQUENCE LISTING

<160> NUMBER OF SEQ ID NOS: 20

<210> SEQ ID NO 1
<211> LENGTH: 1296
<212> TYPE: DNA
<213> ORGANISM: Canis sp.

<400> SEQUENCE: 1

| | | | | | |
|---|---|---|---|---|---|
| atgcacgtgc | gctcgccctg | cgccgcggcg | ccccgcagct | tcgtggcgct | ctgggcgccc | 60 |
| ctgctcctgc | tgcgctccgc | cctggccgac | ttcagcctgg | acaacgaggt | gcactcgagc | 120 |
| ttcatccacc | ggcgcctccg | cagccaggag | cggcgggaga | tgcagcgcga | gatcctctct | 180 |
| atcctgggct | tgccccaccg | cccgcgcccg | cacctccagg | gcaagcacaa | ctcggcgccc | 240 |
| atgttcatgc | tggacctgta | caatgccatg | gcggtggagg | agggcggcgg | gcccgacggc | 300 |
| cagggcttct | cctaccccta | caaggccgtc | ttcagcaccc | agggcccccc | tctggccagc | 360 |
| ctgcaagaca | gccacttcct | caccgacgcc | gacatggtca | tgagcttcgt | caacctcgtg | 420 |
| gagcatgaca | aagagttctt | ctatccacgt | taccaccacc | gggagttccg | gttcgatctc | 480 |
| tccaagatcc | agaggggga | agctgtgact | gcagccgaat | tccggatcta | caaggactac | 540 |
| attcgggagc | gcttcgacaa | cgagacgttc | cggatcagcg | tttaccaggt | gctgcaggag | 600 |
| cacttgggca | gggagtcaga | cctgttcctg | ctggacagcc | gcaccctctg | ggcctcggag | 660 |
| gagggctggc | tggtgttcga | catcacagcc | accagcaacc | actgggtggt | caacccacga | 720 |
| cacaacctgg | gcctgcagct | ctgcgtggag | accttggacg | ggcagagcat | caaccccaag | 780 |
| ttggcgggcc | tgatcgggcg | gcacgggccc | cagaacaagc | agcccttcat | ggtggccttc | 840 |
| ttcaaggcca | cggaagtcca | cctccgcagc | acgcgctcca | cggcgccaa | gcagcgcagc | 900 |
| cagaaccgct | ccaagacgcc | caagaaccag | gaagccctgc | gggtggccaa | cgtcgcagaa | 960 |
| aacagcagca | gcgaccagag | gcaggcctgc | aagaagcacg | aactgtacgt | cagcttccgc | 1020 |
| gatctgggct | ggcaggactg | gatcatcgct | cccgaaggct | atgccgctta | ctactgtgag | 1080 |
| ggggagtgtg | ccttccccct | gaactcctac | atgaacgcca | ccaaccacgc | catcgtgcag | 1140 |
| acgctggtcc | acttcatcaa | ccccgaaacg | gtgcccaagc | catgctgtgc | ccccactcag | 1200 |
| ctcaacgcca | tctctgtcct | ctacttcgac | gacagctcca | acgtcatcct | gaagaaatac | 1260 |
| agaaacatgg | tcgtccgagc | ctgtggctgc | cactag | | | 1296 |

<210> SEQ ID NO 2
<211> LENGTH: 1296
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| | | | | | |
|---|---|---|---|---|---|
| atgcatgtgc | gcagcccgtg | cgcggcggcg | ccgcgcagct | ttgtggcgct | gtgggcgccg | 60 |
| ctgctgctgc | tgcgcagcgc | gctggcggat | tttagcctgg | ataacgaagt | gcatagcagc | 120 |
| tttattcatc | gccgcctgcg | cagccaggaa | cgccgcgaaa | tgcagcgcga | aattctgagc | 180 |
| attctgggcc | tgccgcatcg | cccgcgcccg | catctgcagg | gcaaacataa | cagcgcgccg | 240 |
| atgtttatgc | tggatctgta | taacgcgatg | gcggtggaag | aaggcggcgg | cccggatggc | 300 |
| cagggcttta | gctatccgta | taagcgcgtg | tttagcaccc | agggcccgcc | gctggcgagc | 360 |
| ctgcaggata | gccattttct | gaccgatgcg | gatatggtga | tgagctttgt | gaacctggtg | 420 |

```
gaacatgata aagaattttt ttatccgcgc tatcatcatc gcgaatttcg ctttgatctg      480
agcaaaattc cggaaggcga agcggtgacc gcggcggaat tcgcattta taaagattat      540 attcgcgaac gctttgataa cgaaaccttt cgcattagcg tgtatcaggt gctgcaggaa      600
catctgggcc gcgaaagcga tctgtttctg ctggatagcc gcaccctgtg gcgagcgaa      660 gaaggctggc tggtgtttga tattaccgcg accagcaacc attgggtggt gaacccgcgc      720
cataacctgg gcctgcagct gtgcgtggaa acctggatg gccagagcat taacccgaaa       780
ctggcgggcc tgattggccg ccatggcccg cagaacaaac agccgtttat ggtggcgttt      840
tttaaagcga ccgaagtgca tctgcgcagc acccgcagca ccggcgcgaa acagcgcagc      900
cagaaccgca gcaaaacccc gaaaaaccag gaagcgctgc cgtggcgaa cgtggcggaa       960 aacagcagca gcgatcagcg ccaggcgtgc aaaaaacatg aactgtatgt gagctttcgc     1020
gatctgggct ggcaggattg gattattgcg ccggaaggct atgcggcgta ttattgcgaa     1080
ggcgaatgcg cgtttccgct gaacagctat atgaacgcga ccaaccatgc gattgtgcag     1140
accctggtgc attttattaa cccggaaacc gtgccgaaac cgtgctgcgc gccgacccag     1200
ctgaacgcga ttagcgtgct gtattttgat gatagcagca cgtgattct gaaaaaatat      1260 cgcaacatgg tggtgcgcgc gtgcggctgc cattaa                                1296
```

<210> SEQ ID NO 3
<211> LENGTH: 431
<212> TYPE: PRT
<213> ORGANISM: Canis sp.

<400> SEQUENCE: 3

```
Met His Val Arg Ser Pro Cys Ala Ala Ala Pro Arg Ser Phe Val Ala
1               5                   10                  15

Leu Trp Ala Pro Leu Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Asp Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe Tyr Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220
```

```
Val Phe Asp Ile Thr Ala Thr Ser Asn His Trp Val Asn Pro Arg
225                 230                 235                 240

His Asn Leu Gly Leu Gln Leu Cys Val Glu Thr Leu Asp Gly Gln Ser
            245                 250                 255

Ile Asn Pro Lys Leu Ala Gly Leu Ile Gly Arg His Gly Pro Gln Asn
        260                 265                 270

Lys Gln Pro Phe Met Val Ala Phe Phe Lys Ala Thr Glu Val His Leu
    275                 280                 285

Arg Ser Thr Arg Ser Thr Gly Ala Lys Gln Arg Ser Gln Asn Arg Ser
290                 295                 300

Lys Thr Pro Lys Asn Gln Glu Ala Leu Arg Val Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 4
<211> LENGTH: 69
<212> TYPE: DNA
<213> ORGANISM: Homo sapiens

<400> SEQUENCE: 4
atggatgcaa tgaagagagg gctctgctgt gtgctgctgc tgtgtggagc agtcttcgtt       60
tcgcccagc                                                              69

<210> SEQ ID NO 5
<211> LENGTH: 23
<212> TYPE: PRT
<213> ORGANISM: Homo sapiens

<400> SEQUENCE: 5

Met Asp Ala Met Lys Arg Gly Leu Cys Cys Val Leu Leu Leu Cys Gly
1               5                   10                  15

Ala Val Phe Val Ser Pro Ser
            20

<210> SEQ ID NO 6
<211> LENGTH: 84
<212> TYPE: DNA
<213> ORGANISM: Homo sapiens

<400> SEQUENCE: 6
atggatgcaa tgaagagagg gctctgctgt gtgctgctgc tgtgtggagc agtcttcgtt       60
tcgcccagcc aggaaatcca tgcc                                             84

<210> SEQ ID NO 7
```

```
<211> LENGTH: 28
<212> TYPE: PRT
<213> ORGANISM: Homo sapiens

<400> SEQUENCE: 7

Met Asp Ala Met Lys Arg Gly Leu Cys Cys Val Leu Leu Leu Cys Gly
1               5                   10                  15

Ala Val Phe Val Ser Pro Ser Gln Glu Ile His Ala
            20                  25

<210> SEQ ID NO 8
<211> LENGTH: 75
<212> TYPE: DNA
<213> ORGANISM: Equus sp.

<400> SEQUENCE: 8
atgcacatca tgagcagcag ccacctgttc tacctggccc tgtgcctgct gaccttcacc      60
agcagcgcca ccgcc                                                      75

<210> SEQ ID NO 9
<211> LENGTH: 25
<212> TYPE: PRT
<213> ORGANISM: Equus sp.

<400> SEQUENCE: 9

Met His Ile Met Ser Ser Ser His Leu Phe Tyr Leu Ala Leu Cys Leu
1               5                   10                  15

Leu Thr Phe Thr Ser Ser Ala Thr Ala
            20                  25

<210> SEQ ID NO 10
<211> LENGTH: 6193
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 10
ttggctattg gccattgcat acgttgtatc catatcataa tatgtacatt tatattggct      60
catgtccaac attaccgcca tgttgacatt gattattgac tagttattaa tagtaatcaa     120
ttacggggtc attagttcat agcccatata tggagttccg cgttacataa cttacggtaa     180
atggcccgcc tggctgaccg cccaacgacc cccgcccatt gacgtcaata atgacgtatg     240
ttcccatagt aacgccaata gggactttcc attgacgtca atgggtggag tatttacggt     300
aaactgccca cttggcagta catcaagtgt atcatatgcc aagtacgccc cctattgacg     360
tcaatgacgg taaatggccc gcctggcatt atgcccagta catgacctta tgggactttc     420
ctacttggca gtacatctac gtattagtca tcgctattac catggtgatg cggttttggc     480
agtacatcaa tgggcgtgga tagcggtttg actcacgggg atttccaagt ctccacccca     540
ttgacgtcaa tgggagtttg ttttggcacc aaaatcaacg ggactttcca aaatgtcgta     600
acaactccgc cccattgacg caaatgggcg gtaggcgtgt acggtgggag gtctatataa     660
gcagagctcg tttagtgaac cgtcagatcg cctggagacg ccatccacgc tgttttgacc     720
tccatagaag acaccgggac cgatccagcc tccgcggccg ggaacggtgc attggaacgc     780
ggattccccg tgccaagagt gacgtaagta ccgcctatag actctatagg cacacccctt     840
tggcttctta tgcatgctat actgttttg gcttggggcc tatacacccc cgcttcctta     900
tgctataggt gatggtatag cttagcctat aggtgtgggt tattgaccat tattgaccac     960
```

```
tcccctattg gtgacgatac tttccattac taatccataa catggctctt tgccacaact   1020
atctctattg gctatatgcc aatactctgt ccttcagaga ctgacacgga ctctgtattt   1080
ttacaggatg gggtcccatt tattatttac aaattcacat atacaacaac gccgtccccc   1140
gtgcccgcag ttttttattaa acatagcgtg ggatctccac gcgaatctcg ggtacgtgtt   1200
ccggacatgg gctcttctcc ggtagcggcg gagcttccac atccgagccc tggtcccatg   1260
cctccagcgg ctcatggtcg ctcggcagct ccttgctcct aacagtggag gccagactta   1320
ggcacagcac aatgcccacc accaccagtg tgccgcacaa ggccgtggcg gtagggtatg   1380
tgtctgaaaa tgagcgtgga gattgggctc gcacggctga cgcagatgga agacttaagg   1440
cagcggcaga agaagatgca ggcagctgag ttgttgtatt ctgataagag tcagaggtaa   1500
ctcccgttgc ggtgctgtta acggtggagg gcagtgtagt ctgagcagta ctcgttgctg   1560
ccgcgcgcgc caccagacat aatagctgac agactaacag actgttcctt tccatgggtc   1620
ttttctgcag tcaccgtcgt cgacgccacc atgcacgtga gaagccctg tgccgccgct   1680 cccagaagct tcgtggccct gtgggcccct ctgctgctgc tgagatccgc cctggccgat   1740
ttcagcctgg acaacgaggt gcacagcagc ttcatccacc ggaggctgag aagccaagaa   1800
cgcagggaga tgcagagaga gatcctgagc atcctgggcc tgcctcacag acccagaccc   1860
cacctgcagg gcaagcacaa tagcgccccc atgttcatgc tggacctgta caacgccatg   1920
gccgtggagg agggcggagg acccgacggc cagggcttca gctacccta caaggccgtg   1980 ttcagcaccc agggccctcc tctgccagc ctgcaggata gccacttcct gaccgacgcc   2040
gacatggtga tgagcttcgt gaacctggtg gagcacgaca aggagttctt ctaccccaga   2100
taccaccacc gggagttcag attcgacctg agcaagatcc ccgagggcga ggccgtgaca   2160
gccgccgagt tccggatcta caaggactac atccgggagc gcttcgacaa cgagaccttc   2220
cggatcagcg tgtaccaggt gctgcaggag cacctgggca gagagagcga tctgttcctg   2280
ctggacagca gaacactgtg ggccagcgag gagggctggc tggtgttcga catcaccgcc   2340
acctccaatc actgggtggt gaaccccaga cacaatctgg gcctgcagct gtgtgtggag   2400
accctggatg ccagagcat caaccccaag ctggccggcc tgatcggcag acacggcccc   2460
cagaacaagc agcctttcat ggtggccttt tcaaggcca ccgaggtgca cctgagaagc   2520
accagaagca caggcgccaa gcagaggagc cagaacagaa gcaagacccc caagaaccag   2580
gaggccctga gagtggccaa tgtggccgag aacagcagca gcgatcagag gcaggcctgt   2640
aagaagcacg agctgtacgt gtccttcaga gacctgggct ggcaggattg gatcatcgcc   2700
cccgagggct acgccgccta ctactgtgag ggcgagtgtg ccttccccct gaacagctac   2760
atgaacgcca ccaaccacgc catcgtgcag accctggtgc acttcatcaa ccccgagacc   2820
gtgcccaagc cctgctgtgc ccctacccag ctgaatgcca tcagcgtgct gtacttcgac   2880
gacagcagca acgtgatcct gaagaaatac cggaacatgg tggtgagagc ctgtggctgc   2940
cactaataat tctagaccag gccctggatc cagatctgct gtgccttcta gttgccagcc   3000
atctgttgtt tgcccctccc ccgtgccttc cttgaccctg gaaggtgcca ctcccactgt   3060
cctttcctaa taaaatgagg aaattgcatc gcattgtctg agtaggtgtc attctattct   3120
ggggggtggg gtggggcagg acagcaaggg ggaggattgg gaagacaata gcaggcatgc   3180
tggggatgcg gtgggctcta tgggtaccca ggtgctgaag aattgacccg gttcctcctg   3240
ggccagaaaa agcaggcac atccccttct ctgtgacaca ccctgtccac gcccctggtt   3300
cttagttcca gccccactca taggacactc atagctcagg agggctccgc cttcaatccc   3360
```

```
acccgctaaa gtacttggag cggtctctcc ctccctcatc agcccaccaa accaaaccta   3420
gcctccaaga gtgggaagaa attaaagcaa gataggctat taagtgcaga gggagagaaa   3480
atgcctccaa catgtgagga agtaatgaga gaaatcatag aatttcttcc gcttcctcgc   3540
tcactgactc gctgcgctcg gtcgttcggc tgcggcgagc ggtatcagct cactcaaagg   3600
cggtaatacg gttatccaca gaatcagggg ataacgcagg aaagaacatg tgagcaaaag   3660
gccagcaaaa ggccaggaac cgtaaaaagg ccgcgttgct ggcgtttttc cataggctcc   3720
gcccccctga cgagcatcac aaaaatcgac gctcaagtca gaggtggcga aacccgacag   3780
gactataaag ataccaggcg tttccccctg gaagctccct cgtgcgctct cctgttccga   3840
ccctgccgct taccggatac ctgtccgcct ttctcccttc gggaagcgtg gcgctttctc   3900
atagctcacg ctgtaggtat ctcagttcgg tgtaggtcgt tcgctccaag ctgggctgtg   3960
tgcacgaacc cccgttcag cccgaccgct gcgccttatc cggtaactat cgtcttgagt   4020
ccaacccggt aagacacgac ttatcgccac tggcagcagc cactggtaac aggattagca   4080
gagcgaggta tgtaggcggt gctacagagt tcttgaagtg gtggcctaac tacggctaca   4140
ctagaagaac agtatttggt atctgcgctc tgctgaagcc agttaccttc ggaaaaagag   4200
ttggtagctc ttgatccggc aaacaaacca ccgctggtag cggtggtttt tttgtttgca   4260
agcagcagat tacgcgcaga aaaaaaggat ctcaagaaga tcctttgatc ttttctacgg   4320
ggtctgacgc tcagtggaac gaaaactcac gttaagggat tttggtcatg agattatcaa   4380
aaaggatctt cacctagatc cttttaaatt aaaaatgaag ttttaaatca atctaaagta   4440
tatatgagta aacttggtct gacagttacc aatgcttaat cagtgaggca cctatctcag   4500
cgatctgtct atttcgttca tccatagttg cctgactcgg ggggggggg cgctgaggtc   4560 tgcctcgtga agaaggtgtt gctgactcat accaggcctg aatcgcccca tcatccagcc   4620
agaaagtgag ggagccacgg ttgatgagag ctttgttgta ggtggaccag ttggtgattt   4680
tgaacttttg ctttgccacg gaacggtctg cgttgtcggg aagatgcgtg atctgatcct   4740
tcaactcagc aaaagttcga tttattcaac aaagccgccg tcccgtcaag tcagcgtaat   4800
gctctgccag tgttacaacc aattaaccaa ttctgattag aaaaactcat cgagcatcaa   4860
atgaaactgc aatttattca tatcaggatt atcaatacca tttttgaa aaagccgttt   4920 ctgtaatgaa ggagaaaact caccgaggca gttccatagg atggcaagat cctggtatcg   4980
gtctgcgatt ccgactcgtc caacatcaat acaacctatt aatttcccct cgtcaaaaat   5040
aaggttatca agtgagaaat caccatgagt gacgactgaa tccggtgaga atggcaaaag   5100
cttatgcatt tctttccaga cttgttcaac aggccagcca ttacgctcgt catcaaaatc   5160
actcgcatca accaaaccgt tattcattcg tgattgcgcc tgagcgagac gaaatacgcg   5220
atcgctgtta aaaggacaat acaaacagg atcgaatgc aaccggcgca ggaacactgc   5280
cagcgcatca acaatatttt cacctgaatc aggatattct tctaatacct ggaatgctgt   5340
tttcccgggg atcgcagtgg tgagtaacca tgcatcatca ggagtacgga taaaatgctt   5400
gatggtcgga agaggcataa attccgtcag ccagtttagt ctgaccatct catctgtaac   5460
atcattggca acgctacctt tgccatgttt cagaaacaac tctggcgcat cgggcttccc   5520
atacaatcga tagattgtcg cacctgattg cccgacatta tcgcgagccc atttataccc   5580
atataaatca gcatccatgt tggaatttaa tcgcggcctc gagcaagacg tttcccgttg   5640
aatatggctc ataacacccc ttgtattact gtttatgtaa gcagacagtt ttattgttca   5700
tgatgatata ttttatctt gtgcaatgta acatcagaga ttttgagaca caacgtggct   5760
```

```
ttccccccc cccattatt gaagcattta tcagggttat tgtctcatga gcggatacat      5820
atttgaatgt atttagaaaa ataaacaaat aggggttccg cgcacatttc cccgaaaagt      5880
gccacctgac gtctaagaaa ccattattat catgacatta acctataaaa ataggcgtat      5940
cacgaggccc tttcgtctcg cgcgtttcgg tgatgacggt gaaaacctct gacacatgca      6000
gctcccggag acggtcacag cttgtctgta agcggatgcc gggagcagac aagcccgtca      6060
gggcgcgtca gcgggtgttg gcgggtgtcg gggctggctt aactatgcgg catcagagca      6120
gattgtactg agagtgcacc atatgcggtg tgaaataccg cacagatgcg taaggagaaa      6180
ataccgcatc aga                                                        6193
```

<210> SEQ ID NO 11
<211> LENGTH: 75
<212> TYPE: DNA
<213> ORGANISM: Canis sp.

<400> SEQUENCE: 11

```
atgcacaccg tgtcctcctc gcacctcttc tacctggcac tgtgcttgct caccttcccc       60
agccccgcca cagct                                                         75
```

<210> SEQ ID NO 12
<211> LENGTH: 25
<212> TYPE: PRT
<213> ORGANISM: Canis sp.

<400> SEQUENCE: 12

Met His Thr Val Ser Ser Ser His Leu Phe Tyr Leu Ala Leu Cys Leu
1               5                   10                  15

Leu Thr Phe Pro Ser Pro Ala Thr Ala
            20                  25

<210> SEQ ID NO 13
<211> LENGTH: 1296
<212> TYPE: DNA
<213> ORGANISM: Homo sapiens

<400> SEQUENCE: 13

```
atgcacgtgc gctcactgcg agctgcggcg ccgcacagct tcgtggcgct ctgggcaccc       60
ctgttcctgc tgcgctccgc cctggccgac ttcagcctgg acaacgaggt gcactcgagc      120
ttcatccacc ggcgcctccg cagccaggag cggcgggaga tgcagcgcga gatcctctcc      180
attttgggct gccccaccg cccgcgcccg cacctccagg gcaagcacaa ctcggcaccc      240
atgttcatgc tggacctgta caacgccatg gcggtggagg agggcggcgg gcccggcggc      300
cagggcttct cctacccta caaggccgtc ttcagtaccc agggccccc tctggccagc      360 ctgcaagata gccatttcct caccgacgcc gacatggtca tgagcttcgt caacctcgtg      420
gaacatgaca aggaattctt ccaccacgc taccaccatc gagagttccg gtttgatctt      480
tccaagatcc cagaagggga agctgtcacg cagccgaat tccggatcta caaggactac      540
atccgggaac gcttcgacaa tgagacgttc cggatcagcg tttatcaggt gctccaggag      600
cacttgggca gggaatcgga tctcttcctg ctcgacagcc gtaccctctg ggcctcggag      660
gagggctggc tggtgtttga catcacagcc accagcaacc actgggtggt caatccgcgg      720
cacaacctgg gcctgcagct ctcggtggag acgctggatg ggcagagcat caaccccaag      780 ttggcgggc tgattgggcg gcacgggccc cagaacaagc agcccttcat ggtggctttc      840
ttcaaggcca cggaggtcca cttccgcagc atccggtcca cggggagcaa acagcgcagc      900
```

```
cagaaccgct ccaagacgcc caagaaccag gaagccctgc ggatggccaa cgtggcagag    960
aacagcagca gcgaccagag gcaggcctgt aagaagcacg agctgtatgt cagcttccga   1020
gacctgggct ggcaggactg gatcatcgcg cctgaaggct acgccgccta ctactgtgag   1080
ggggagtgtg ccttccctct gaactcctac atgaacgcca ccaaccacgc catcgtgcag   1140
acgctggtcc acttcatcaa cccggaaacg gtgcccaagc cctgctgtgc cccacgcag    1200 ctcaatgcca tctccgtcct ctacttcgat gacagctcca acgtcatcct gaagaaatac   1260
agaaacatgg tggtccgggc ctgtggctgc cactag                             1296
```

```
<210> SEQ ID NO 14
<211> LENGTH: 1299
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atgcacgtgc ggagcctgag agccgctgcc ccccacagct tcgtggccct gtgggcccct    60
ctgttcctgc tgcggagcgc cctggccgac ttcagcctgg acaacgaggt gcacagcagc   120
ttcatccacc ggcggctgcg gagccaggaa cggcgggaga tgcagcggga gatcctgagc   180
atcctgggcc tgcctcaccg gcccaggcct cacctgcagg gcaagcacaa cagcgccccc   240
atgttcatgc tggacctgta caacgccatg gccgtggagg aaggcggcgg acctggcggc   300
cagggcttca gctaccccta caaggccgtg ttcagcacac agggccctcc tctggccagc   360
ctgcaggaca gccacttcct gaccgacgcc gacatggtga tgagcttcgt gaacctggtg   420
gagcacgaca aagagttctt ccaccccaga taccaccacc gggagttccg gttcgacctg   480
agcaagatcc ccgagggcga ggccgtgaca gccgccgagt tccggatcta caaggactac   540
atccgggagc ggttcgacaa cgagaccttc cggatcagcg tgtaccaggt gctgcaggaa   600
cacctgggcc gggagagcga cctgtttctg ctggacagcc ggacactgtg gccagcgag    660 gaaggctggc tggtgttcga catcaccgcc acctccaacc actgggtggt gaaccccggg   720
cacaatctgg gcctgcagct gtccgtggag accctggacg ccagagcat caaccccaag    780 ctggccggcc tgatcggcag acacggcccc cagaacaaga gcccttcat ggtggccttt    840 ttcaaggcca ccgaggtgca cttcagaagc atccggtcca ccggcagcaa gcagcggagc   900
cagaacagaa gcaagacccc caagaaccag gaagccctgc ggatggccaa cgtggccgag   960
aacagcagca gcgaccagcg gcaggcctgc aagaagcacg agctgtacgt cagcttccgg   1020
gacctgggct ggcaggactg gatcatcgcc ccgagggct acgccgccta ctactgcgag   1080
ggcgagtgcg ccttcccct gaacagctac atgaacgcca ccaaccacgc catcgtgcag   1140
accctggtgc actttatcaa ccccgagacc gtgcccaagc cctgctgcgc ccccacccag   1200
ctgaacgcca tcagcgtgct gtacttcgac gacagcagca acgtgatcct gaagaaatac   1260
cggaacatgg tggtgcgggc ctgcggctgc cactgataa                          1299
```

```
<210> SEQ ID NO 15
<211> LENGTH: 431
<212> TYPE: PRT
<213> ORGANISM: Homo sapiens

<400> SEQUENCE: 15

Met His Val Arg Ser Leu Arg Ala Ala Ala Pro His Ser Phe Val Ala
1               5                   10                  15
```

```
Leu Trp Ala Pro Leu Phe Leu Leu Arg Ser Ala Leu Ala Asp Phe Ser
             20                  25                  30

Leu Asp Asn Glu Val His Ser Ser Phe Ile His Arg Arg Leu Arg Ser
         35                  40                  45

Gln Glu Arg Arg Glu Met Gln Arg Glu Ile Leu Ser Ile Leu Gly Leu
 50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
             85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
            195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
            275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430
```

```
<210> SEQ ID NO 16
<211> LENGTH: 6209
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 16
ttggctattg gccattgcat acgttgtatc catatcataa tatgtacatt tatattggct      60
catgtccaac attaccgcca tgttgacatt gattattgac tagttattaa tagtaatcaa     120
ttacggggtc attagttcat agcccatata tggagttccg cgttacataa cttacggtaa     180
atggcccgcc tggctgaccg cccaacgacc cccgcccatt gacgtcaata atgacgtatg     240
ttcccatagt aacgccaata gggactttcc attgacgtca atgggtggag tatttacggt     300
aaactgccca cttggcagta catcaagtgt atcatatgcc aagtacgccc cctattgacg     360
tcaatgacgg taaatggccc gcctggcatt atgcccagta catgacctta tgggactttc     420
ctacttggca gtacatctac gtattagtca tcgctattac catggtgatg cggttttggc     480
agtacatcaa tgggcgtgga tagcggtttg actcacgggg atttccaagt ctccacccca     540
ttgacgtcaa tgggagtttg ttttggcacc aaaatcaacg ggactttcca aaatgtcgta     600
acaactccgc cccattgacg caaatgggcg gtaggcgtgt acggtgggag gtctatataa     660
gcagagctcg tttagtgaac cgtcagatcg cctggagacg ccatccacgc tgttttgacc     720
tccatagaag acaccgggac cgatccagcc tccgcggccg gaacggtgc attggaacgc      780 ggattccccg tgccaagagt gacgtaagta ccgcctatag actctatagg cacacccctt     840
tggcttctta tgcatgctat actgtttttg gcttggggcc tatacacccc cgcttcctta     900
tgctataggt gatggtatag cttagcctat aggtgtgggt tattgaccat tattgaccac     960
tcccctattg gtgacgatac tttccattac taatccataa catggctctt tgccacaact    1020
atctctattg gctatatgcc aatactctgt ccttcagaga ctgacacgga ctctgtattt    1080
ttacaggatg gggtcccatt tattatttac aaattcacat atacaacaac gccgccccc     1140 gtgcccgcag tttttattaa acatagcgtg gatctccac gcgaatctcg ggtacgtgtt     1200
ccggacatgg gctcttctcc ggtagcggcg gagcttccac atccgagccc tggtcccatg    1260
cctccagcgg ctcatggtcg ctcggcagct ccttgctcct aacagtggag gccagactta    1320
ggcacagcac aatgcccacc accaccagtg tgccgcacaa ggccgtggcg gtagggtatg    1380
tgtctgaaaa tgagcgtgga gattgggctc gcacggctga cgcagatgga agacttaagg    1440
cagcggcaga agaagatgca ggcagctgag ttgttgtatt ctgataagag tcagaggtaa    1500
ctcccgttgc ggtgctgtta acggtggagg cagtgtagt ctgagcagta ctcgttgctg     1560
ccgcgcgcgc caccagacat aatagctgac agactaacag actgttcctt tccatgggtc    1620
ttttctgcag tcaccgtcgt cgacacgtgt gatcagatat cgccaccatg cacgtgcgga    1680
gcctgagagc cgctgccccc cacagcttcg tggccctgtg ggccctctg ttcctgctgc     1740 ggagcgccct ggccgacttc agcctggaca cgaggtgca cagcagcttc atccaccggc     1800
ggctgcggag ccaggaacgg cgggagatgc agcgggagat cctgagcatc ctgggcctgc    1860
ctcaccggcc caggcctcac ctgcagggca gcacaacag cgcccccatg ttcatgctgg    1920
acctgtacaa cgccatggcc gtggaggaag cggcggacc tggcggccag gcttcagct     1980 accccctacaa ggccgtgttc agcacacagg gccctcctct ggccagcctg caggacagcc    2040
acttcctgac cgacgccgac atggtgatga gcttcgtgaa cctggtggag cacgacaaag    2100
```

```
agttcttcca ccccagatac caccaccggg agttccggtt cgacctgagc aagatccccg   2160
agggcgaggc cgtgacagcc gccgagttcc ggatctacaa ggactacatc cgggagcggt   2220
tcgacaacga gaccttccgg atcagcgtgt accaggtgct gcaggaacac ctgggccggg   2280
agagcgacct gtttctgctg gacagccgga cactgtgggc cagcgaggaa ggctggctgg   2340
tgttcgacat caccgccacc tccaaccact gggtggtgaa ccccggcac aatctgggcc    2400 tgcagctgtc cgtggagacc ctggacggcc agagcatcaa ccccaagctg gccggcctga   2460
tcggcagaca cggcccccag aacaagcagc ccttcatggt ggcctttttc aaggccaccg   2520
aggtgcactt cagaagcatc cggtccaccg gcagcaagca gcggagccag aacagaagca   2580
agacccccaa gaaccaggaa gccctgcgga tggccaacgt ggccgagaac agcagcagcg   2640
accagcggca ggcctgcaag aagcacgagc tgtacgtcag cttccgggac ctgggctggc   2700
aggactggat catcgccccc gagggctacg ccgcctacta ctgcgagggc gagtgcgcct   2760 tcccccctgaa cagctacatg aacgccacca accacgccat cgtgcagacc ctggtgcact   2820
ttatcaaccc cgagaccgtg cccaagccct gctgcgcccc cacccagctg aacgccatca   2880
gcgtgctgta cttcgacgac agcagcaacg tgatcctgaa gaaataccgg aacatggtgg   2940
tgcgggcctg cggctgccac tgataatcta gaccaggccc tggatccaga tctgctgtgc   3000
cttctagttg ccagccatct gttgtttgcc cctcccccgt gccttccttg acctggaag    3060 gtgccactcc cactgtcctt tcctaataaa atgaggaaat tgcatcgcat tgtctgagta   3120
ggtgtcattc tattctgggg ggtggggtgg ggcaggacag caaggggag gattgggaag    3180 acaatagcag gcatgctggg gatgcggtgg gctctatggg tacccaggtg ctgaagaatt   3240
gacccggttc ctcctgggcc agaaagaagc aggcacatcc ccttctctgt gacacaccct   3300
gtccacgccc ctggttctta gttccagccc cactcatagg acactcatag ctcaggaggg   3360
ctccgccttc aatcccaccc gctaaagtac ttggagcggt ctctccctcc ctcatcagcc   3420
caccaaacca aacctagcct ccaagagtgg gaagaaatta aagcaagata ggctattaag   3480
tgcagaggga gagaaaatgc ctccaacatg tgaggaagta atgagagaaa tcatagaatt   3540
tcttccgctt cctcgctcac tgactcgctg cgctcggtcg ttcggctgcg gcgagcggta   3600
tcagctcact caaaggcggt aatacggtta tccacagaat cagggataa cgcaggaaag   3660 aacatgtgag caaaaggcca gcaaaaggcc aggaaccgta aaaaggccgc gttgctggcg   3720 ttttttccata ggctccgccc ccctgacgag catcacaaaa atcgacgctc aagtcagagg  3780
tggcgaaacc cgacaggact ataaagatac caggcgtttc ccctggaag ctccctcgtg    3840 cgctctcctg ttccgaccct gccgcttacc ggatacctgt ccgcctttct cccttcggga   3900
agcgtggcgc tttctcatag ctcacgctgt aggtatctca gttcggtgta ggtcgttcgc   3960
tccaagctgg gctgtgtgca cgaaccccc gttcagcccg accgctgcgc cttatccggt     4020
aactatcgtc ttgagtccaa cccggtaaga cacgacttat cgccactggc agcagccact   4080
ggtaacagga ttagcagagc gaggtatgta ggcggtgcta cagagttctt gaagtggtgg   4140
cctaactacg gctacactag aagaacagta tttggtatct gcgctctgct gaagccagtt   4200
accttcggaa aaagagttgg tagctcttga tccggcaaac aaaccaccgc tggtagcggt   4260
ggtttttttg tttgcaagca gcagattacg cgcagaaaaa aaggatctca agaagatcct   4320
ttgatctttt ctacggggtc tgacgctcag tggaacgaaa actcacgtta agggattttg   4380
gtcatgagat tatcaaaaag gatcttcacc tagatccttt taaattaaaa atgaagtttt   4440
aaatcaatct aaagtatata tgagtaaact tggtctgaca gttaccaatg cttaatcagt   4500
```

-continued

```
gaggcaccta tctcagcgat ctgtctattt cgttcatcca tagttgcctg actcggggg      4560 gggggcgct gaggtctgcc tcgtgaagaa ggtgttgctg actcatacca ggcctgaatc      4620
gccccatcat ccagccagaa agtgagggag ccacggttga tgagagcttt gttgtaggtg      4680
gaccagttgg tgattttgaa cttttgcttt gccacggaac ggtctgcgtt gtcgggaaga      4740
tgcgtgatct gatccttcaa ctcagcaaaa gttcgattta ttcaacaaag ccgccgtccc      4800
gtcaagtcag cgtaatgctc tgccagtgtt acaaccaatt aaccaattct gattagaaaa      4860
actcatcgag catcaaatga aactgcaatt tattcatatc aggattatca ataccatatt      4920
tttgaaaaag ccgtttctgt aatgaaggag aaaactcacc gaggcagttc cataggatgg      4980
caagatcctg gtatcggtct gcgattccga ctcgtccaac atcaatacaa cctattaatt      5040
tcccctcgtc aaaataagg ttatcaagtg agaaatcacc atgagtgacg actgaatccg      5100
gtgagaatgg caaaagctta tgcatttctt ccagacttg ttcaacaggc cagccattac      5160
gctcgtcatc aaaatcactc gcatcaacca aaccgttatt cattcgtgat gcgcctgag      5220 cgagacgaaa tacgcgatcg ctgttaaaag acaattaca acaggaatc gaatgcaacc      5280 ggcgcaggaa cactgccagc gcatcaacaa tattttcacc tgaatcagga tattcttcta      5340
atacctggaa tgctgttttc ccggggatcg cagtggtgag taaccatgca tcatcaggag      5400
tacggataaa atgcttgatg gtcggaagag gcataaattc cgtcagccag tttagtctga      5460
ccatctcatc tgtaacatca ttggcaacgc tacctttgcc atgtttcaga aacaactctg      5520
gcgcatcggg cttcccatac aatcgataga ttgtcgcacc tgattgcccg acattatcgc      5580
gagcccattt atacccatat aaatcagcat ccatgttgga atttaatcgc ggcctcgagc      5640
aagacgtttc ccgttgaata tggctcataa caccccttgt attactgttt atgtaagcag      5700
acagttttat tgttcatgat gatatatttt tatcttgtgc aatgtaacat cagagatttt      5760
gagacacaac gtggctttcc ccccccccc attattgaag catttatcag ggttattgtc      5820
tcatgagcgg atacatattt gaatgtattt agaaaaataa acaaataggg gttccgcgca      5880
catttccccg aaaagtgcca cctgacgtct aagaaaccat tattatcatg acattaacct      5940
ataaaaatag gcgtatcacg aggccctttc gtctcgcgcg tttcggtgat gacggtgaaa      6000
acctctgaca catgcagctc ccggagacgg tcacagcttg tctgtaagcg gatgccggga      6060
gcagacaagc ccgtcagggc gcgtcagcgg gtgttggcgg gtgtcgggc tggcttaact      6120 atgcggcatc agagcagatt gtactgagag tgcaccatat gcggtgtgaa ataccgcaca      6180
gatgcgtaag gagaaaatac cgcatcaga                                       6209
```

<210> SEQ ID NO 17
<211> LENGTH: 1296
<212> TYPE: DNA
<213> ORGANISM: Felis catus

<400> SEQUENCE: 17

```
atgcacgtgc gctcgctgcg cgccgcggcg ccccacagct tcgtggcgct ctgggcgccc       60
ctgttcctgc tgcgctccgc cctggccgac ttcagcctgg acaacgaggt gcactcgagc      120
ttcatccacc ggcgcctccg cagccaggag cggcgggaga tgcagcgcga tcctctctct      180
atcttgggct tgccccatcg cccgcgcccc cacctccagg gcaagcacaa ctcggcgccc      240
atgttcatgc tggacctgta caacgccatg gcggtggagg agggcggcgg gcccgacggc      300
cagggcttct cctaccccta caaggccgtc ttcagtaccc agggccccc tctgccagc       360 ctgcaagata gccgcttcct caccgacgcc gacatggtca tgagcttcgt caacctcgtg      420
```

| | |
|---|---:|
| gagcacgaca aagagttctt ccacccacgt taccaccacc gggagttccg gtttgatctt | 480 |
| tccaagatcc cagaagggga agccgtgacc gcagccgaat tccgcatcta caaggactac | 540 |
| atccgggaac gctttgataa tgagacgttc cggatcagcg tttaccaggt gcttcaggag | 600 |
| cacttgggca gggagtccga cctgttcctg ctggacagcc gcacgctctg ggcctcggag | 660 |
| gagggctggc tggtgttcga catcacggcc accagcaacc actgggtggt caacccgcgg | 720 |
| cacaatctgg gcctgcagct ctgcgtggag accttggacg ggcagagcat caaccccaag | 780 |
| ttggcgggcc tgatcgggag gcacgggccc cagaacaagc agcccttcat ggtggccttc | 840 |
| ttcaaggcca cggaggtcca ccttcgcagc acccgctcca caggggggcaa gcaacgcagc | 900 |
| cagaaccgct ccaagacgcc caagaaccag gaagccctgc gggtgaccaa cgtcgcagaa | 960 |
| aacagcagca gtgaccagag gcaggcttgt aagaagcacg agctgtacgt cagcttccgc | 1020 |
| gacctgggct ggcaggactg gatcatcgct cccgaaggct atgctgctta ctactgcgag | 1080 |
| ggggagtgtg ccttccctct gaactcctac atgaacgcca ccaaccacgc catcgtgcag | 1140 |
| acgctggtcc acttcatcaa cccggagacg gtgcccaagc cgtgctgtgc ccccacgcag | 1200 |
| ctcaacgcca tctctgtgct ctacttcgac gacagctcca acgtcatcct gaagaaatac | 1260 |
| agaaacatgg tcgtccgagc ctgtggctgc cactag | 1296 |

<210> SEQ ID NO 18
<211> LENGTH: 1299
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

| | |
|---|---:|
| atgcacgtgc gctcactgcg agctgcggcg ccgcacagct tcgtggcgct ctgggcaccc | 60 |
| ctgttcctgc tgcgctccgc cctggccgac ttcagcctgg acaacgaggt gcactcgagc | 120 |
| ttcatccacc ggcgcctccg cagccaggag cggcgggaga tgcagcgcga tcctctctct | 180 |
| atctggggct gccccatcg cccgcgcccc cacctccagg gcaagcacaa ctcggcgccc | 240 |
| atgttcatgc tggacctgta caacgccatg gcggtggagg agggcggcgg gcccgacggc | 300 |
| cagggcttct cctaccccta caaggccgtc ttcagtaccc agggccccc tctgccagc | 360 |
| ctgcaagata gccgcttcct caccgacgcc gacatggtca tgagcttcgt caacctcgtg | 420 |
| gagcacgaca aagagttctt ccacccacgt taccaccacc gggagttccg gtttgatctt | 480 |
| tccaagatcc cagaagggga agccgtgacc gcagccgaat tccgcatcta caaggactac | 540 |
| atccgggaac gctttgataa tgagacgttc cggatcagcg tttaccaggt gcttcaggag | 600 |
| cacttgggca gggagtctga cctgttcctg ctggacagcc gtacgctctg ggcctcggag | 660 |
| gagggctggc tggtgttcga catcacggcc accagcaacc actgggtggt caacccgcgg | 720 |
| cacaatctgg gcctgcagct ctgcgtggag accttggacg ggcagagcat caaccccaag | 780 |
| ttggcgggcc tgatcgggag gcacgggccc cagaacaagc agcccttcat ggtggccttc | 840 |
| ttcaaggcca cggaggtcca ccttcgcagc acccgctcca caggggggcaa gcaacgcagc | 900 |
| cagaaccgct ccaagacgcc caagaaccag gaagccctgc gggtgaccaa cgtcgcagaa | 960 |
| aacagcagca gtgaccagag gcaggcttgt aagaagcacg agctgtacgt cagcttccgc | 1020 |
| gacctgggct ggcaggactg gatcatcgct cccgaaggct atgctgctta ctactgcgag | 1080 |
| ggggagtgtg ccttccctct gaactcctac atgaacgcca ccaaccacgc catcgtgcag | 1140 |
| acgctggtcc acttcatcaa cccggagacg gtgcccaagc cgtgctgtgc ccccacgcag | 1200 |

```
ctcaacgcca tctctgtgct ctacttcgac gacagctcca acgtcatcct gaagaaatac   1260
agaaacatgg tcgtccgagc ctgtggctgc cactagtag                           1299
```

<210> SEQ ID NO 19
<211> LENGTH: 431
<212> TYPE: PRT
<213> ORGANISM: Felis catus

<400> SEQUENCE: 19

```
Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Asp Gly Gln Gly Phe Ser Tyr Pro Tyr Lys Ala Val Phe Ser
            100                 105                 110

Thr Gln Gly Pro Pro Leu Ala Ser Leu Gln Asp Ser Arg Phe Leu Thr
    115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
    195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Cys Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Leu
    275                 280                 285

Arg Ser Thr Arg Ser Thr Gly Gly Lys Gln Arg Ser Gln Asn Arg Ser
290                 295                 300

Lys Thr Pro Lys Asn Gln Glu Ala Leu Arg Val Thr Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
```

|  |  | 355 |  |  |  | 360 |  |  |  | 365 |  |
|---|---|---|---|---|---|---|---|---|---|---|---|
| Ser | Tyr | Met | Asn | Ala | Thr | Asn | His | Ala | Ile | Val | Gln | Thr | Leu | Val | His |
|  |  | 370 |  |  |  | 375 |  |  |  | 380 |  |

| Phe | Ile | Asn | Pro | Glu | Thr | Val | Pro | Lys | Pro | Cys | Cys | Ala | Pro | Thr | Gln |
| 385 |  |  |  | 390 |  |  |  | 395 |  |  |  | 400 |  |

| Leu | Asn | Ala | Ile | Ser | Val | Leu | Tyr | Phe | Asp | Asp | Ser | Ser | Asn | Val | Ile |
|  |  |  |  | 405 |  |  |  | 410 |  |  |  | 415 |  |

| Leu | Lys | Lys | Tyr | Arg | Asn | Met | Val | Val | Arg | Ala | Cys | Gly | Cys | His |
|  |  |  | 420 |  |  |  | 425 |  |  |  | 430 |  |

<210> SEQ ID NO 20
<211> LENGTH: 6223
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 20

```
ttggctattg gccattgcat acgttgtatc catatcataa tatgtacatt tatattggct     60
catgtccaac attaccgcca tgttgacatt gattattgac tagttattaa tagtaatcaa    120
ttacggggtc attagttcat agcccatata tggagttccg cgttacataa cttacggtaa    180
atggcccgcc tggctgaccg cccaacgacc cccgcccatt gacgtcaata atgacgtatg    240
ttcccatagt aacgccaata gggactttcc attgacgtca atgggtggag tatttacggt    300
aaactgccca cttggcagta catcaagtgt atcatatgcc aagtacgccc cctattgacg    360
tcaatgacgg taaatggccc gcctggcatt atgcccagta catgacctta tgggactttc    420
ctacttggca gtacatctac gtattagtca tcgctattac catggtgatg cggttttggc    480
agtacatcaa tgggcgtgga tagcggtttg actcacgggg atttccaagt ctccacccca    540
ttgacgtcaa tgggagtttg ttttggcacc aaaatcaacg ggactttcca aaatgtcgta    600
acaactccgc cccattgacg caaatgggcg gtaggcgtgt acggtgggag gtctatataa    660
gcagagctcg tttagtgaac cgtcagatcg cctggagacg ccatccacgc tgttttgacc    720
tccatagaag acaccgggac cgatccagcc tccgcggccg ggaacggtgc attggaacgc    780
ggattcccg tgccaagagt gacgtaagta ccgcctatag actctatagg cacacccctt    840
tggcttctta tgcatgctat actgttttg gcttggggcc tatacacccc gcttcctta     900
tgctataggt gatggtatag cttagcctat aggtgtgggt tattgaccat tattgaccac    960
tcccctattg gtgacgatac tttccattac taatccataa catggctctt gccacaact    1020
atctctattg gctatatgcc aatactctgt ccttcagaga ctgacacgga ctctgtattt    1080
ttacaggatg gggtcccatt tattatttac aaattcacat atacaacaac gccgtcccc    1140
gtgcccgcag ttttattaa acatagcgtg gatctccac gcgaatctcg ggtacgtgtt    1200
ccggacatgg gctcttctcc ggtagcggcg gagcttccac atccgagccc tggtcccatg    1260
cctccagcgg ctcatggtcg ctcggcagct ccttgctcct aacagtggag gccagactta    1320
ggcacagcac aatgcccacc accaccagtg tgccgcacaa ggccgtggcg tagggtatg    1380
tgtctgaaaa tgagcgtgga gattgggctc gcacggctga cgcagatgga agacttaagg    1440
cagcggcaga agaagatgca ggcagctgag ttgttgtatt ctgataagag tcagaggtaa    1500
ctcccgttgc ggtgctgtta acggtggagg gcagtgtagt ctgagcagta ctcgttgctg    1560
ccgcgcgcgc caccagacat aatagctgac agactaacag actgttcctt tccatgggtc    1620
ttttctgcag tcaccgtcgt cgacacgtgt gatcagatat cgcggccgcg ccaccatgca    1680
```

```
cgtgcgctca ctgcgagctg cggcgccgca cagcttcgtg gcgctctggg cacccctgtt    1740
cctgctgcgc tccgccctgg ccgacttcag cctggacaac gaggtgcact cgagcttcat    1800
ccaccggcgc ctccgcagcc aggagcggcg ggagatgcag cgcgagatcc tctctatctt    1860
gggcttgccc catcgcccgc gcccccacct ccagggcaag cacaactcgg cgcccatgtt    1920
catgctggac ctgtacaacg ccatggcggt ggaggagggc ggcgggcccg acggccaggg    1980
cttctcctac ccctacaagg ccgtcttcag tacccagggc ccccctctgg ccagcctgca    2040
agatagccgc ttcctcaccg acgccgacat ggtcatgagc ttcgtcaacc tcgtggagca    2100
cgacaaagag ttcttccacc cacgttacca ccaccgggag ttccggtttg atctttccaa    2160
gatcccagaa ggggaagccg tgaccgcagc cgaattccgc atctacaagg actacatccg    2220
ggaacgcttt gataatgaga cgttccggat cagcgtttac caggtgcttc aggagcactt    2280
gggcagggag tctgacctgt tcctgctgga cagccgtacg ctctgggcct cggaggaggg    2340
ctggctggtg ttcgacatca cggccaccag caaccactgg gtggtcaacc gcggcacaa    2400
tctgggcctg cagctctgcg tggagacctt ggacgggcag agcatcaacc ccaagttggc    2460
gggcctgatc gggaggcacg ggccccagaa caagcagccc ttcatggtgg ccttcttcaa    2520
ggccacggag gtccaccttc gcagcacccg ctccacaggg ggcaagcaac gcagccagaa    2580
ccgctccaag acgcccaaga accaggaagc cctgcgggtg accaacgtcg cagaaaacag    2640
cagcagtgac cagaggcagg cttgtaagaa gcacgagctg tacgtcagct ccgcgacct    2700
gggctggcag gactggatca tcgctcccga aggctatgct gcttactact gcgagggga    2760
gtgtgccttc cctctgaact cctacatgaa cgccaccaac cacgccatcg tgcagacgct    2820
ggtccacttc atcaacccgg agacggtgcc caagccgtgc tgtgccccca cgcagctcaa    2880
cgccatctct gtgctctact tcgacgacag ctccaacgtc atcctgaaga atacagaaa    2940
catggtcgtc cgagcctgtg gctgccacta gtagggatcc tctagaccag gccctggatc    3000
cagatctgct gtgccttcta gttgccagcc atctgttgtt tgcccctccc ccgtgccttc    3060
cttgaccctg gaaggtgcca ctcccactgt cctttcctaa taaaatgagg aaattgcatc    3120
gcattgtctg agtaggtgtc attctattct ggggggtggg gtggggcagg acagcaaggg    3180
ggaggattgg gaagacaata gcaggcatgc tggggatgcg gtgggctcta tgggtaccca    3240
ggtgctgaag aattgacccg gttcctcctg ggccagaaag aagcaggcac atccccttct    3300
ctgtgacaca ccctgtccac gcccctggtt cttagttcca gccccactca taggacactc    3360
atagctcagg agggctccgc cttcaatccc accgctaaa gtacttggag cggtctctcc    3420
ctccctcatc agcccaccaa accaaaccta gcctccaaga gtgggaagaa attaaagcaa    3480
gataggctat taagtgcaga gggagagaaa atgcctccaa catgtgagga agtaatgaga    3540
gaaatcatag aatttcttcc gcttcctcgc tcactgactc gctgcgctcg gtcgttcggc    3600
tgcggcgagc ggtatcagct cactcaaagg cggtaatacg gttatccaca gaatcagggg    3660
ataacgcagg aaagaacatg tgagcaaaag gccagcaaaa ggccaggaac cgtaaaaagg    3720
ccgcgttgct ggcgtttttc cataggctcc gcccccctga cgagcatcac aaaaatcgac    3780
gctcaagtca gaggtggcga aacccgacag gactataaag ataccaggcg tttccccctg    3840
gaagctccct cgtgcgctct cctgttccga cctgccgct taccggatac ctgtccgcct    3900
ttctcccttc gggaagcgtg gcgctttctc atagctcacg ctgtaggtat ctcagttcgg    3960
tgtaggtcgt tcgctccaag ctgggctgtg tgcacgaacc cccgttcag cccgaccgct    4020
gcgccttatc cggtaactat cgtcttgagt ccaacccggt aagacacgac ttatcgccac    4080
```

```
tggcagcagc cactggtaac aggattagca gagcgaggta tgtaggcggt gctacagagt    4140
tcttgaagtg gtggcctaac tacggctaca ctagaagaac agtatttggt atctgcgctc    4200
tgctgaagcc agttaccttc ggaaaaagag ttggtagctc ttgatccggc aaacaaacca    4260
ccgctggtag cggtggtttt tttgtttgca agcagcagat tacgcgcaga aaaaaaggat    4320
ctcaagaaga tcctttgatc ttttctacgg ggtctgacgc tcagtggaac gaaaactcac    4380
gttaagggat tttggtcatg agattatcaa aaaggatctt cacctagatc cttttaaatt    4440
aaaaatgaag ttttaaatca atctaaagta tatatgagta aacttggtct gacagttacc    4500
aatgcttaat cagtgaggca cctatctcag cgatctgtct atttcgttca tccatagttg    4560
cctgactcgg gggggggggg cgctgaggtc tgcctcgtga agaaggtgtt gctgactcat    4620
accaggcctg aatcgcccca tcatccagcc agaaagtgag ggagccacgg ttgatgagag    4680
ctttgttgta ggtggaccag ttggtgattt tgaacttttg ctttgccacg gaacggtctg    4740
cgttgtcggg aagatgcgtg atctgatcct tcaactcagc aaaagttcga tttattcaac    4800
aaagccgccg tcccgtcaag tcagcgtaat gctctgccag tgttacaacc aattaaccaa    4860
ttctgattag aaaaactcat cgagcatcaa atgaaactgc aatttattca tatcaggatt    4920
atcaatacca tatttttgaa aaagccgttt ctgtaatgaa ggagaaaact caccgaggca    4980
gttccatagg atggcaagat cctggtatcg gtctgcgatt ccgactcgtc aacatcaat     5040 acaacctatt aatttcccct cgtcaaaaat aaggttatca agtgagaaat caccatgagt    5100
gacgactgaa tccggtgaga atggcaaaag cttatgcatt tctttccaga cttgttcaac    5160
aggccagcca ttacgctcgt catcaaaatc actcgcatca accaaaccgt tattcattcg    5220
tgattgcgcc tgagcgagac gaaatacgcg atcgctgtta aaaggacaat acaaacagg     5280 aatcgaatgc aaccgcgcca ggaacactgc cagcgcatca acaatatttt cacctgaatc    5340
aggatattct tctaatacct ggaatgctgt tttcccgggg atcgcagtgg tgagtaacca    5400
tgcatcatca ggagtacgga taaaatgctt gatggtcgga agaggcataa attccgtcag    5460
ccagtttagt ctgaccatct catctgtaac atcattggca acgctacctt tgccatgttt    5520
cagaaacaac tctggcgcat cgggcttccc atacaatcga tagattgtcg cacctgattg    5580
cccgacatta tcgcgagccc atttataccc atataaatca gcatccatgt tggaatttaa    5640
tcgcggcctc gagcaagacg tttcccgttg aatatggctc ataacacccc ttgtattact    5700
gtttatgtaa gcagacagtt ttattgttca tgatgatata tttttatctt gtgcaatgta    5760
acatcagaga ttttgagaca acgtggct ttccccccccc ccccattatt gaagcattta    5820
tcagggttat tgtctcatga gcggatacat atttgaatgt atttagaaaa ataaacaaat    5880
aggggttccg cgcacatttc cccgaaaagt gccacctgac gtctaagaaa ccattattat    5940
catgacatta acctataaaa ataggcgtat cacgaggccc tttcgtctcg cgcgtttcgg    6000
tgatgacggt gaaaacctct gacacatgca gctcccggag acggtcacag cttgtctgta    6060
agcggatgcc gggagcagac aagcccgtca gggcgcgtca gcgggtgttg gcgggtgtcg    6120
gggctggctt aactatgcgg catcagagca gattgtactg agagtgcacc atatgcggtg    6180
tgaaataccg cacagatgcg taaggagaaa ataccgcatc aga                      6223
```